(12) United States Patent
Hatakeyama et al.

(10) Patent No.: US 10,101,654 B2
(45) Date of Patent: Oct. 16, 2018

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/692,013

(22) Filed: Aug. 31, 2017

(65) Prior Publication Data

US 2018/0081267 A1 Mar. 22, 2018

(30) Foreign Application Priority Data

Sep. 20, 2016 (JP) .................. 2016-183025

(51) Int. Cl.

| | | |
|---|---|---|
| G03F 7/004 | (2006.01) | |
| G03F 7/38 | (2006.01) | |
| G03F 7/40 | (2006.01) | |
| C07C 69/76 | (2006.01) | |
| C07C 69/78 | (2006.01) | |
| C08F 212/02 | (2006.01) | |
| C08F 220/22 | (2006.01) | |
| C08F 220/24 | (2006.01) | |
| C08F 220/38 | (2006.01) | |
| C08F 224/00 | (2006.01) | |
| C08F 228/02 | (2006.01) | |
| G03F 7/20 | (2006.01) | |
| G03F 7/039 | (2006.01) | |
| C07C 309/17 | (2006.01) | |
| C07C 309/09 | (2006.01) | |
| C07C 309/24 | (2006.01) | |
| C07C 303/32 | (2006.01) | |
| C07C 309/06 | (2006.01) | |
| C07C 309/04 | (2006.01) | |
| C07C 309/19 | (2006.01) | |
| C07C 69/753 | (2006.01) | |
| G03F 7/038 | (2006.01) | |
| G03F 7/16 | (2006.01) | |
| G03F 7/30 | (2006.01) | |
| C08F 220/30 | (2006.01) | |
| C08F 220/28 | (2006.01) | |

(52) U.S. Cl.
CPC .......... *G03F 7/0045* (2013.01); *C07C 69/753* (2013.01); *C07C 69/76* (2013.01); *C07C 69/78* (2013.01); *C07C 303/32* (2013.01); *C07C 309/04* (2013.01); *C07C 309/06* (2013.01); *C07C 309/09* (2013.01); *C07C 309/17* (2013.01); *C07C 309/19* (2013.01); *C07C 309/24* (2013.01); *C08F 212/02* (2013.01); *C08F 220/22* (2013.01); *C08F 220/24* (2013.01); *C08F 220/38* (2013.01); *C08F 224/00* (2013.01); *C08F 228/02* (2013.01); *G03F 7/0382* (2013.01); *G03F 7/0392* (2013.01); *G03F 7/0397* (2013.01); *G03F 7/16* (2013.01); *G03F 7/2004* (2013.01); *G03F 7/2006* (2013.01); *G03F 7/2037* (2013.01); *G03F 7/30* (2013.01); *G03F 7/38* (2013.01); *C08F 2220/282* (2013.01); *C08F 2220/283* (2013.01); *C08F 2220/303* (2013.01); *C08F 2220/382* (2013.01)

(58) Field of Classification Search
CPC .. G03F 7/00457; G03F 7/0382; G03F 7/0397; G03F 7/38; G03F 7/2006; G03F 7/2037; C07C 303/32; C07C 309/04; C07C 309/06; C07C 309/09; C07C 309/17; C07C 309/19; C07C 309/24; C07C 69/753; C07C 69/76; C07C 69/78; C08F 212/02; C08F 220/22; C08F 220/24; C08F 220/38; C08F 2220/282; C08F 2220/283; C08F 2220/303; C08F 2220/382; C08F 224/00; C08F 228/02
USPC ..... 430/270.1, 326, 905, 907, 910; 526/243, 526/245, 247, 248, 249, 266, 280, 281, 526/282, 286, 287, 288, 291, 292.1, 526/292.5, 292.9, 293, 294; 560/21, 83, 560/88, 116, 117
See application file for complete search history.

(56) References Cited

U.S. PATENT DOCUMENTS 6,200,724 B1* 3/2001 Namiki ................ G03F 7/0045
430/270.1
2013/0084529 A1 4/2013 Hatakeyama et al.
2016/0122292 A1* 5/2016 Sakai .................... C07D 311/86
204/157.61

FOREIGN PATENT DOCUMENTS

| JP | 2010-84144 A | 4/2010 |
|---|---|---|
| JP | 2013-15565 A | 1/2013 |
| JP | 2013-80033 A | 5/2013 |
| TW | 201512159 A | 4/2015 |

OTHER PUBLICATIONS

Office Action dated May 22, 2018, issued in counterpart Taiwanese Application No. 106132050. (7 pages).

* cited by examiner

*Primary Examiner* — John S Chu
(74) *Attorney, Agent, or Firm* — Westerman, Hattori, Daniels & Adrian, LLP

(57) ABSTRACT

A resist composition comprising a 2,5,8,9-teraaza-1-phosphabicyclo[3.3.3]undocane, biguanide or phosphazene salt of an iodinated aromatic group-containing carboxylic acid exhibits a sensitizing effect and an acid diffusion suppressing effect and forms a pattern having improved resolution, LWR and CDU.

15 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2016-183025 filed in Japan on Sep. 20, 2016, the entire contents of which are hereby incorporated by reference.

TECHNICAL FIELD

This invention relates to a resist composition comprising a 2,5,8,9-tetraaza-1-phosphabicyclo[3.3.3]undecane, biguanide or phosphazene salt of an iodinated aromatic group-containing carboxylic acid, and a patterning process using the same.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, BUV lithography of 13.5 nm wavelength, and double patterning version of the ArF lithography, on which active research efforts have been made.

The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage increased from 10 kV to 30 kV and reached 50 kV in the current mainstream system, with a voltage of 100 kV being under investigation.

As the pattern feature size Is reduced, approaching to the diffraction limit of light, light contrast lowers. In the case of positive resist film, a lowering of light contrast leads to reductions of resolution and focus margin of hole and trench patterns.

As the pattern feature size is reduced, the edge roughness (LWR) of line patterns and the critical dimension uniformity (CDU) of hole patterns are regarded significant. It is pointed out that these factors are affected by the segregation or agglomeration of a base polymer and acid generator and the diffusion of generated acid. There is a tendency that as the resist film becomes thinner, LWR becomes greater. A film thickness reduction to comply with the progress of size reduction causes a degradation of LWR, which becomes a serious problem.

The EUV lithography resist must meet high sensitivity, high resolution and low LWR at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR. It would be desirable to have a resist material having a high sensitivity and resolution as well as improved LWR and CDU.

Patent Document 1 proposes a base generator capable of generating a biguanide or phosphazene salt. Upon exposure, the base generator generates a strong base, biguanide or phosphazene, promoting crosslinking of epoxy groups or the like. Patent Document 2 proposes a resist composition comprising a biguanide compound and an acid generator wherein the biguanide functions as a quencher for trapping acid.

CITATION LIST

Patent Document 1: JP-A 2010-084144
Patent Document 2: JP-A 2013-015565

SUMMARY OF INVENTION

As the wavelength of light becomes shorter, the energy density thereof becomes higher and hence, the number of photons generated upon exposure becomes smaller. A variation in photon number causes variations in LWR and CDU. As the exposure dose increases, the number of photons increases, leading to a less variation of photon number. Thus there is a tradeoff relationship between sensitivity and resolution, LWR and CDU. In particular, the EUV lithography resist materials have the tendency that a lower sensitivity leads to better LWR and CDU.

An increase in acid diffusion also causes degradation of resolution, LWR and CDU. This is because acid diffusion not only causes image blur, but also proceeds non-uniformly in a resist film. For suppressing acid diffusion, it is effective to lower the PEB temperature, to use a bulky acid which is least diffusive, or to increase the amount of quencher added. However, any of these means for reducing acid diffusion results in a lowering of sensitivity. Either the means for reducing photon variation or the means for reducing acid diffusion variation leads to a lowering of resist sensitivity.

An object of the invention is to provide a resist composition which exerts a high sensitizing effect and an acid diffusion suppressing effect and has improved resolution, LWR and CDU, and a pattern forming process using the same.

A significant increase of acid generation efficiency and a significant suppression of acid diffusion must be achieved before the tradeoff relationship between sensitivity and resolution, LWR and CDU can be overcome.

Iodine is substantially absorptive to EUV of wavelength 13.5 nm and EB because of its high atomic number, and releases many secondary electrons upon exposure because of many electron orbits in its molecule. The secondary electrons thus released provide energy transfer to an acid generator, achieving a high sensitizing effect.

The inventors have found that when a salt of an iodinated aromatic group-containing carboxylic acid with a 2,5,8,9-tetraaza-1-phosphabicyclo[3.3.3]undecane, biguanide or phosphazene compound is added to a base polymer, the resulting resist composition forms a resist film which exerts a high sensitizing effect and an acid diffusion suppressing effect and has a high sensitivity, minimized LWR and improved CDU. The 2,5,8,9-tetraaza-1-phosphabicyclo[3.3.3]undecane, biguanide and phosphazene compounds are sometimes referred to as "organic base" for simplicity sake.

In one aspect, the invention provides a resist composition comprising a base polymer and a 2,5,8,9-tetraaza-1-phosphabicyclo[3.3.3]undecane, biguanide or phosphazene salt of an iodinated aromatic group-containing carboxylic acid.

In a preferred embodiment, the salt has the formula (A).

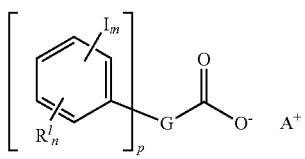

Herein $R^1$ is hydrogen, hydroxyl, a $C_1$-$C_6$ straight, branched or cyclic alkyl group, $C_1$-$C_6$ straight, branched or cyclic alkoxy group, $C_2$-$C_6$ straight, branched or cyclic acyloxy group, fluorine, chlorine, bromine, amino, —$NR^2$—C(=O)—$R^3$, or —$NR^2$—C(=O)—O—$R^3$, wherein $R^2$ is hydrogen or a $C_1$-$C_6$ straight, branched or cyclic alkyl group, and $R^3$ is a $C_1$-$C_6$ straight, branched or cyclic alkyl group or $C_2$-$C_8$ straight, branched or cyclic alkenyl group. G is a single bond or a $C_1$-$C_{20}$ (p+1)-valent linking group which may contain an ether, carbonyl, ester, amide, sultone, lactam, carbonate, halogen, hydroxyl or carboxyl moiety, p is an integer of 1 to 3, m is an integer of 1 to 5, n is an integer of 0 to 3. $A^+$ is a cation having the formula (A)-1, (A)-2 or (A)-3.

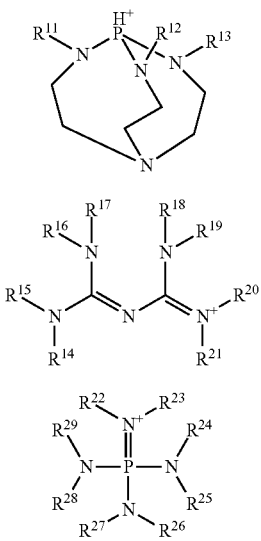

Herein $R^{11}$ to $R^{13}$ are each independently hydrogen, a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group. $R^{14}$ to $R^{21}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxyl, thiol, or nitro moiety, or a pair of $R^{14}$ and $R^{15}$, $R^{15}$ and $R^{16}$, $R^{16}$ and $R^{17}$, $R^{17}$ and $R^{18}$, $R^{18}$ and $R^{19}$, $R^{19}$ and $R^{20}$, or $R^{20}$ and $R^{21}$ may bond together to form a ring which may contain an ether moiety. $R^{22}$ to $R^{29}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxyl, thiol, or nitro moiety, or a pair of $R^{22}$ and $R^{23}$, $R^{23}$ and $R^{24}$, $R^{24}$ and $R^{25}$, $R^{25}$ and $R^{26}$, $R^{26}$ and $R^{27}$, or $R^{27}$ and $R^{28}$ may bond together to form a ring, or $R^{23}$ and $R^{24}$, $R^{25}$ and $R^{26}$, $R^{27}$ and $R^{28}$, or $R^{28}$ and $R^{29}$, taken together, may form a group having the formula (A)-3-1, or when $R^{22}$ is hydrogen, $R^{23}$ may be a group having the formula (A)-3-2.

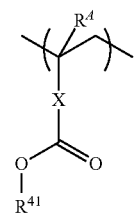

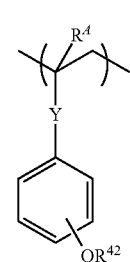

Herein $R^{30}$ to $R^{39}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, or a pair of $R^{30}$ and $R^{31}$, $R^{31}$ and $R^{32}$, $R^{32}$ and $R^{33}$, $R^{33}$ and $R^{34}$, $R^{34}$ and $R^{35}$, $R^{36}$ and $R^{37}$, or $R^{38}$ and $R^{39}$ may bond together to form a ring, or $R^{30}$ and $R^{31}$, $R^{32}$ and $R^{33}$, or $R^{34}$ and $R^{35}$, taken together, may form a group having the formula (A)-3-1.

The resist composition may further comprise an acid generator capable of generating sulfonic acid, sulfonimide or sulfonmethide.

The resist composition may further comprise an organic solvent.

In a preferred embodiment, the base polymer comprises recurring units having the formula (a1) or recurring units having the formula (a2).

Herein $R^A$ is each independently hydrogen or methyl, $R^{41}$ and $R^{42}$ are each independently an acid labile group, X is a single bond, phenylene, naphthylene, or a $C_1$-$C_{12}$ linking group containing ester moiety or lactone ring, and Y is a single bond or ester group.

The resist composition may further comprise a dissolution inhibitor.

In one embodiment, the resist composition is a chemically amplified positive resist composition.

In another embodiment, the base polymer is an acid labile group-free polymer. The resist composition may further comprise a crosslinker. Then the resist composition is a chemically amplified negative resist composition.

In one preferred embodiment, the base polymer further comprises recurring units of at least one type selected from recurring units having the formulae (f1) to (f3).

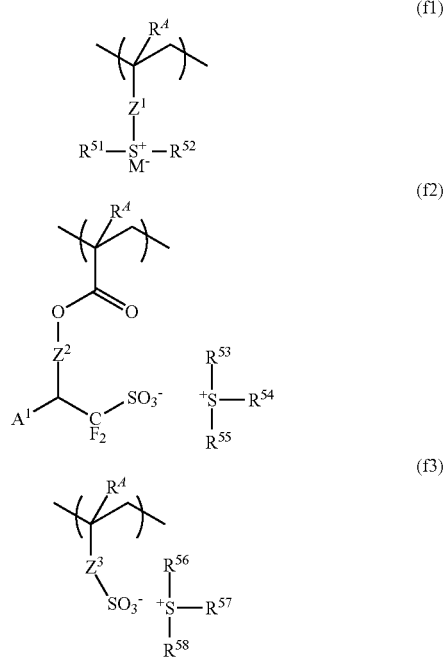

Herein $R^A$ is each independently hydrogen or methyl. $Z^1$ is a single bond, phenylene, —O—$Z^{11}$—, or —C(=O)—$Z^{12}$—$Z^{11}$—, $Z^{11}$ is a straight, branched or cyclic $C_1$-$C_6$ alkylene group or straight, branched or cyclic $C_2$-$C_6$ alkenylene group which may contain a carbonyl, ester, ether or hydroxyl moiety, or phenylene group, $Z^{12}$ is —O— or —NH—. $R^{51}$, $R^{52}$, $R^{53}$, $R^{54}$, $R^{55}$, $R^{56}$, $R^{57}$, and $R^{58}$ are each independently a straight, branched or cyclic $C_1$-$C_{12}$ alkyl group which may contain a carbonyl, ester or ether moiety, or a $C_6$-$C_{12}$ aryl, $C_7$-$C_{20}$ aralkyl, or mercaptophenyl group. $Z^2$ is a single bond, —$Z^{21}$—C(=O)—O—, —$Z^{21}$—O—, or —$Z^{21}$—O—C(=O)—, $Z^{21}$ is a straight, branched or cyclic $C_1$-$C_{12}$ alkylene group which may contain a carbonyl, ester or ether moiety. $Z^3$ is a single bond, methylene, ethylene, phenylene, fluorinated phenylene, —O—$Z^{31}$—, or —C(=O)—$Z^{32}$—$Z^{31}$—, $Z^{31}$ is a straight, branched or cyclic $C_1$-$C_6$ alkylene group or straight, branched or cyclic $C_2$-$C_6$ alkenylene group which may contain a carbonyl, ester, ether or hydroxyl moiety, or a phenylene, fluorinated phenylene or trifluormethyl-substituted phenylene group, $Z^{32}$ is —O— or —NH—. $A^1$ is hydrogen or trifluoromethyl, and $M^-$ is a non-nucleophilic counter ion.

The resist composition may further comprise a surfactant.

In another aspect, the invention provides a pattern forming process comprising the steps of coating the resist composition defined above onto a substrate, baking, exposing the resulting resist film to high-energy radiation, and developing with a developer.

Typically, the high-energy radiation is ArF excimer laser of wavelength 193 nm, KrF excimer laser of wavelength 248 nm, EB or EUV of wavelength 3 to 15 nm.

ADVANTAGEOUS EFFECTS OF INVENTION

Because of inclusion of iodine featuring substantial light absorption, a resist film containing a 2,5,8,9-tetraaza-1-phosphabicyclo[3.3.3]undecane, biguanide or phosphazene salt of an iodinated aromatic group-containing carboxylic acid exhibits a sensitizing effect due to secondary electrons released therefrom upon exposure, an acid diffusion suppressing effect, and a high dissolution contrast. Thus the resist film exhibits high resolution, high sensitivity, and minimal LWR as a positive or negative resist film subject to alkaline development or as a negative resist film subject to organic solvent development.

DESCRIPTION OF EMBODIMENTS

As used herein, the singular forms "a," "an" and "the" include plural referents unless the context clearly dictates otherwise. The notation ($C_n$-$C_m$) means a group containing from n to n carbon atoms per group. Me stands for methyl, Ac for acetyl, and Ph for phenyl. As used herein, the term "iodinated" or "fluorinated" indicates that a compound contains iodine or fluorine.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity
Resist Composition The resist composition of the invention is defined as comprising a base polymer and a 2,5,8,9-tetraaza-1-phosphabicyclo[3.3.3]undecane, biguanide or phosphazene salt of an iodinated aromatic group-containing carboxylic acid. The 2,5,8,9-tetraaza-1-phosphabicyclo[3.3.3]undecane, biguanide or phosphazene salt of an iodinated aromatic group-containing carboxylic acid is sometimes referred to as "iodinated aromatic carboxylic salt" for simplicity sake. The iodinated aromatic carboxylic salt undergoes ion exchange with sulfonic acid, sulfonimide or sulfonmethide generated from an acid generator, especially sulfonic acid containing fluorinated alkyl, bissulfonimide or trissulfonmethide, to form a salt and to release an iodinated aromatic group-containing carboxylic acid salt. The organic base has an acid trapping ability and an acid diffusion suppressing effect. Since the iodinated aromatic carboxylic salt is not photosensitive and thus not photo-decomposable, it retains a sufficient acid trapping ability even in the exposed region, suppressing acid diffusion from the exposed region to the unexposed region.

Besides the iodinated aromatic carboxylic salt, another amine compound, ammonium salt, sulfonium salt or iodonium salt may be separately added as the quencher to the resist composition of the invention. The ammonium salt, sulfonium salt or iodonium salt added as quencher is preferably a sulfonium salt or iodonium salt of carboxylic acid, sulfonic acid, sulfonamide or saccharin. The carboxylic acid may or may not be fluorinated at α-position.

The acid diffusion suppressing effect and contrast enhancing effect of the iodinated aromatic carboxylic salt are valid in both the positive or negative pattern formation by alkaline development and the negative pattern formation by organic solvent development.

Iodinated Aromatic Carboxylic Salt

The iodinated aromatic carboxylic salt in the resist composition is a 2,5,8,9-tetraaza-1-phosphabicyclo[3.3.3]undecane, biguanide or phosphazene salt of an iodinated aromatic group-containing carboxylic acid. Typically the iodinated aromatic carboxylic salt has the formula (A).

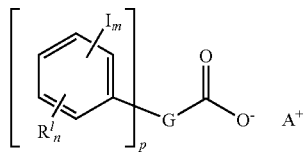

(A)

Herein $R^1$ is hydrogen, hydroxyl, a $C_1$-$C_6$ straight, branched or cyclic alkyl group, $C_1$-$C_6$ straight, branched or cyclic alkoxy group, $C_2$-$C_6$ straight, branched or cyclic acyloxy group, fluorine, chlorine, bromine, amino, —$NR^2$—$C(O)$—$R^3$, or —$NR^2$—$C(=O)$—$O$—$R^3$. $R^2$ is hydrogen or a $C_1$-$C_6$ straight, branched or cyclic alkyl group. $R^3$ is a $C_1$-$C_6$ straight, branched or cyclic alkyl group or $C_2$-$C_8$ straight, branched or cyclic alkenyl group. G is a single bond or a $C_1$-$C_{20}$ (p+1)-valent linking group which may contain an ether, carbonyl, ester, amide, sultone, lactam, carbonate, halogen, hydroxyl or carboxyl moiety, p is an integer of 1 to 3, m is an integer of 1 to 5, and n is an integer of 0 to 3.

$A^+$ is a cation having the formula (A)-1, (A)-2 or (A)-3.

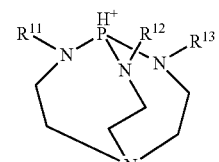

(A)-1

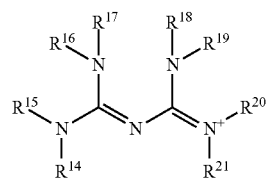

(A)-2

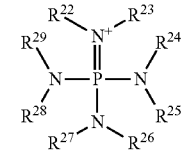

(A)-3

In formula (A)-1, $R^{11}$ to $R^{13}$ are each independently hydrogen, a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group.

In formula (A)-2, $R^{14}$ to $R^{21}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxyl, thiol, or nitro moiety, or a pair of $R^{14}$ and $R^{15}$, $R^{15}$ and $R^{16}$, $R^{16}$ and $R^{17}$, $R^{17}$ and $R^{18}$, $R^{18}$ and $R^{19}$, $R^{19}$ and $R^{20}$, or $R^{20}$ and $R^{21}$ may bond together to form a ring which may contain an ether moiety.

In formula (A)-3, $R^{22}$ to $R^{29}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxyl, thiol, or nitro moiety, or a pair of $R^{22}$ and $R^{23}$, $R^{23}$ and $R^{24}$, $R^{24}$ and $R^{25}$, $R^{25}$ and $R^{26}$, $R^{26}$ and $R^{27}$, or $R^{27}$ and $R^{28}$ may bond together to form a ring, or $R^{23}$ and $R^{24}$, $R^{25}$ and $R^{26}$, $R^{27}$ and $R^{28}$, or $R^{28}$ and $R^{29}$, taken together (i.e., become=in formula (A)-3-1), may form a group having the formula (A)-3-1, or when $R^{22}$ is hydrogen, $R^{23}$ may be a group having the formula (A)-3-2.

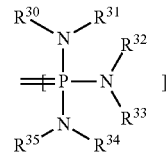

(A)-3-1

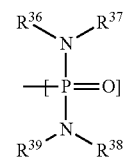

(A)-3-2

Herein $R^{30}$ to $R^{39}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, or a pair of $R^{30}$ and $R^{31}$, $R^{31}$ and $R^{32}$, $R^{32}$ and $R^{33}$, $R^{33}$ and $R^{34}$, $R^{34}$ and $R^{35}$, $R^{36}$ and $R^{37}$, or $R^{38}$ and $R^{39}$ may bond together to form a ring, or $R^{30}$ and $R^{31}$, $R^{32}$ and $R^{33}$, or $R^{34}$ and $R^{35}$, taken together, may form a group having the formula (A)-3-1.

Examples of the anion of the iodinated aromatic carboxylic salt of formula (A) are given below, but not limited thereto.

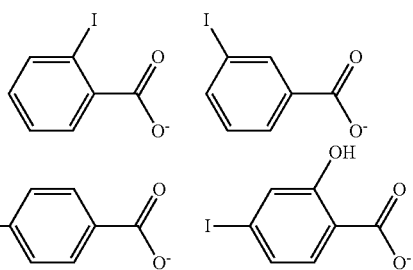

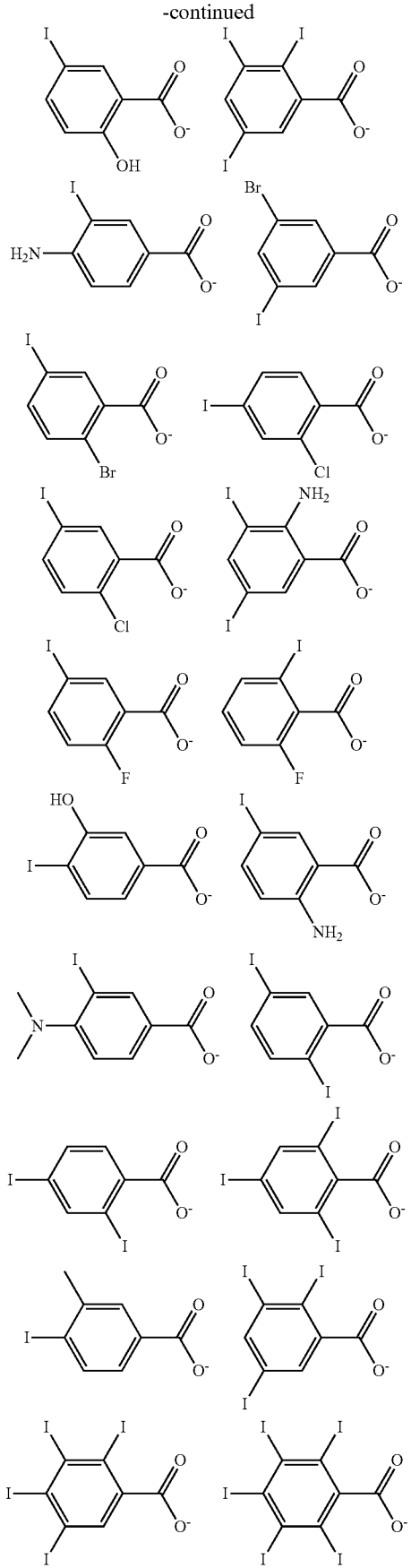
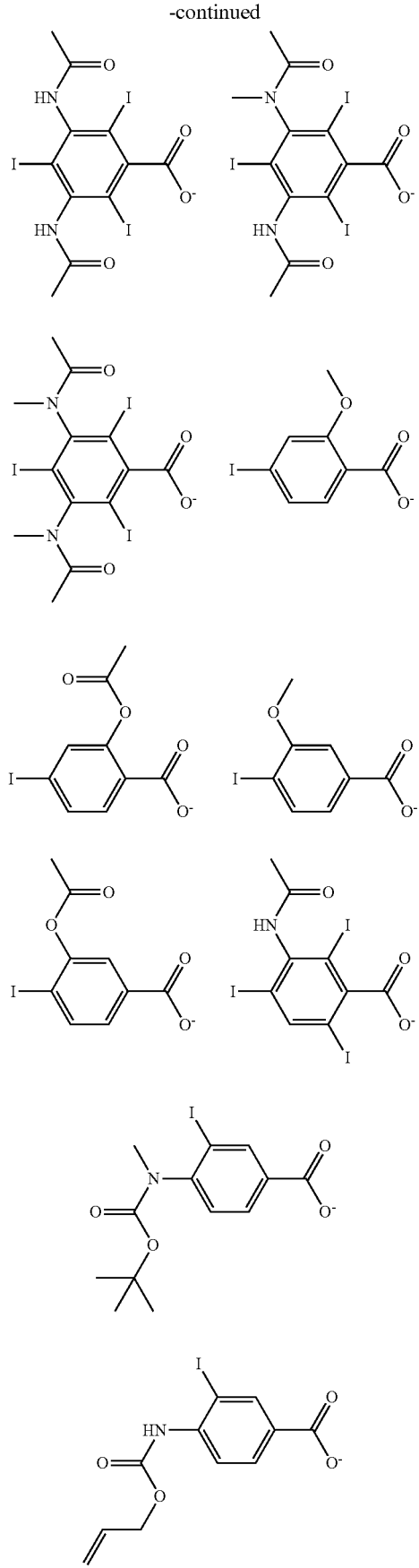

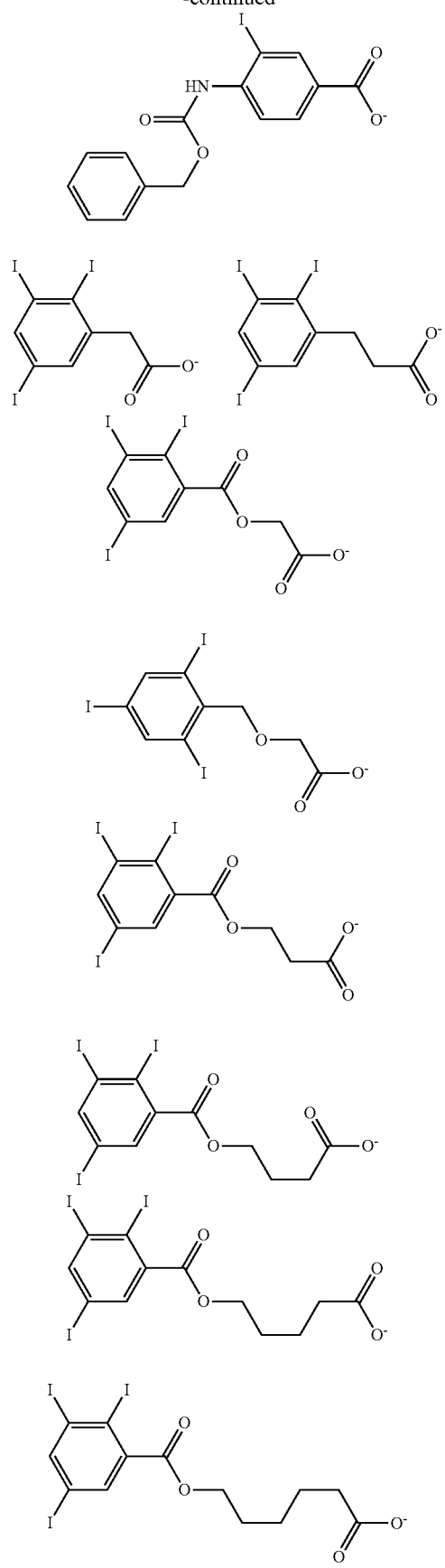
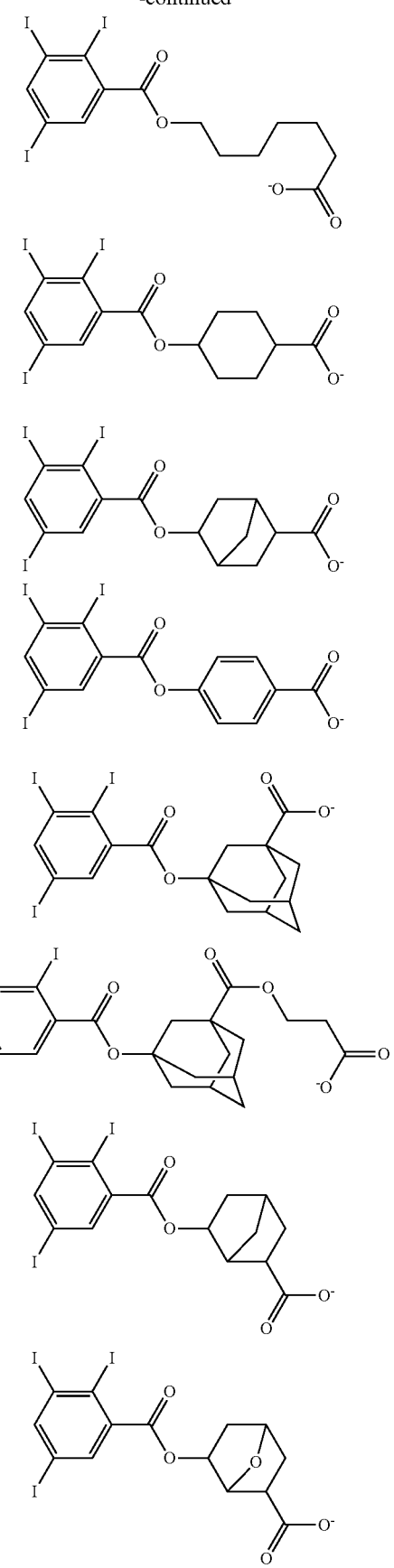

-continued
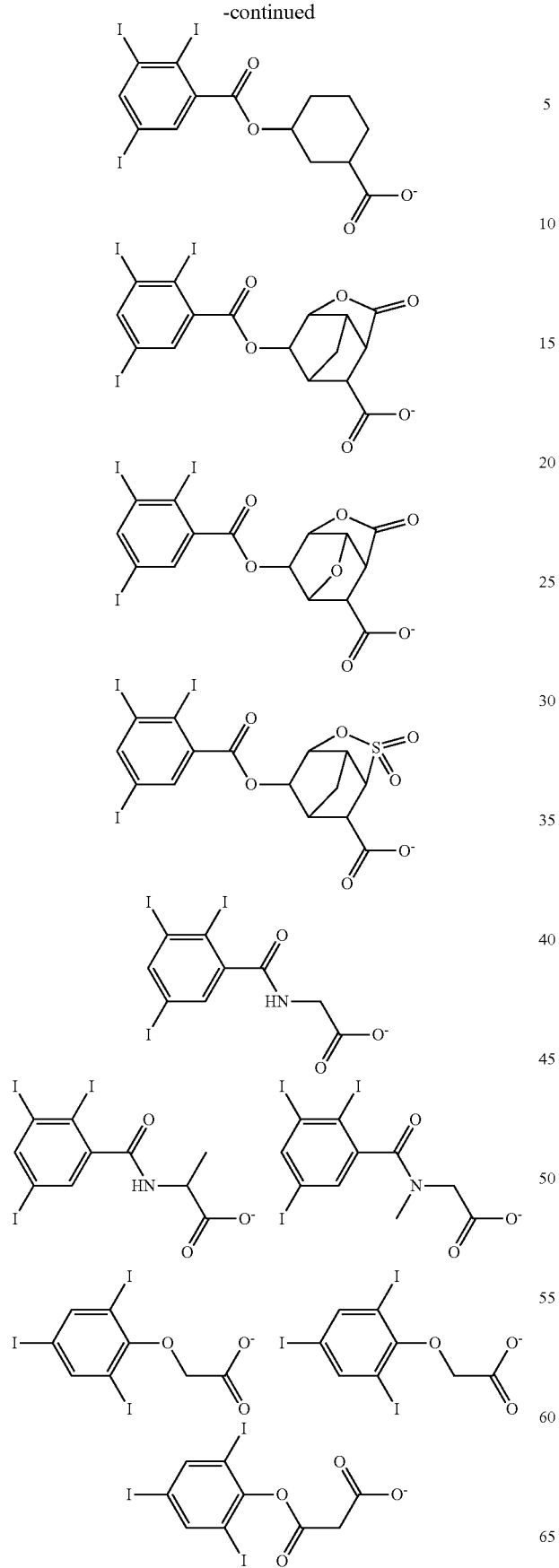
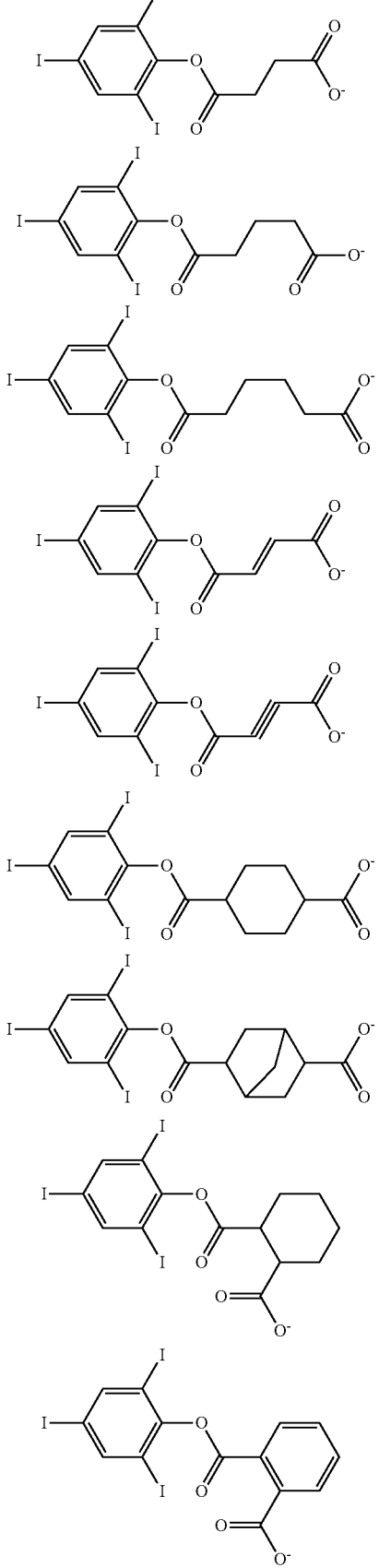

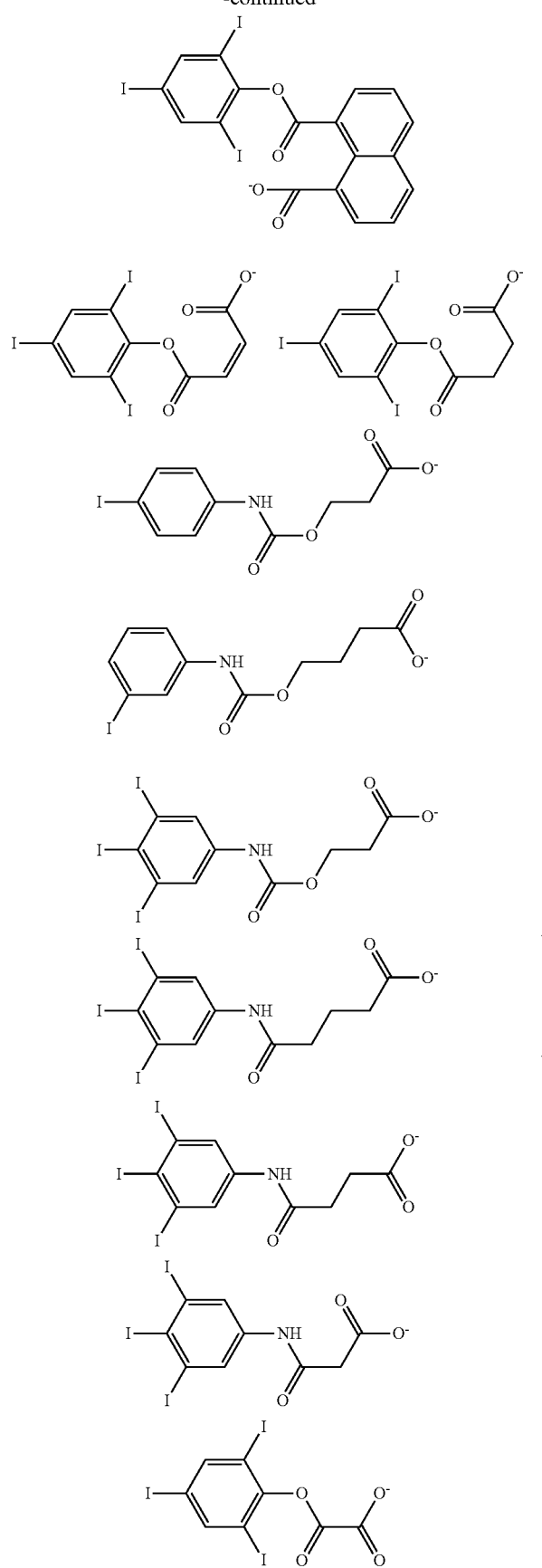
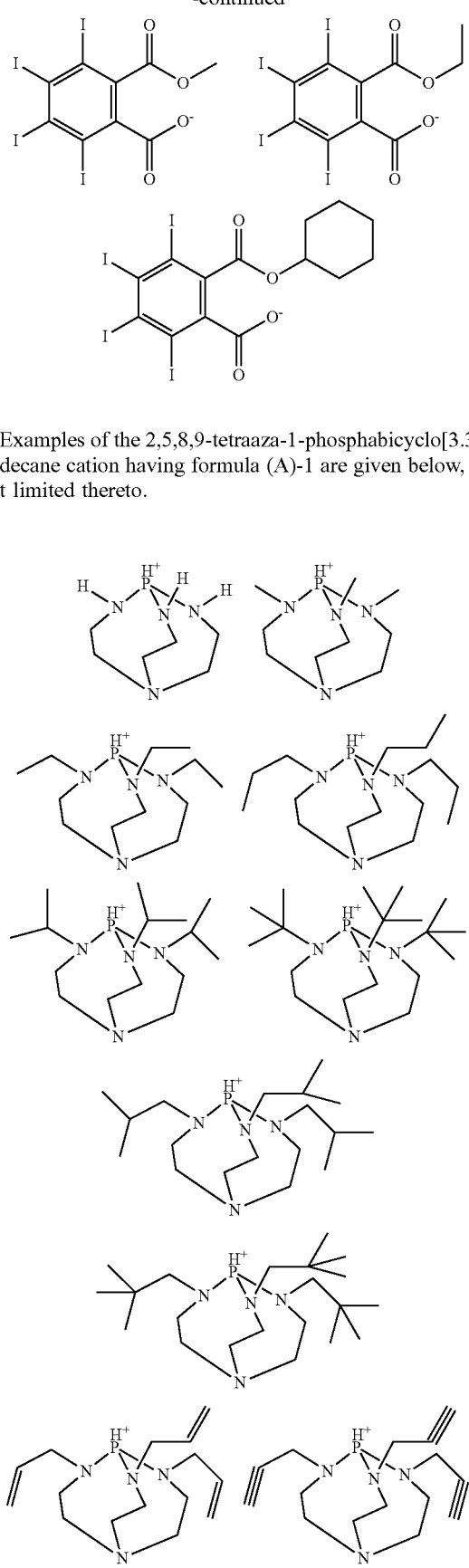
Examples of the 2,5,8,9-tetraaza-1-phosphabicyclo[3.3.3]undecane cation having formula (A)-1 are given below, but not limited thereto.

-continued
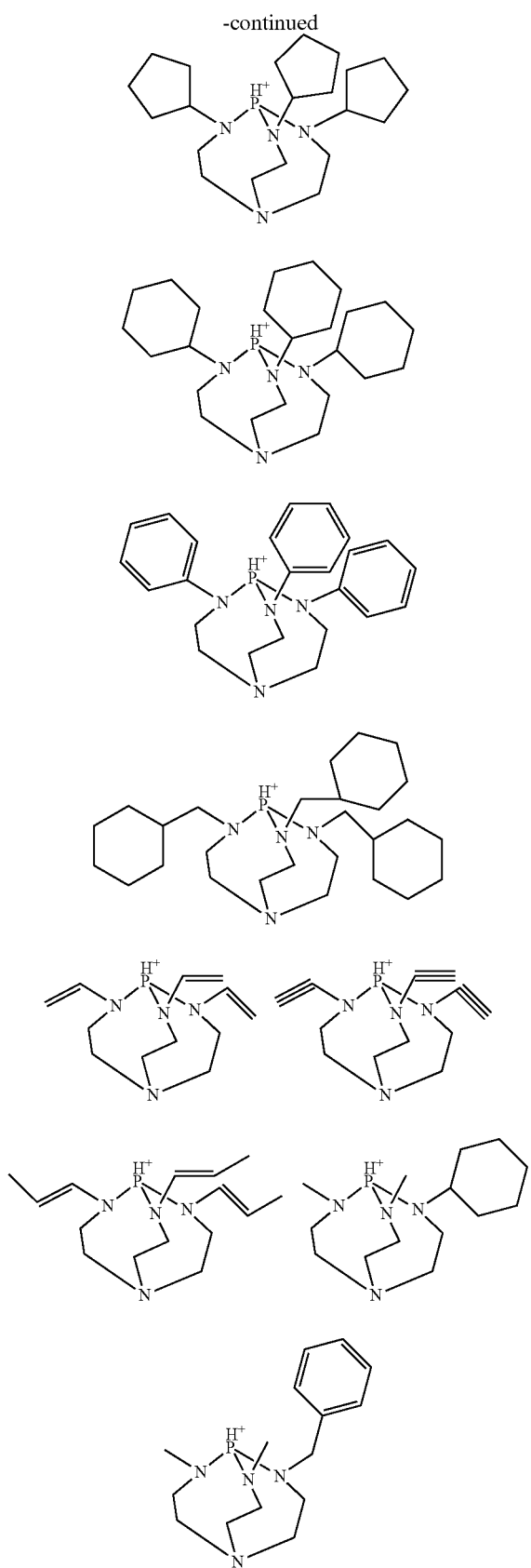
Examples of the biguanide cation having formula (A)-2 are given below, but not limited thereto.

-continued
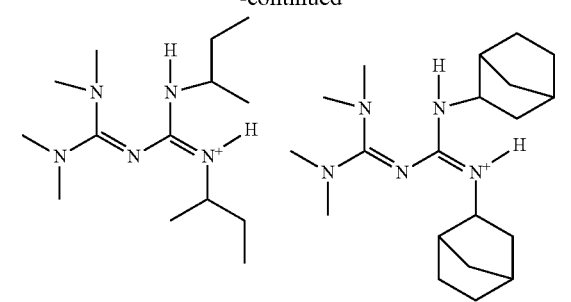
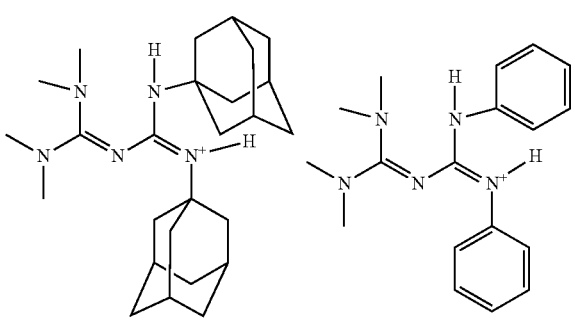
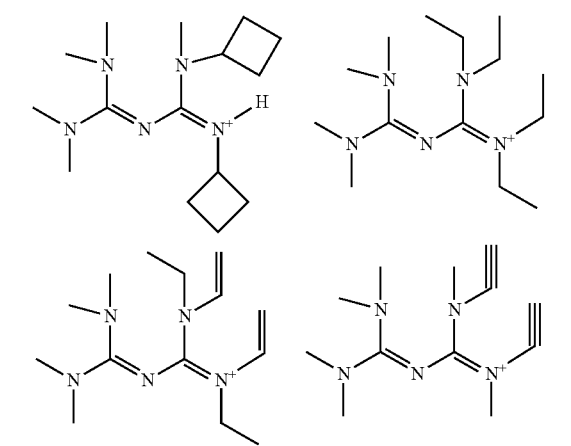
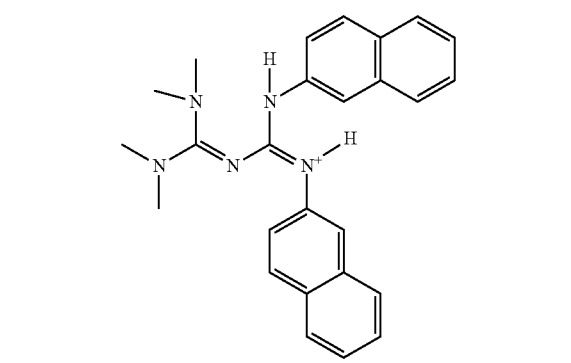
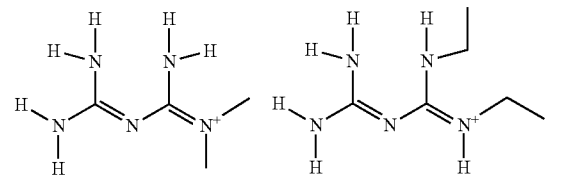
-continued
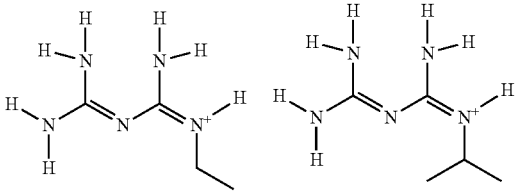
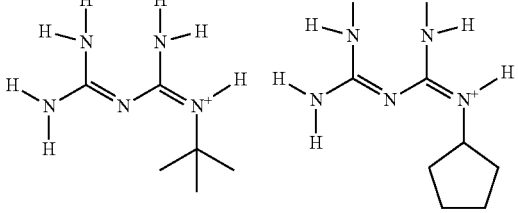
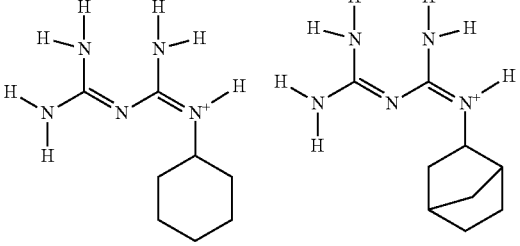
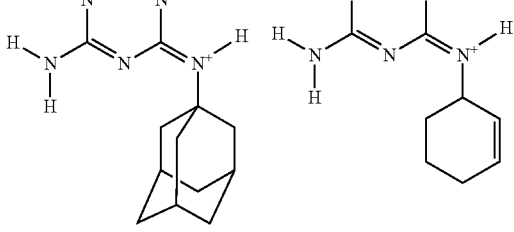
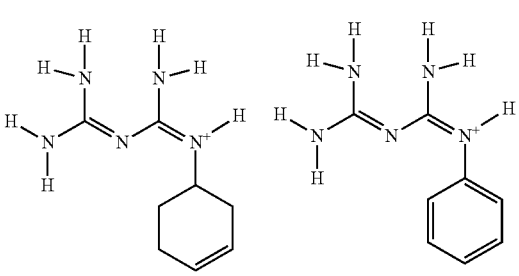
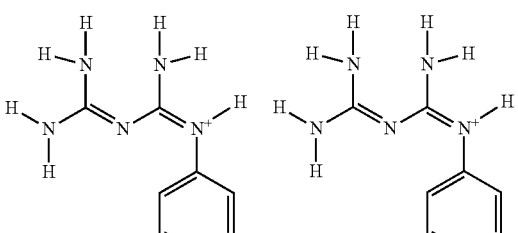

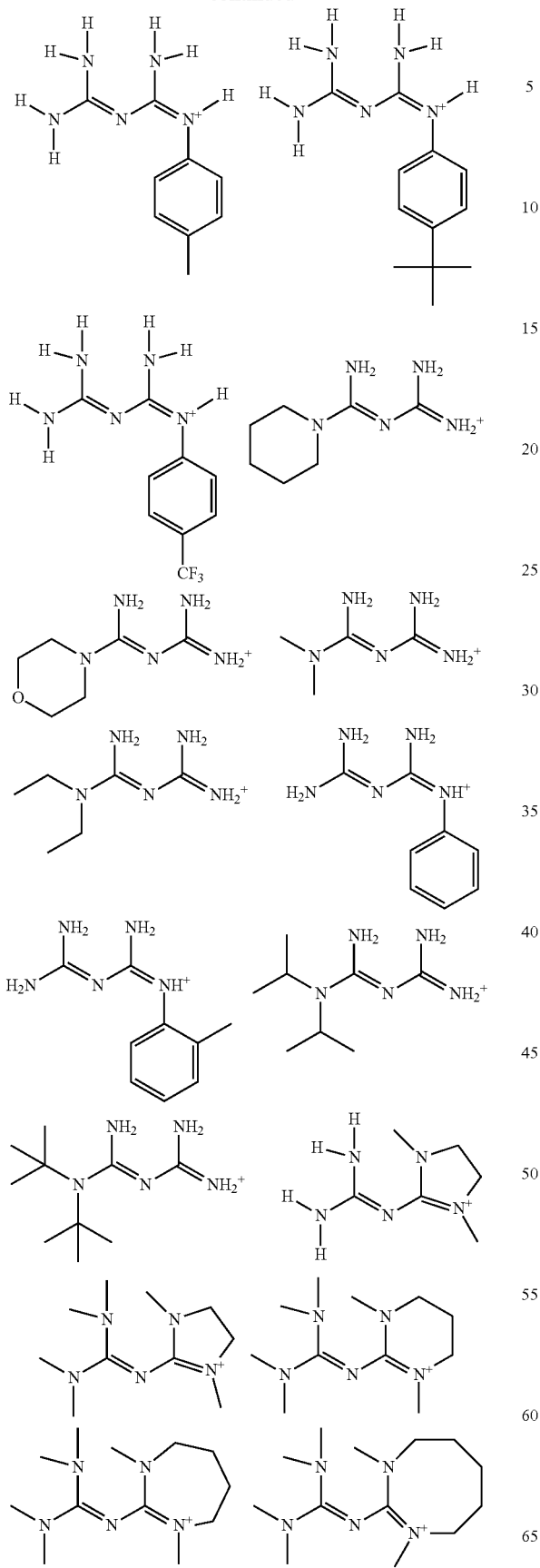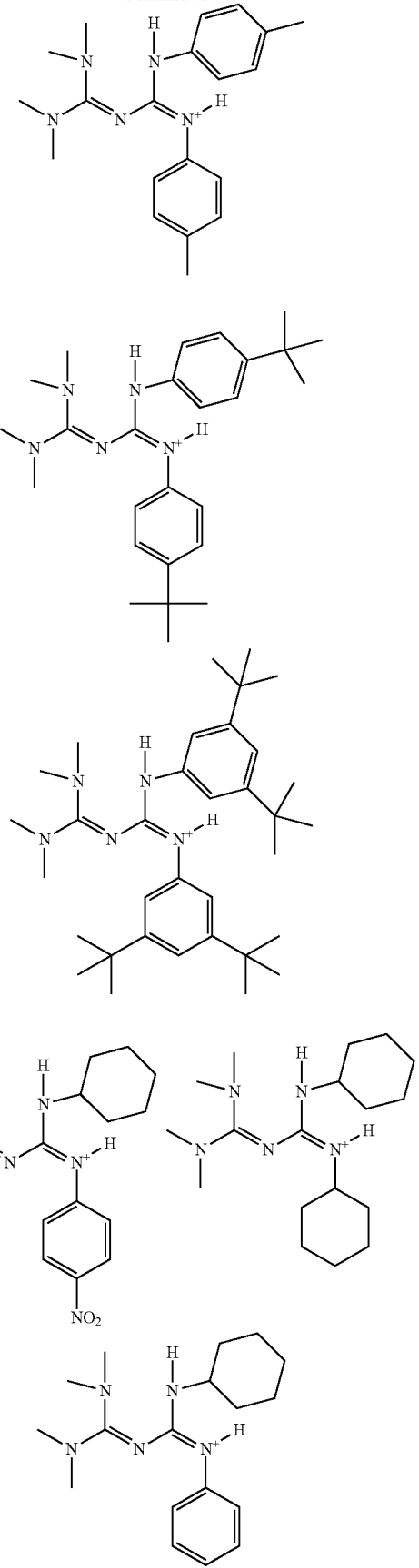

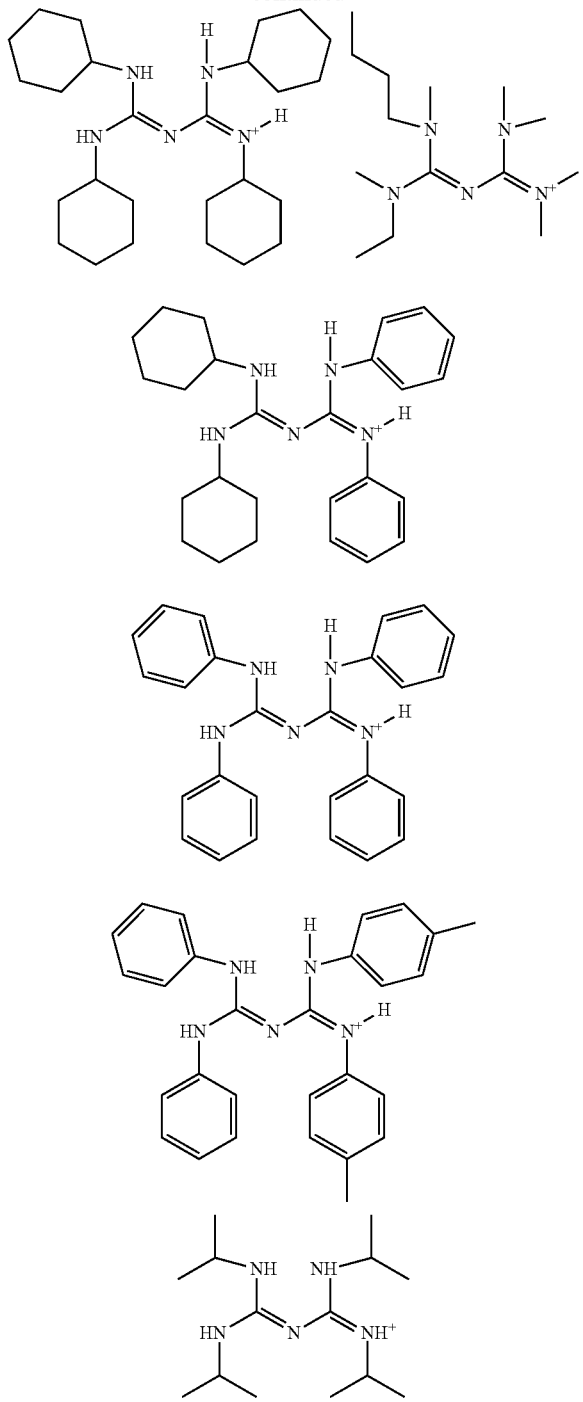
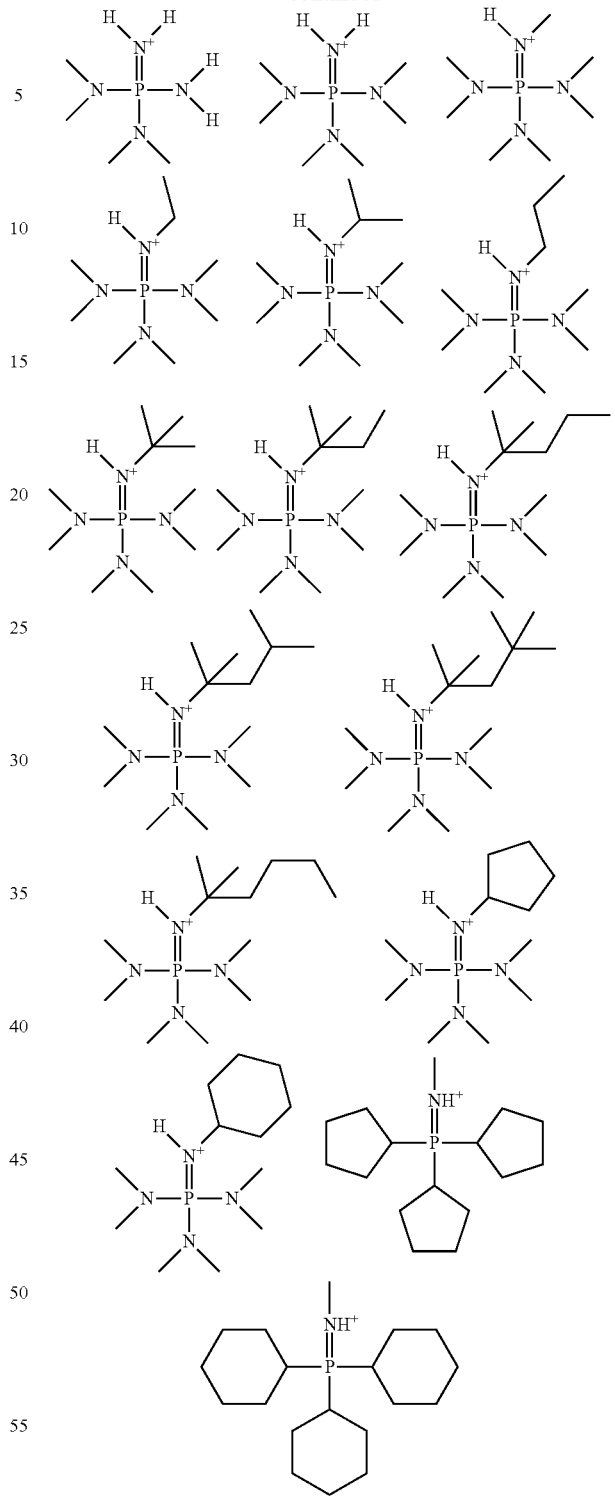
Examples of the phosphazene cation having formula (A)-3 are given below, but not limited thereto.
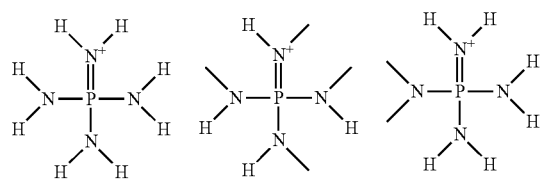
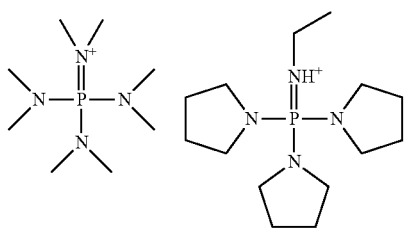

25
-continued
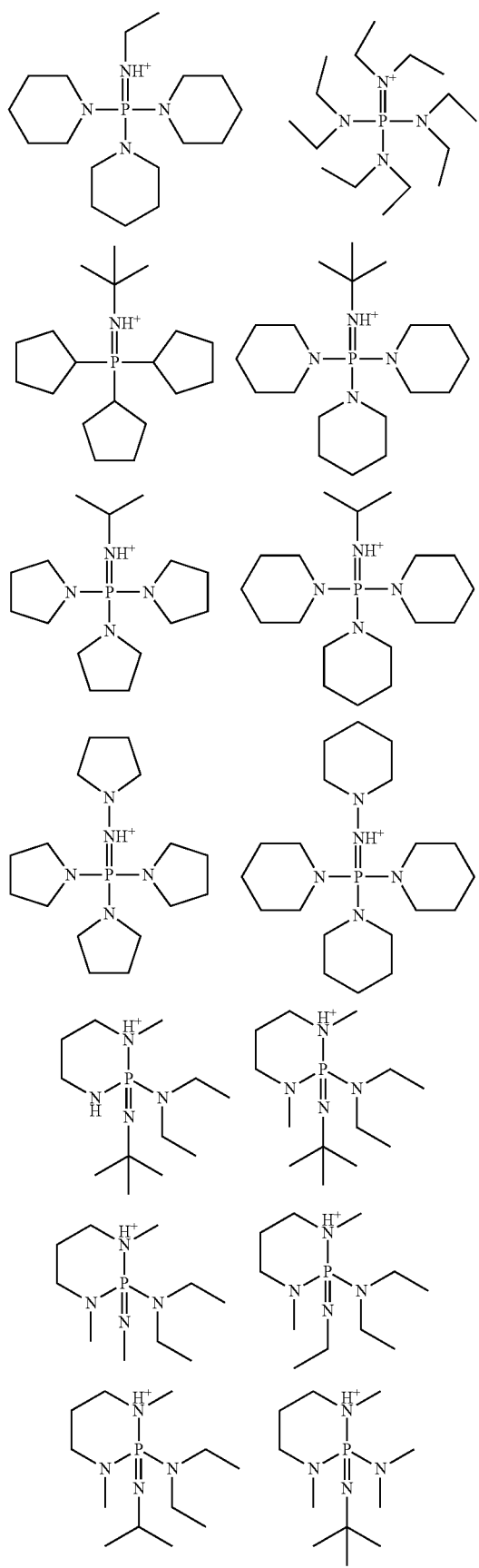
26
-continued
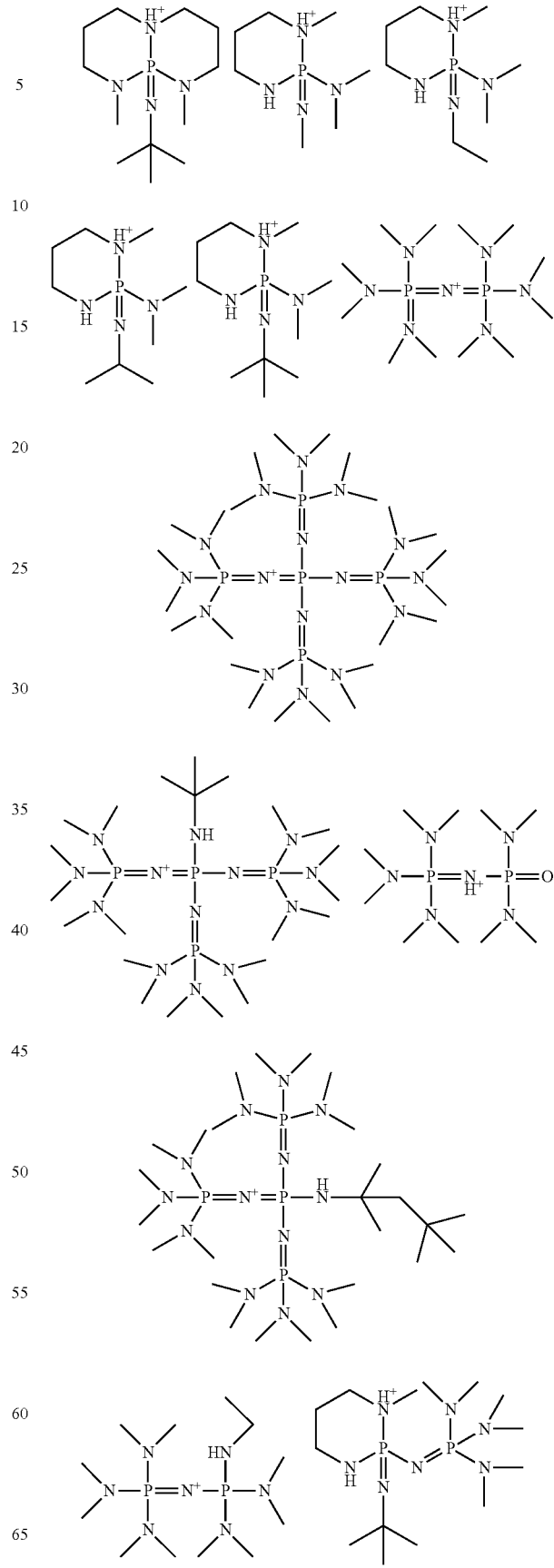

-continued

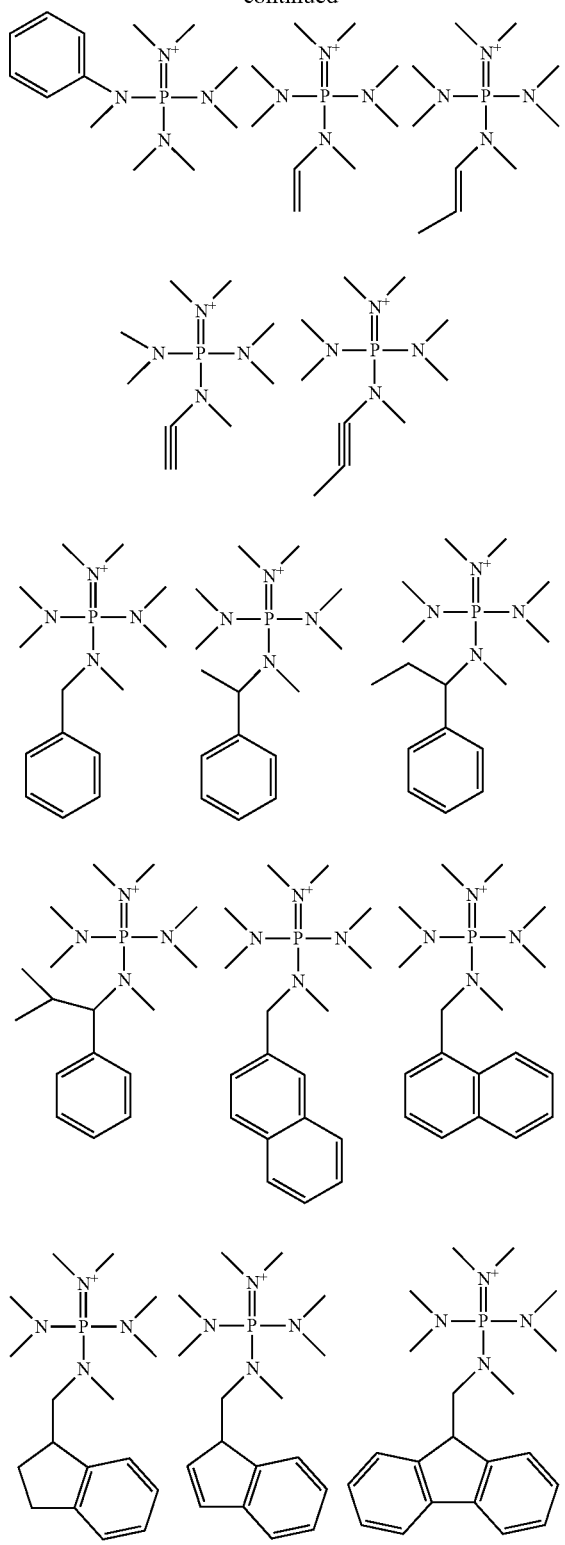

In the cationic organic base, positive charges are delocalized among plural nitrogen atoms. Therefore, points of trapping the anion of sulfonic acid, sulfonimide or sulfonmethide for neutralization are distributed everywhere. Thus the anion is quickly trapped. The organic base is an effective quencher having a high basicity and a high trapping ability.

With respect to the synthesis of the iodinated aromatic carboxylic salt, the iodinated aromatic carboxylic salt having a cation of formula (A)-1 may be prepared by mixing a 2,5,8,9-tetraaza-1-phosphabicyclo[3.3.3]undecane compound with an iodinated aromatic group-containing carboxylic acid.

The iodinated aromatic carboxylic salt having a cation of formula (A)-2 may be prepared by reacting a guanidine with a carbodiimide to form a biguanide compound and mixing the biguanide compound with an iodinated aromatic group-containing carboxylic acid.

The iodinated aromatic carboxylic salt having a cation of formula (A)-3 may be prepared by mixing a phosphazene compound with an iodinated aromatic group-containing carboxylic acid.

Since the iodinated aromatic carboxylic salt contains iodine in the molecule, it has substantial EUV absorption. Upon EUV exposure, it generates secondary electrons, followed by energy transfer to an acid generator, leading to sensitization. This leads to a high sensitivity and low acid diffusion, achieving improvements in both factors of LWR or CDU and sensitivity.

In view of sensitivity and acid diffusion suppressing effect, the iodinated aromatic carboxylic salt is preferably present in the resist composition in an amount of 0.001 to 50 parts, more preferably 0.01 to 20 parts by weight per 100 parts by weight of the base polymer to be described below.

Base Polymer

In the case of a positive resist composition, the base polymer in the resist composition is a polymer comprising acid labile group-containing recurring units. The acid labile group-containing recurring units are preferably recurring units having the formula (a1) or recurring units having the formula (a2). Sometimes these recurring units are simply referred to as recurring units (a1) and (a2).

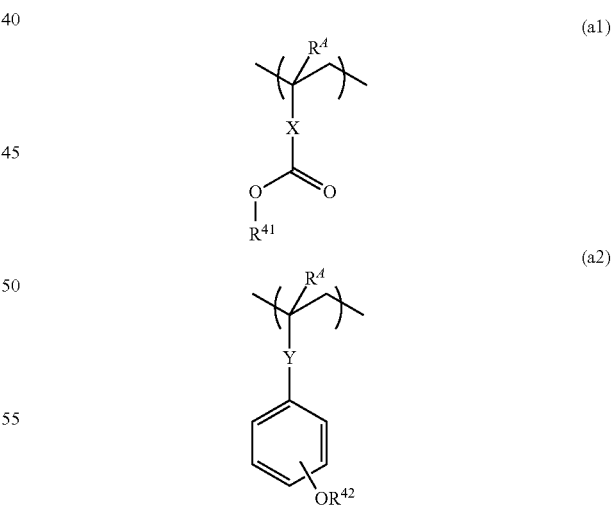

Herein $R^A$ is each independently hydrogen or methyl. $R^{41}$ and $R^{42}$ are each independently an acid labile group. X is a single bond, phenylone, naphthylene, or a $C_1$-$C_{12}$ linking group containing ester moiety or lactone ring. Y is a single bond or ester group.

Examples of the recurring units (a1) are shown below, but not limited thereto. Herein $R^A$ and $R^{41}$ are as defined above.

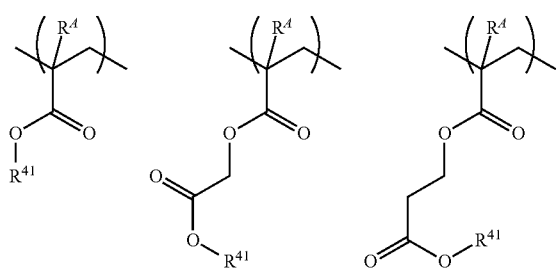
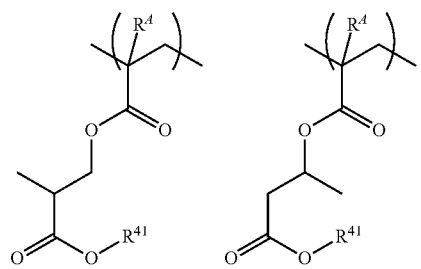
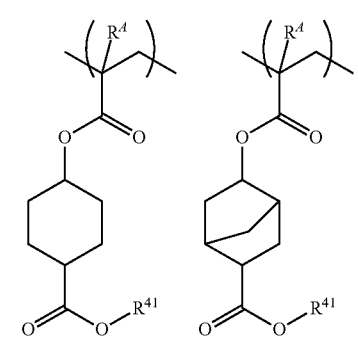
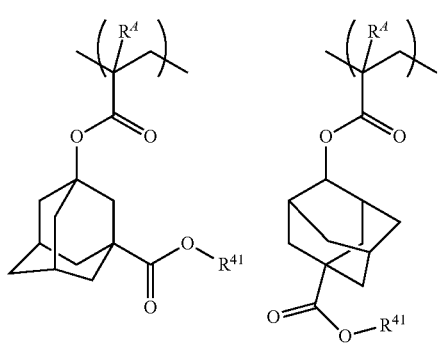
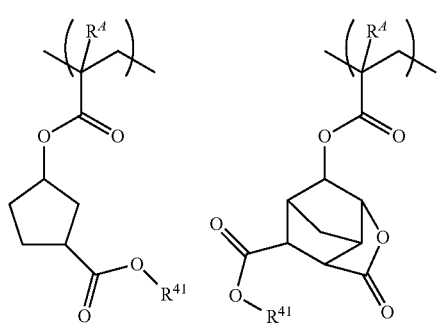

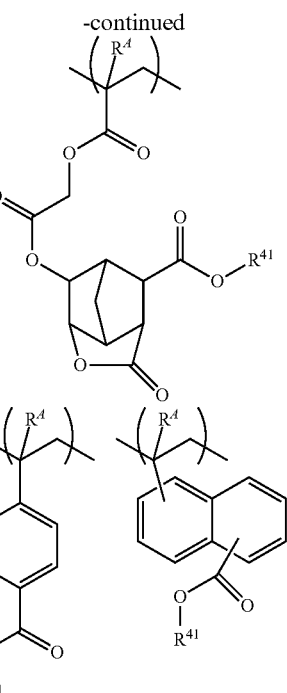

The acid labile groups represented by $R^{41}$ and $R^{42}$ in the recurring units (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

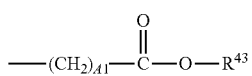 (AL-1)

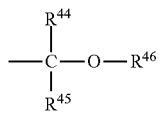 (AL-2)

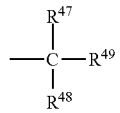 (AL-3)

In formulae (AL-1) and (AL-2), $R^{43}$ and $R^{46}$ are each independently a monovalent hydrocarbon group of 1 to 40 carbon atoms, preferably 1 to 20 carbon atoms, typically straight, branched or cyclic alkyl, which may contain a heteroatom such as oxygen, sulfur, nitrogen or fluorine. $R^{44}$ and $R^{45}$ are each independently hydrogen or a monovalent hydrocarbon group of 1 to 20 carbon atoms, typically straight, branched or cyclic alkyl, which may contain a heteroatom such as oxygen, sulfur, nitrogen or fluorine. A1 is an integer of 0 to 10, especially 1 to 5. A pair of $R^{44}$ and $R^{45}$, $R^{44}$ and $R^{46}$, or $R^{45}$ and $R^{46}$ may bond together to form a ring, typically alicyclic, with the carbon atom or carbon and oxygen atoms to which they are attached, the ring containing 3 to 20 carbon atoms, preferably 4 to 16 carbon atoms.

In formula (AL-3), $R^{47}$, $R^{48}$ and $R^{49}$ are each independently a monovalent hydrocarbon group of 1 to 20 carbon atoms, typically straight, branched or cyclic alkyl, which may contain a heteroatom such as oxygen, sulfur, nitrogen or fluorine. A pair of $R^{47}$ and $R^{48}$, $R^{47}$ and $R^{49}$, or $R^{48}$ and $R^{49}$ may bond together to form a ring, typically alicyclic, with the carbon atom to which they are attached, the ring containing 3 to 20 carbon atoms, preferably 4 to 16 carbon atoms.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

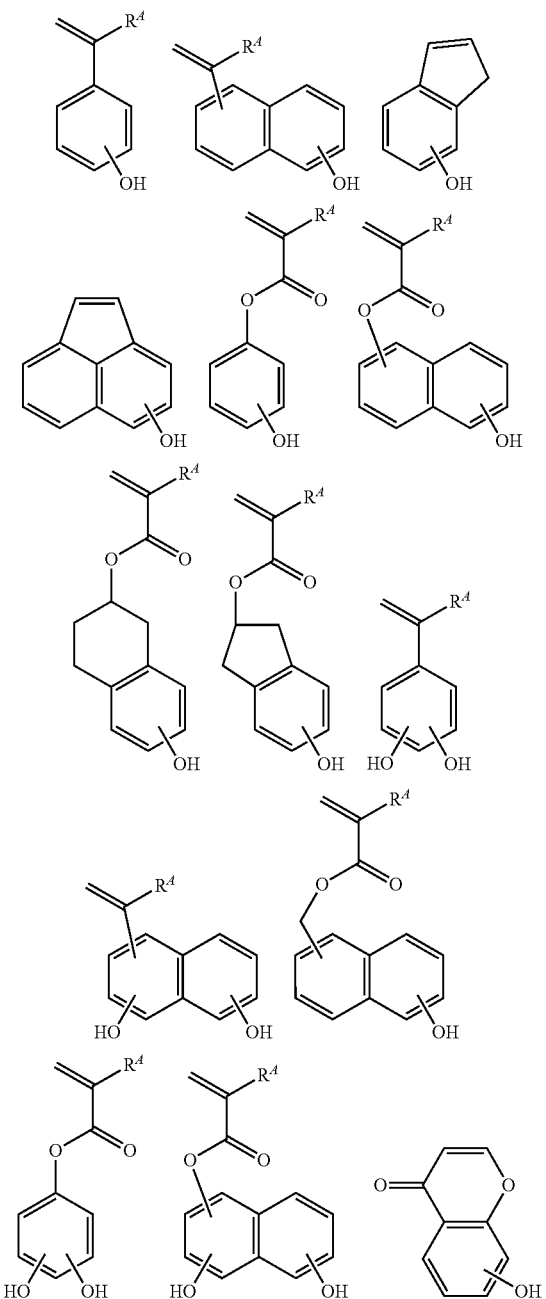

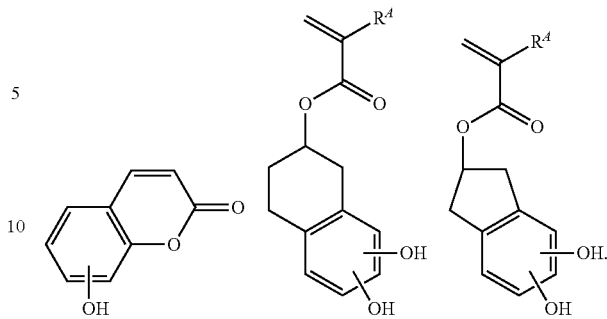

Further, recurring units (c) having another adhesive group selected from hydroxyl (other than the foregoing phenolic hydroxyl), lactone ring, ether, ester, carbonyl and cyano groups may also be incorporated in the base polymer. Examples of suitable monomers from which recurring units (c) are derived are given below, but not limited thereto. Herein $R^A$ is as defined above.

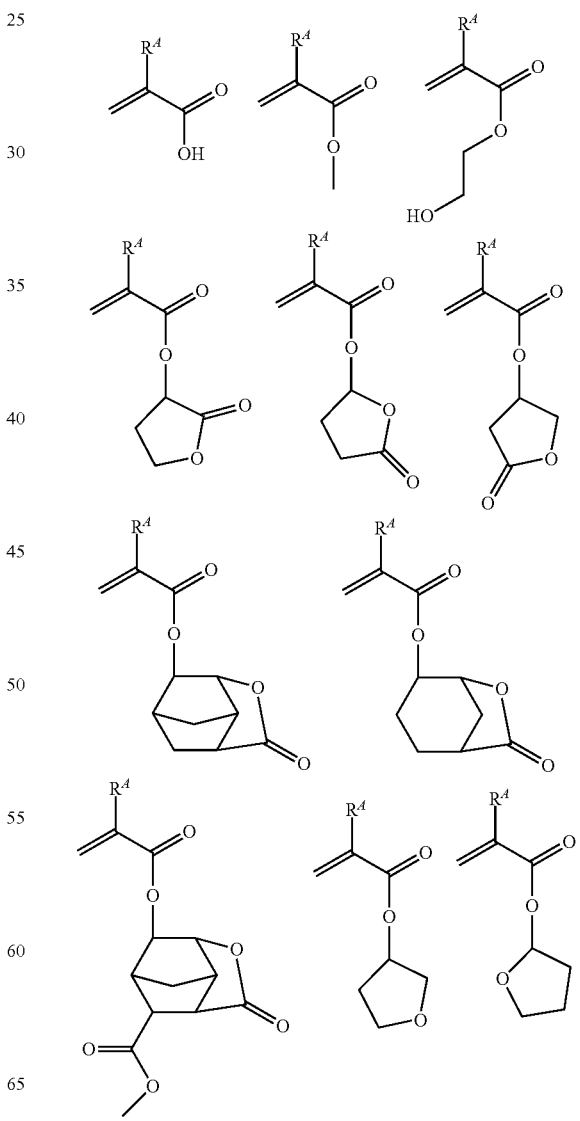

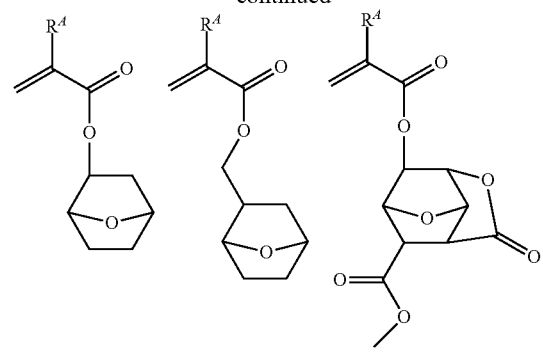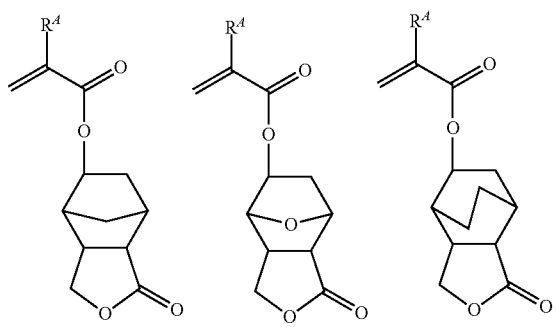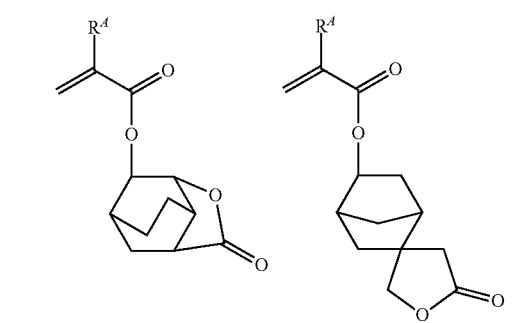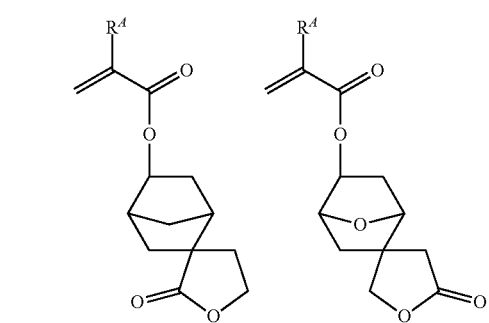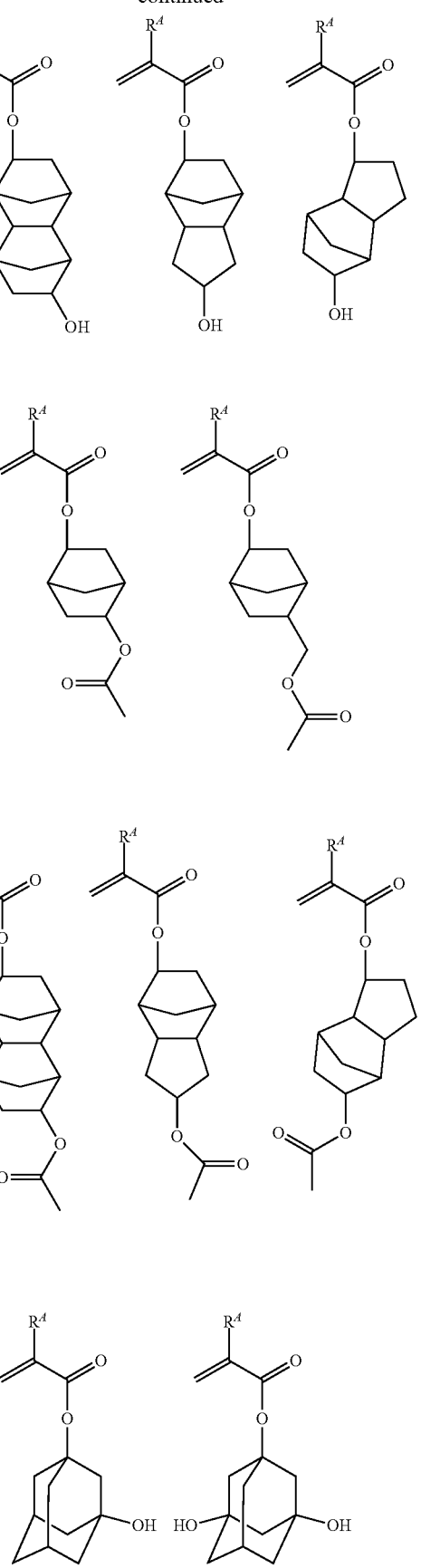

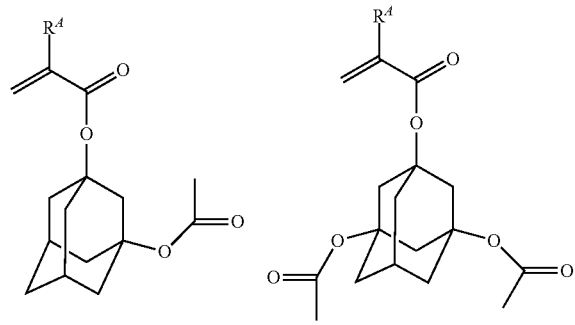
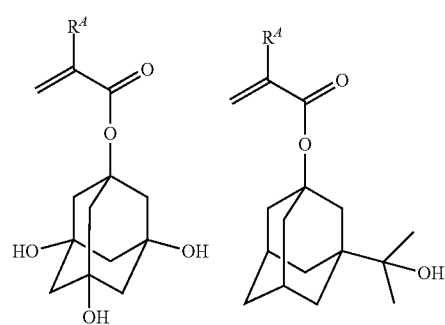
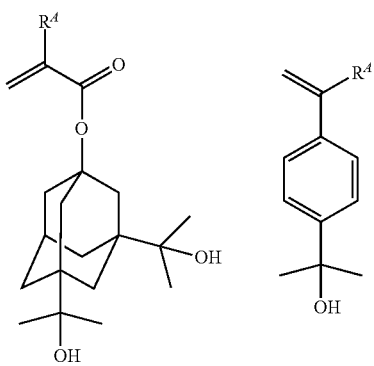
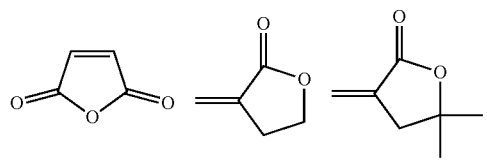
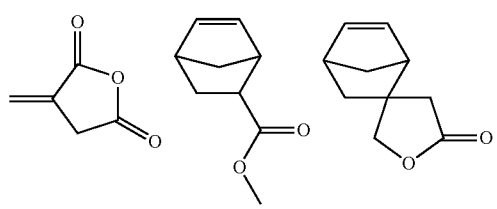
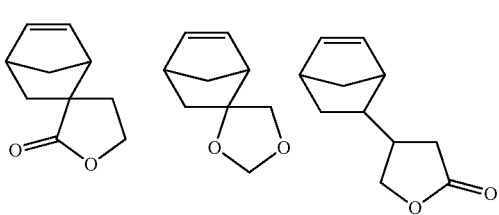
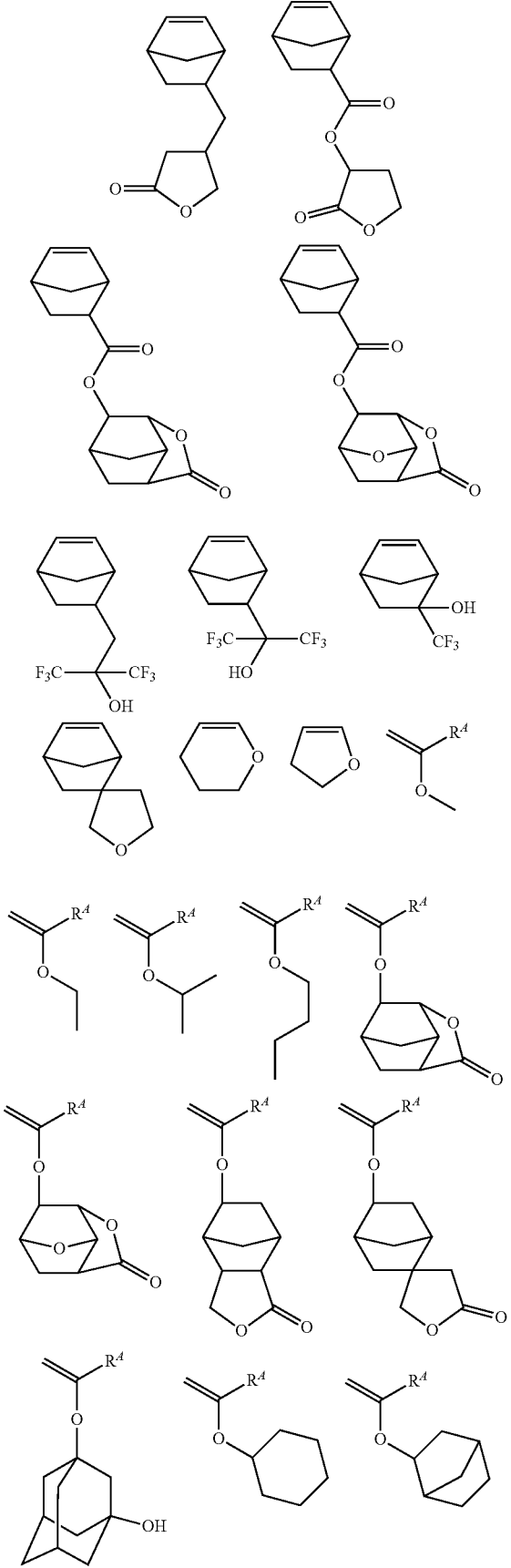

-continued
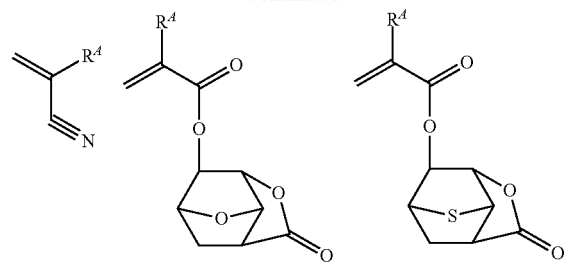
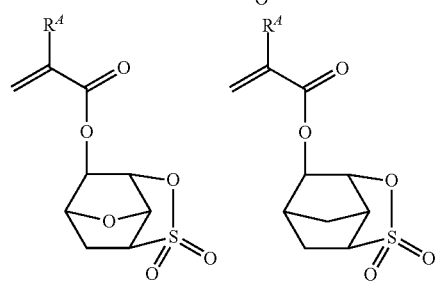
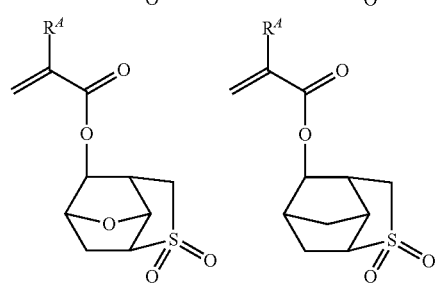
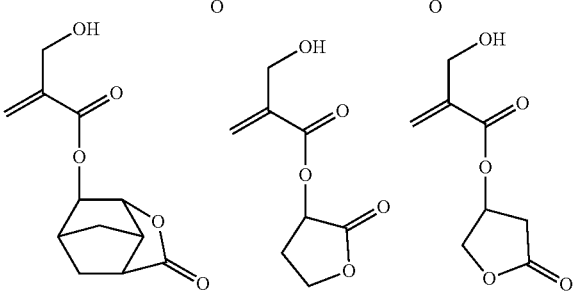
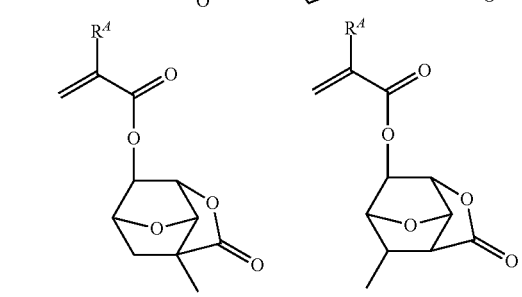
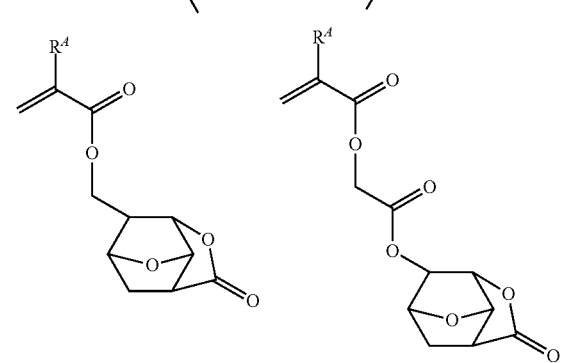
-continued
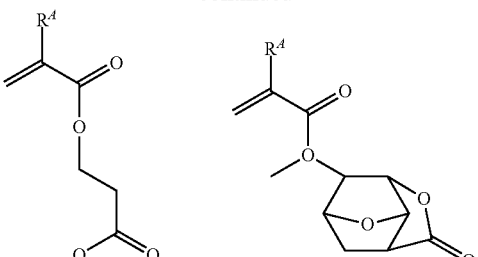
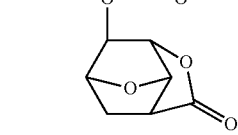
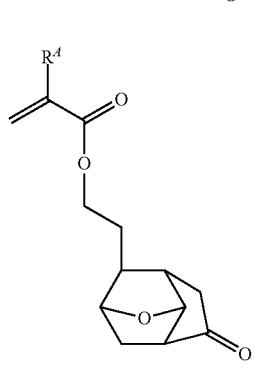
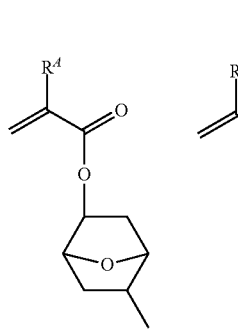
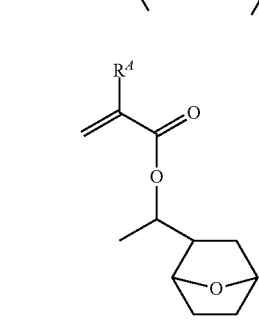
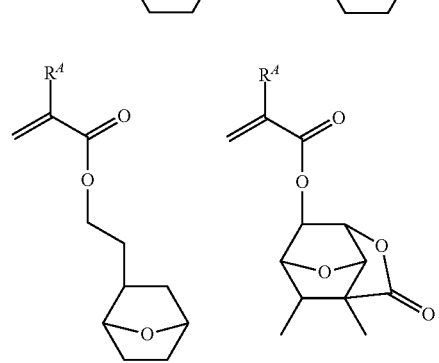

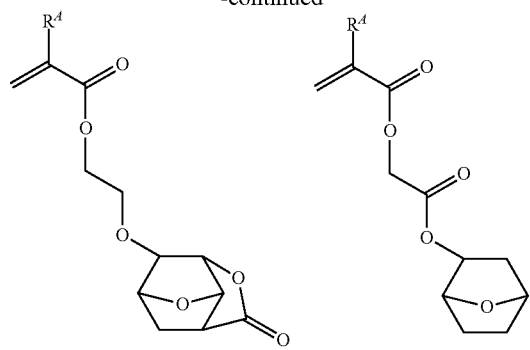
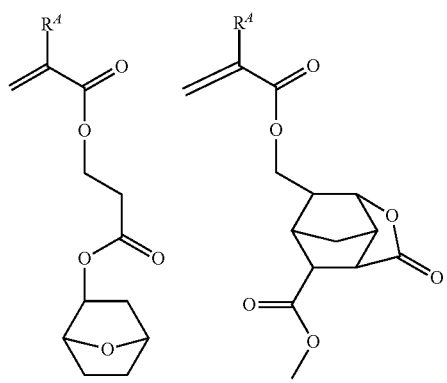
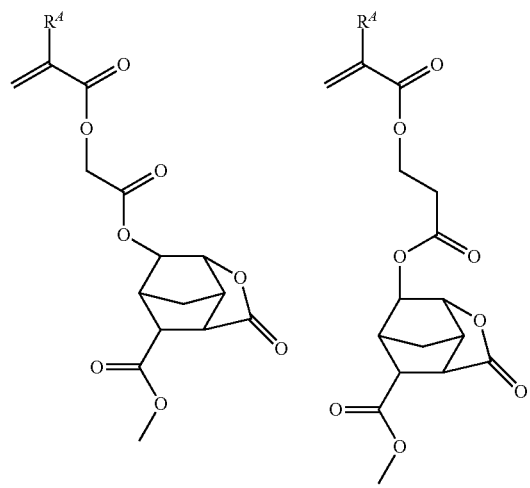
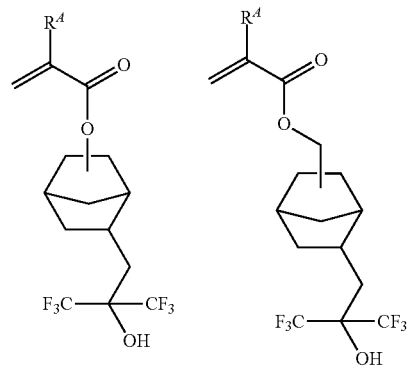
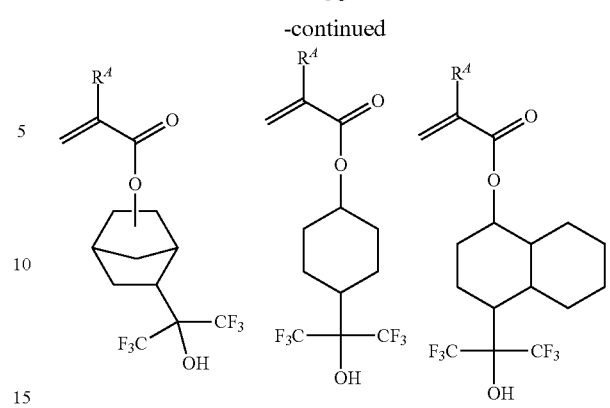
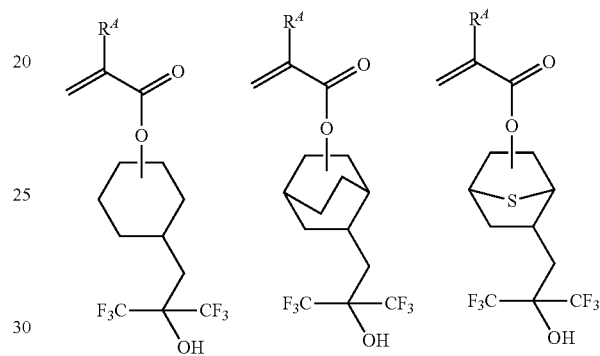
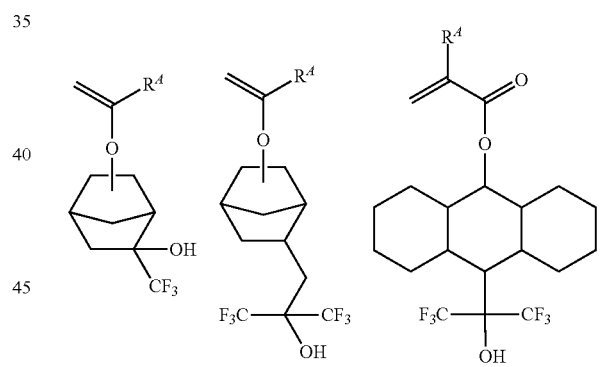
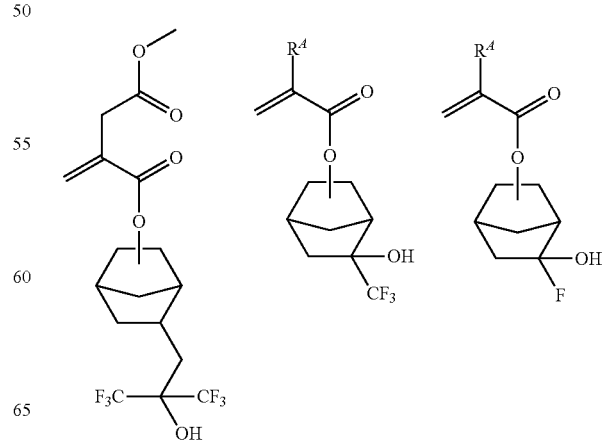

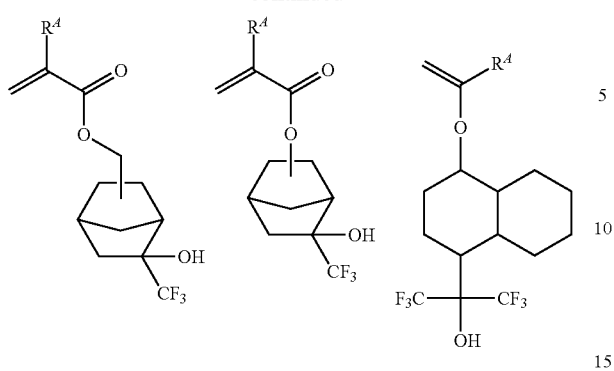
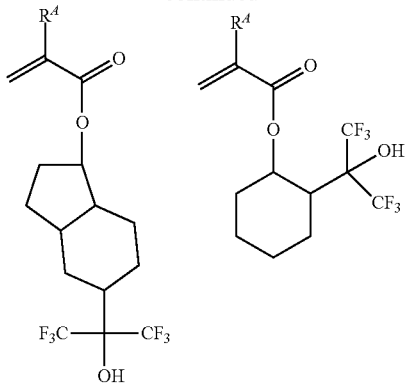
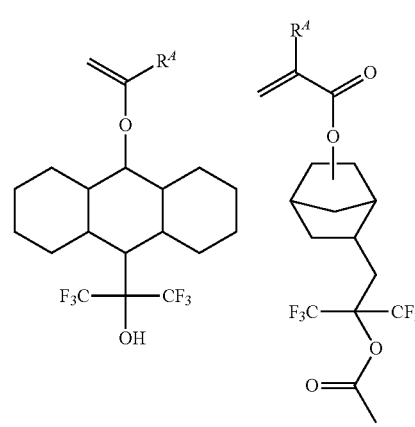
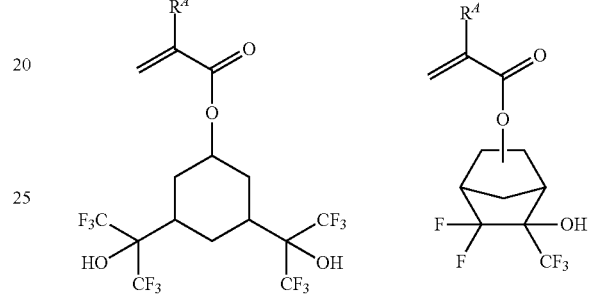
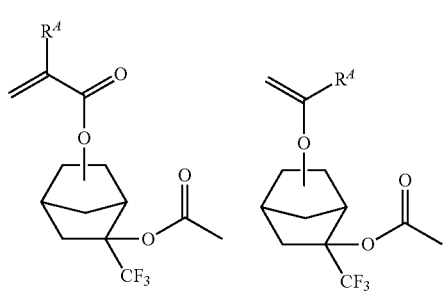
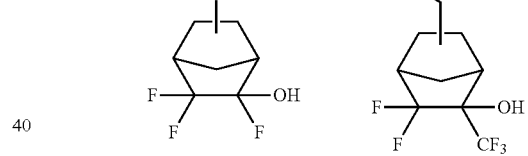
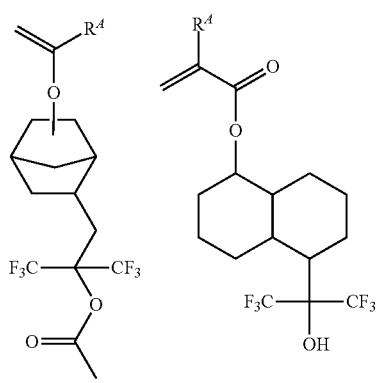
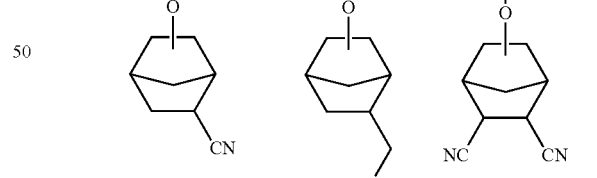
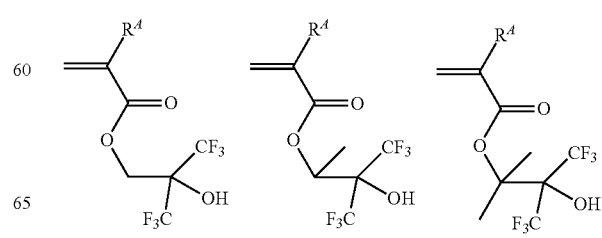

-continued
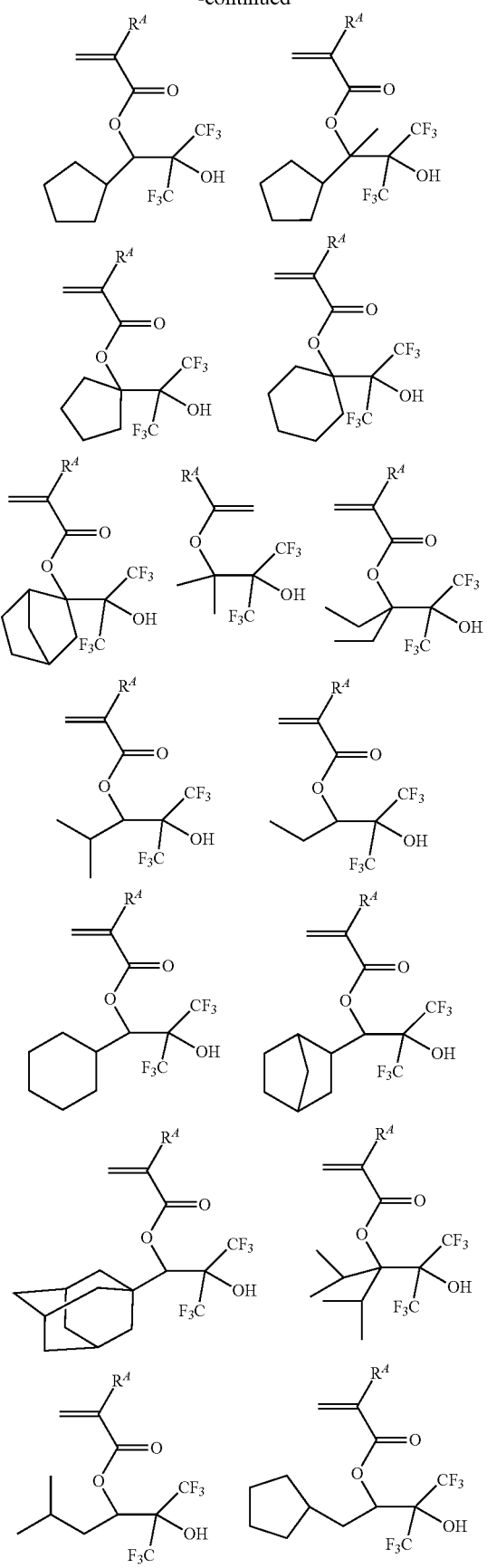
-continued
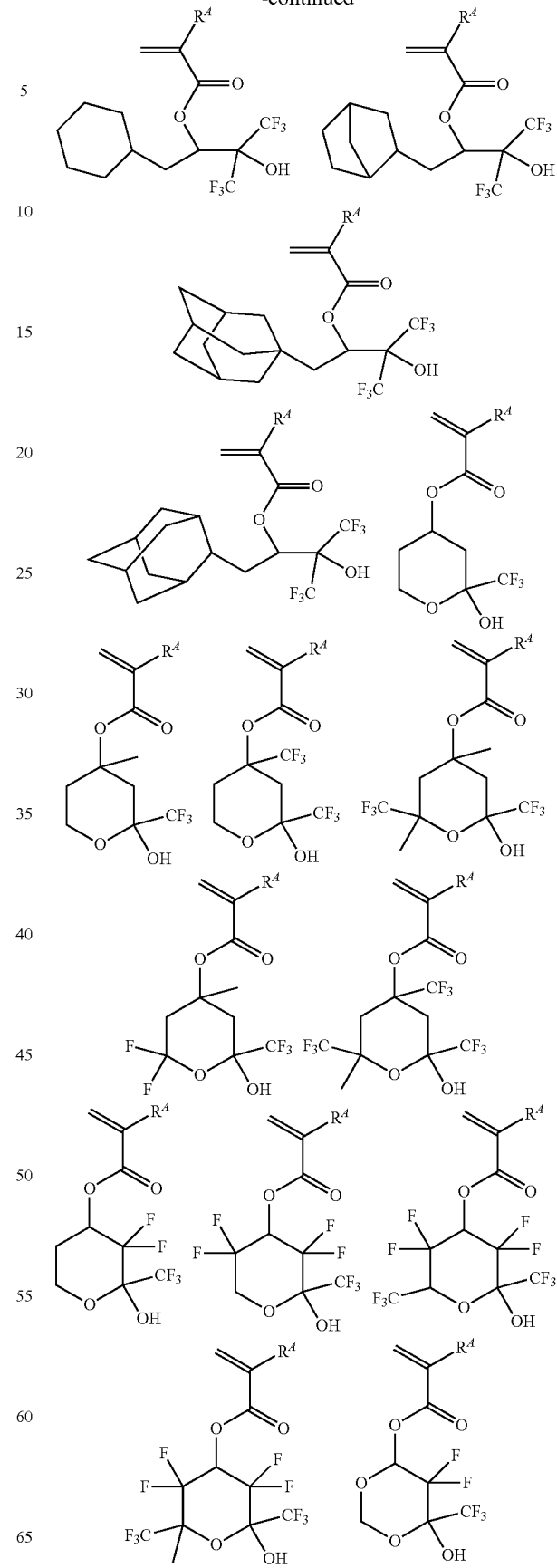

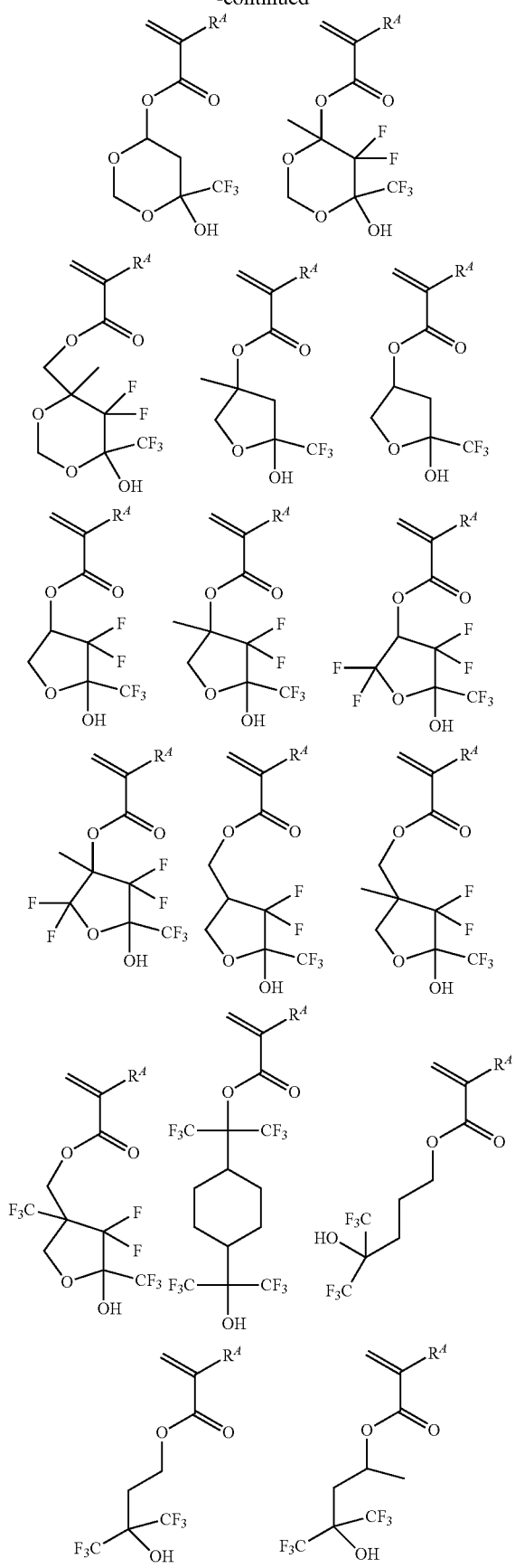

-continued
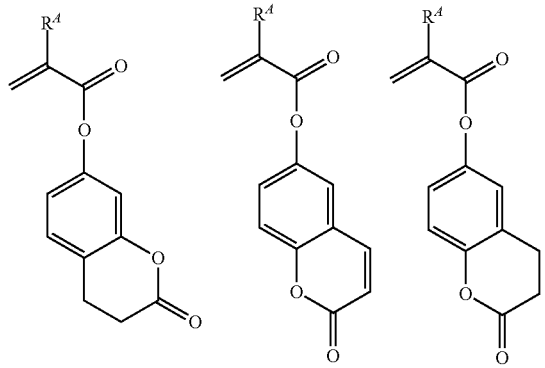
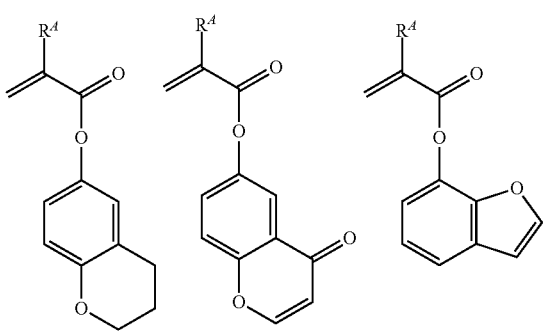
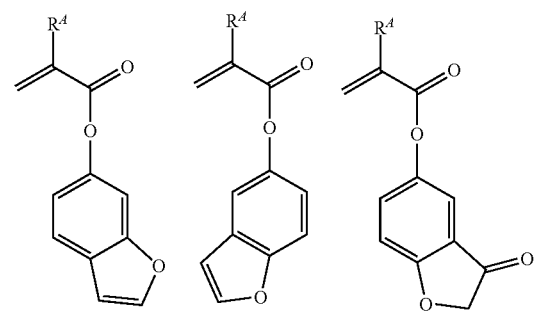
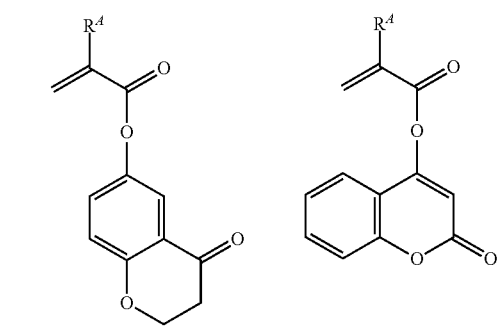
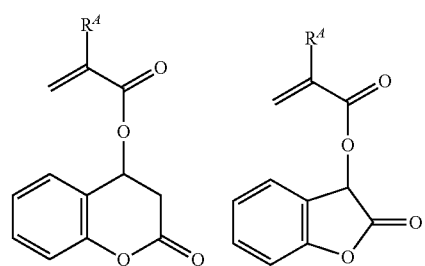
-continued
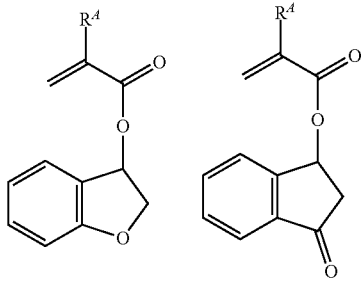
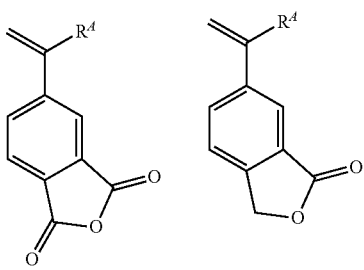
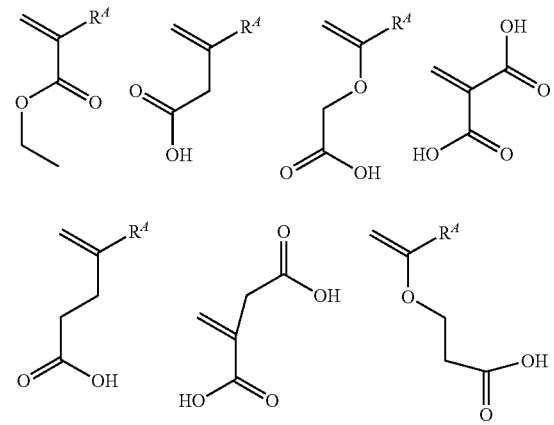
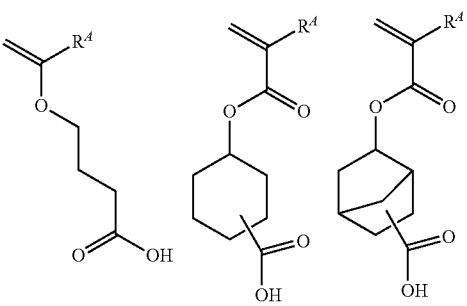

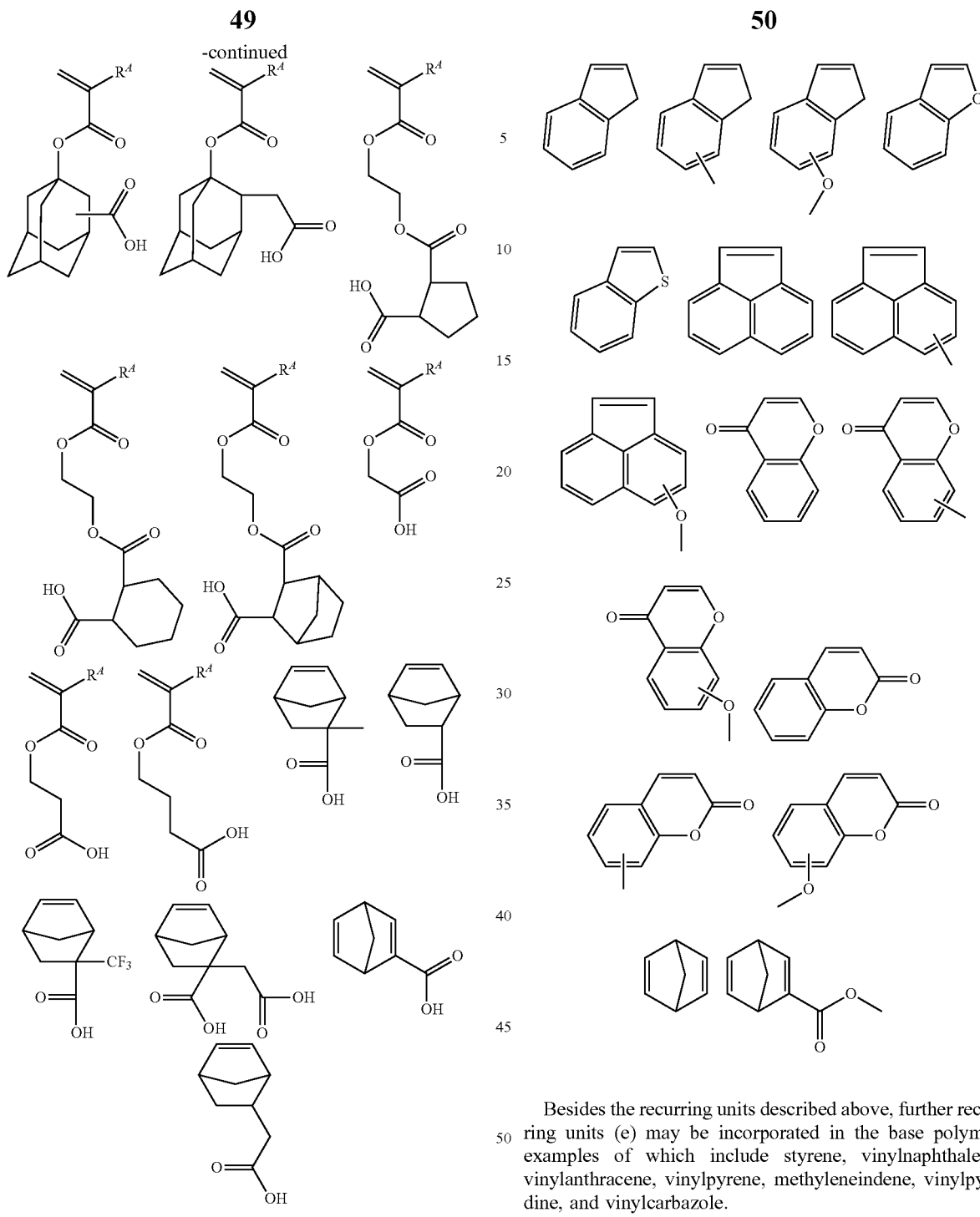

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.

Besides the recurring units described above, further recurring units (e) may be incorporated in the base polymer, examples of which include styrene, vinylnaphthalene, vinylanthracene, vinylpyrene, methyleneindene, vinylpyridine, and vinylcarbazole.

In a further embodiment, recurring units (f) derived from an onium salt having a polymerizable carbon-carbon double bond may be incorporated in the base polymer. JP-A 2005-084365 discloses sulfonium and iodonium salts having a polymerizable carbon-carbon double bond capable of generating a sulfonic acid. JP-A 2006-178317 discloses a sulfonium salt having sulfonic acid directly attached to the main chain.

The preferred recurring units (f) include recurring units having formula (f1), recurring units having formula (f2), and recurring units having formula (f3). These units are simply referred to as recurring units (f1), (f2) and (f3), which may be used alone or in combination of two or more types.

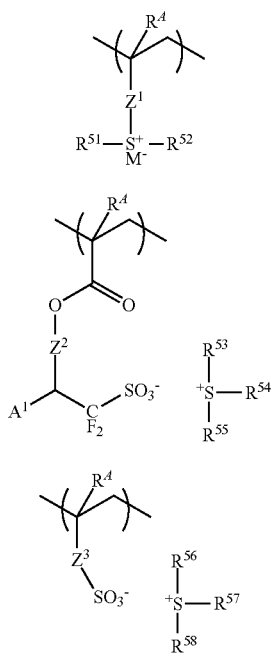

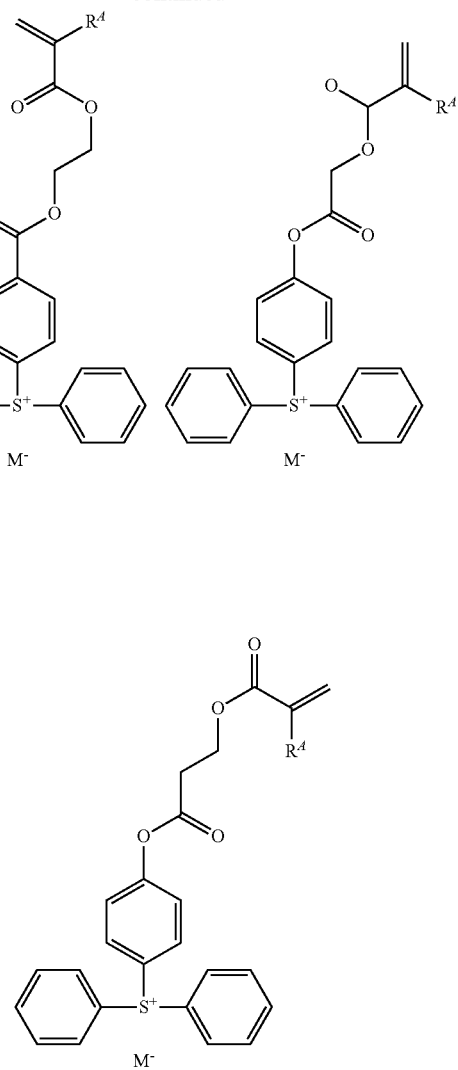

Herein $R^A$ is each independently hydrogen or methyl. $Z^1$ is a single bond, phenylene, —O—$Z^{11}$—, or —C(=O)—$Z^{12}$—$Z^{11}$—, wherein $Z^{11}$ is a straight, branched or cyclic $C_1$-$C_6$ alkylene group or straight, branched or cyclic $C_2$-$C_6$ alkenylene group which may contain a carbonyl, ester, ether or hydroxyl moiety, or phenylene group, $Z^{12}$ is —O— or —NH—. $R^{51}$, $R^{52}$, $R^{53}$, $R^{54}$, $R^{55}$, $R^{56}$, $R^{57}$, and $R^{58}$ are each independently a straight, branched or cyclic $C_1$-$C_{12}$ alkyl group which may contain a carbonyl, ester or ether moiety, or a $C_6$-$C_{12}$ aryl, $C_7$-$C_{20}$ aralkyl, or mercaptophenyl group. $Z^2$ is a single bond, —$Z^{21}$—C(=O)—O—, —$Z^{21}$—O—, or —$Z^{21}$—O—C(=O)—, wherein $Z^{21}$ is a straight, branched or cyclic $C_1$-$C_{12}$ alkylene group which may contain a carbonyl, eater or ether moiety. $Z^3$ is a single bond, methylene, ethylene, phenylene, fluorinated phenylene, —O—$Z^{31}$—, or —C(=O)—$Z^{32}$—$Z^{31}$—, wherein $Z^{31}$ is a straight, branched or cyclic $C_1$-$C_6$ alkylene group or straight, branched or cyclic $C_2$-$C_6$ alkenylene group which may contain a carbonyl, ester, ether or hydroxyl moiety, or a phenylene, fluorinated phenylene or trifluoromethyl-substituted phenylene group, $Z^{32}$ is —O— or —NH—. $A^1$ is hydrogen or trifluoromethyl. $M^-$ is a non-nucleophilic counter ion.

Examples of the monomer from which recurring unit (f1) is derived are shown below, but not limited thereto. $R^A$ and $M^-$ are as defined above.

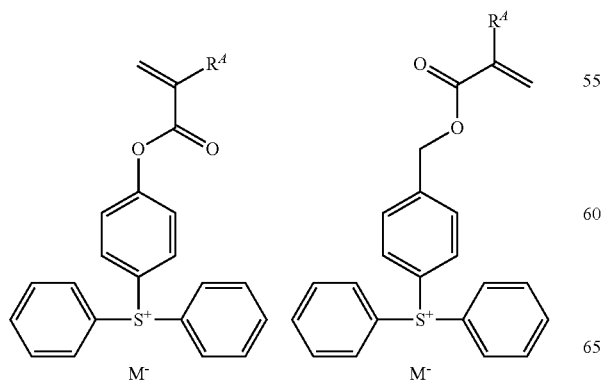

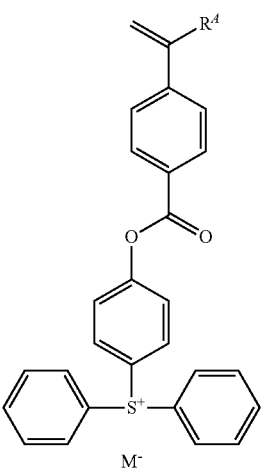

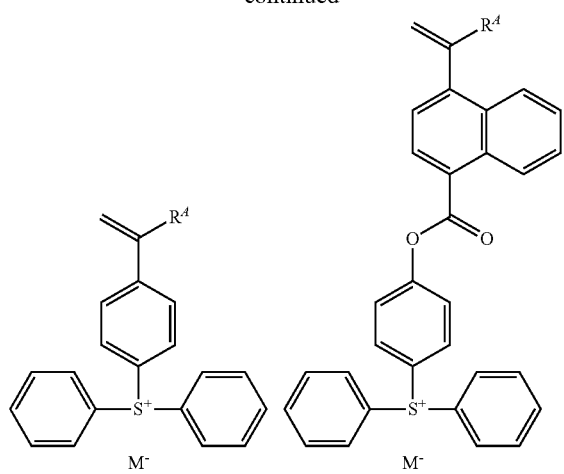
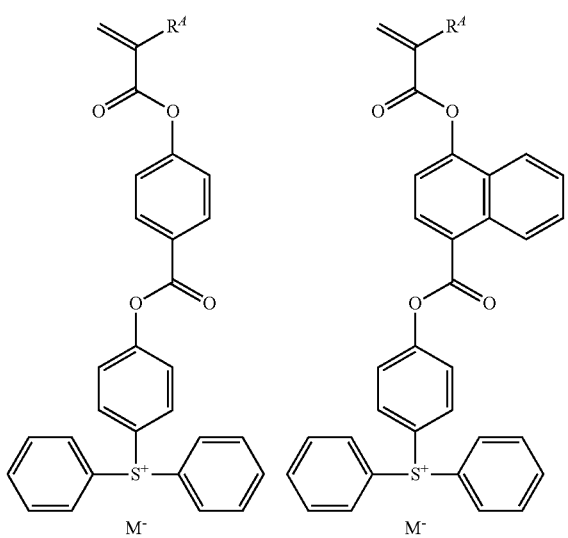
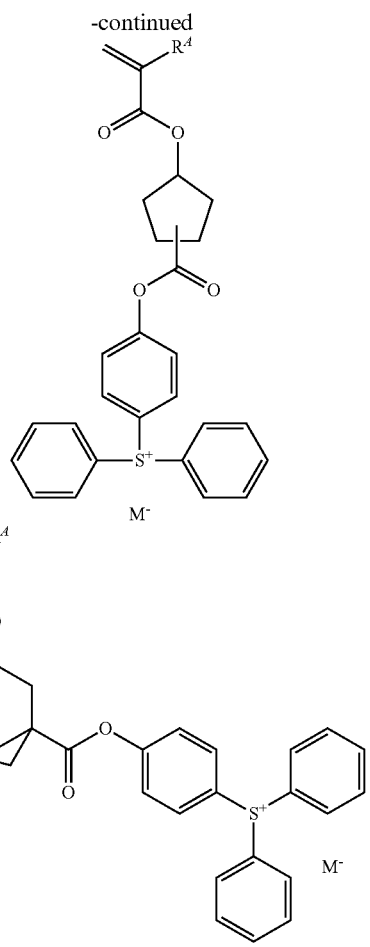
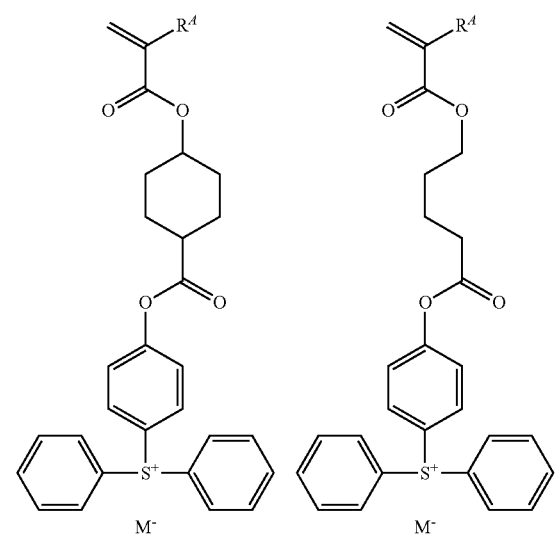

Examples of the non-nucleophilic counter ion M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; sulfonimides such as bis(trifluoromethylsulfonyl)imide, bis(perfluoroethylsulfonyl)imide and bis(perfluorobutylsulfonyl)imide; sulfonmethides such as tris(trifluoromethylsulfonyl)methide and tris(perfluoroethylsulfonyl)methide.

Also included are sulfonates having fluorine substituted at α-position as represented by the formula (K-1) and sulfonates having fluorine substituted at α- and β-positions as represented by the formula (K-2).

$$R^{61}-CF_2-SO_3^-  \quad \text{(K-1)}$$

$$\begin{array}{c} R^{62}-O \\ \phantom{xxx} \diagdown \\ \phantom{xxxxx} CF_2-SO_3^- \\ \phantom{xx} \diagup \\ F_3C \end{array} \quad \text{(K-2)}$$

In formula (K-1), $R^{61}$ is hydrogen, or a $C_1$-$C_{20}$ straight, branched or cyclic alkyl group, $C_2$-$C_{20}$ straight, branched or cyclic alkenyl group, or $C_6$-$C_{20}$ aryl group, which may contain an ether, ester, carbonyl moiety, lactone ring, or fluorine atom. In formula (K-2), $R^{62}$ is hydrogen, or a $C_1$-$C_{30}$ straight, branched or cyclic alkyl group, $C_2$-$C_{30}$ straight, branched or cyclic acyl group, $C_2$-$C_{20}$ straight, branched or cyclic alkenyl group, $C_6$-$C_{20}$ aryl group or $C_6$-$C_{20}$ aryloxy group, which may contain an ether, ester, carbonyl moiety or lactone ring.

Examples of the monomer from which recurring unit (f2) is derived are shown below, but not limited thereto. $R^A$ is as defined above.

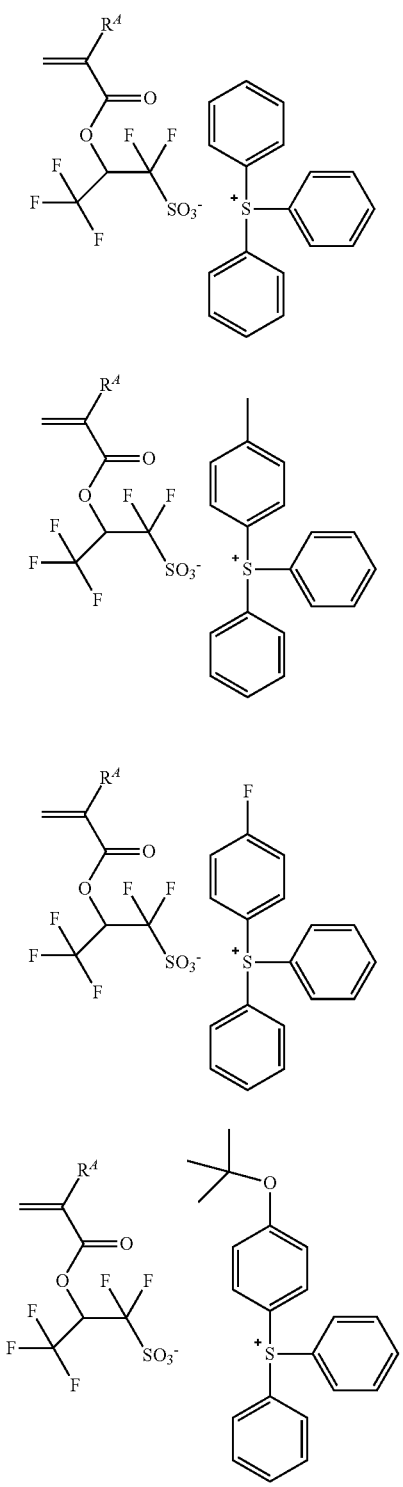

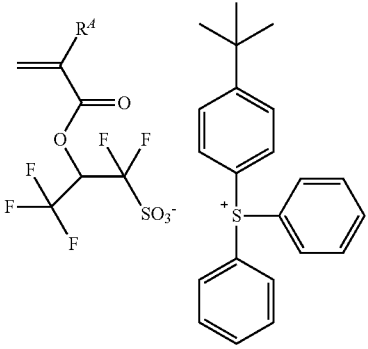

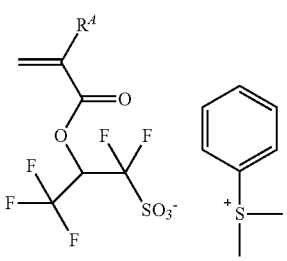

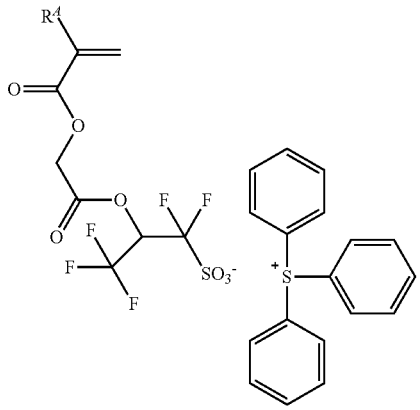

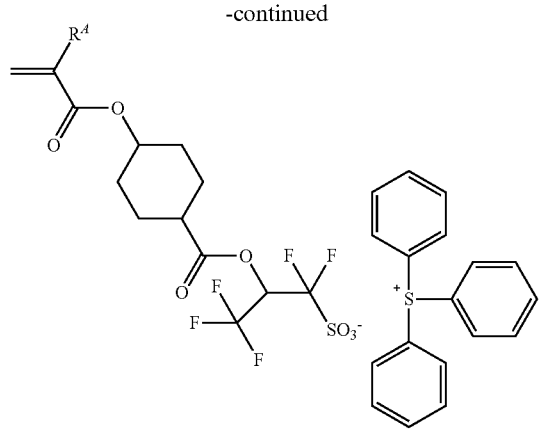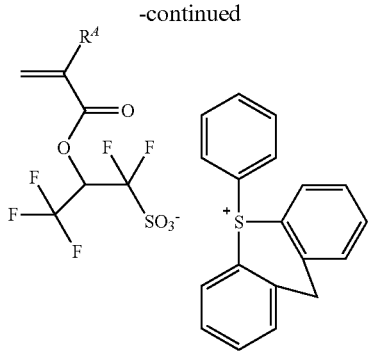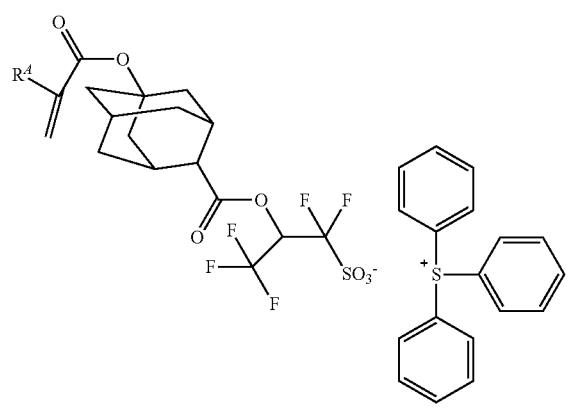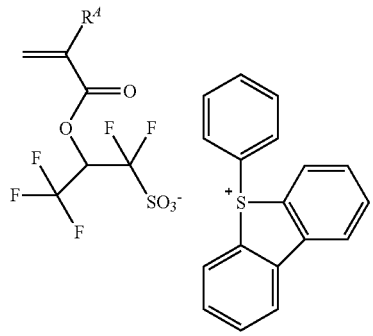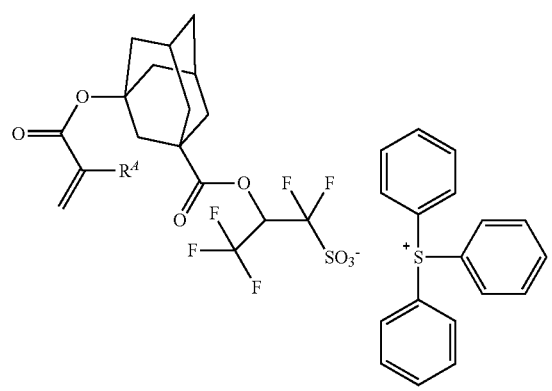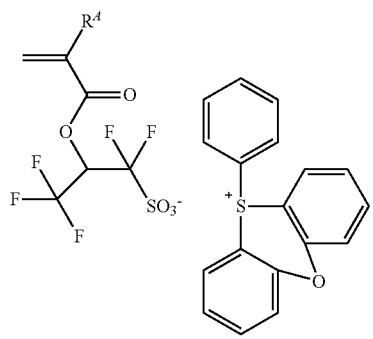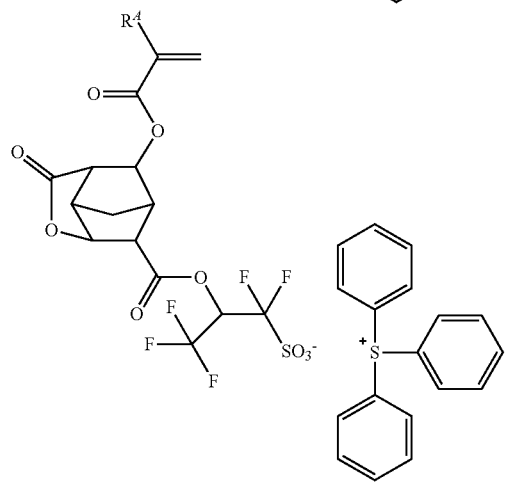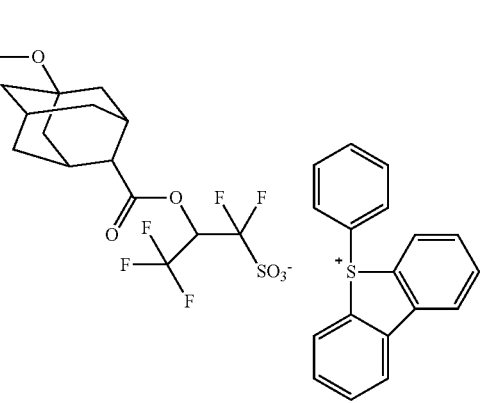

-continued
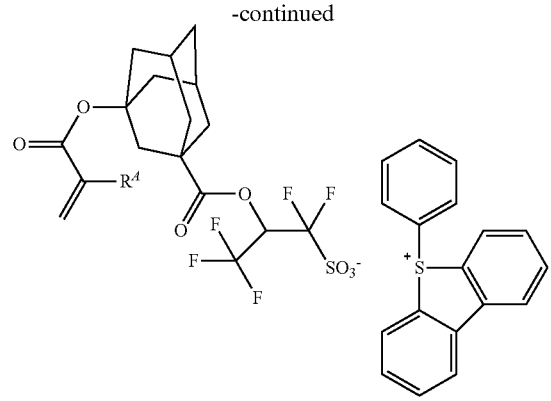
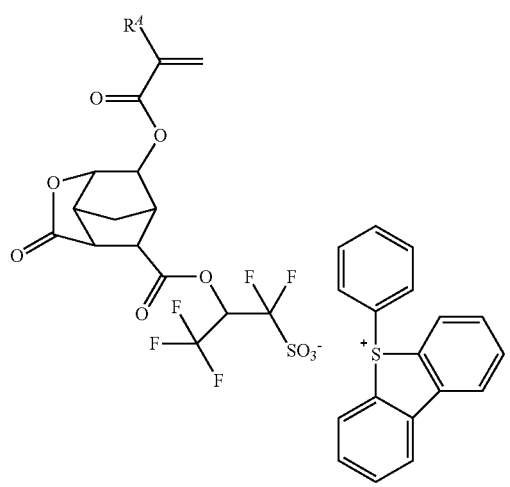
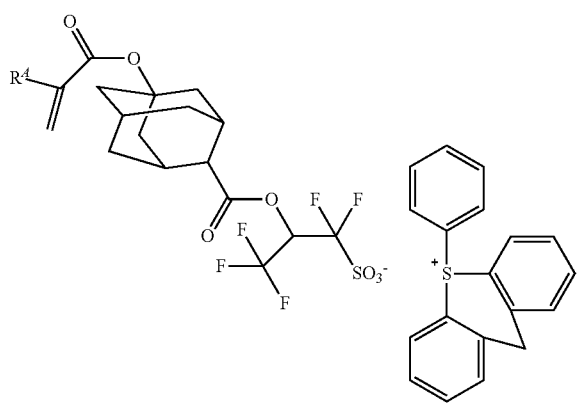
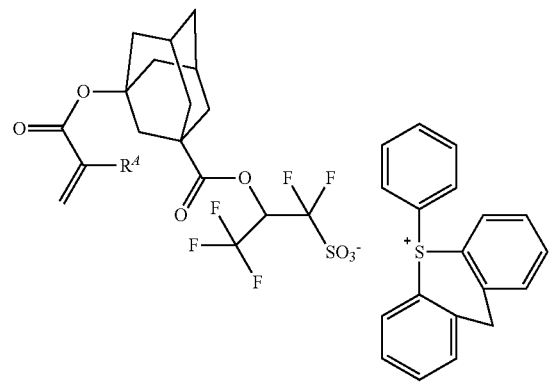
-continued
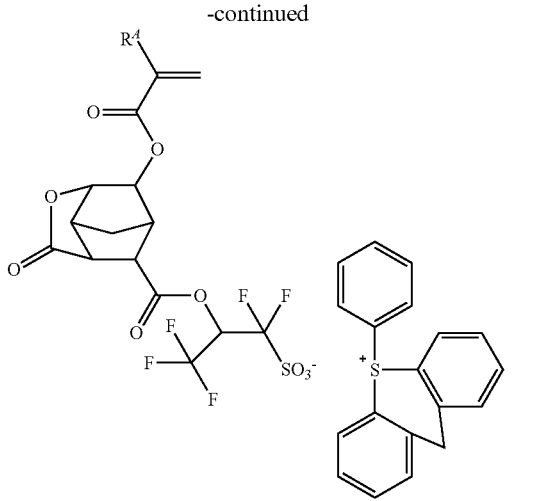
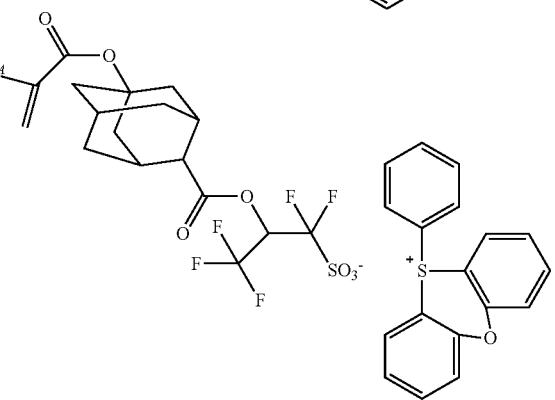
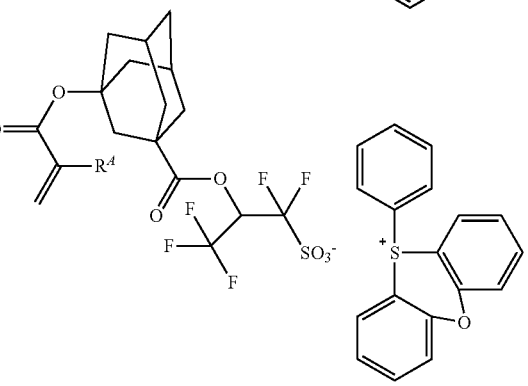
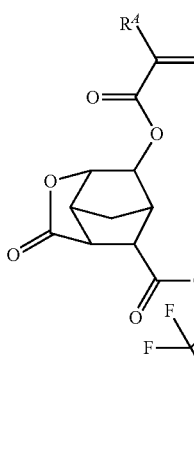

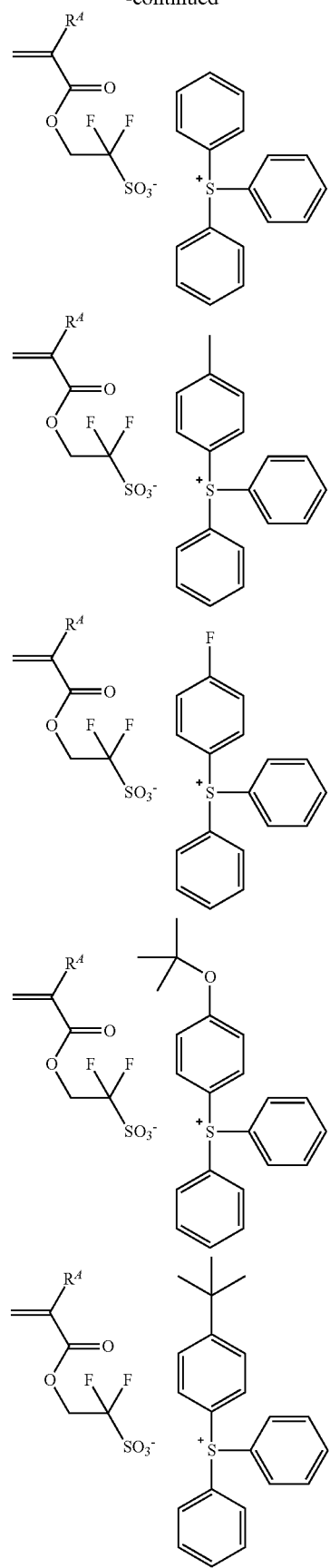

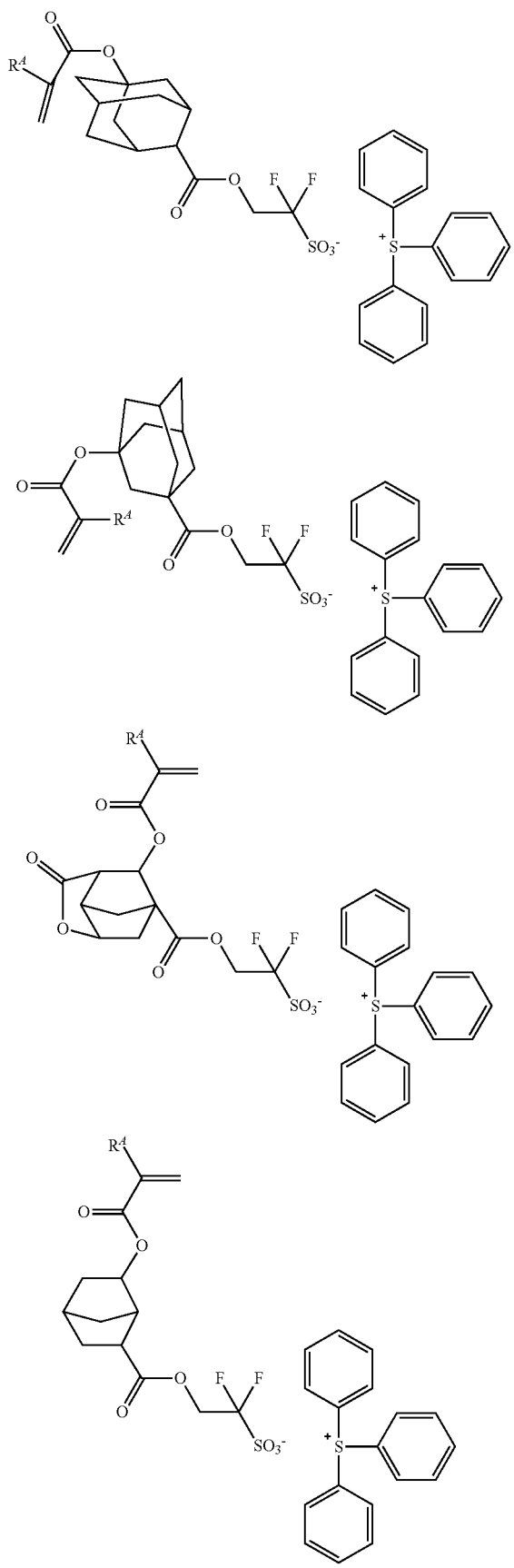
Examples of the monomer from which recurring unit (f3) is derived are shown below, but not limited thereto. R^A is as defined above.
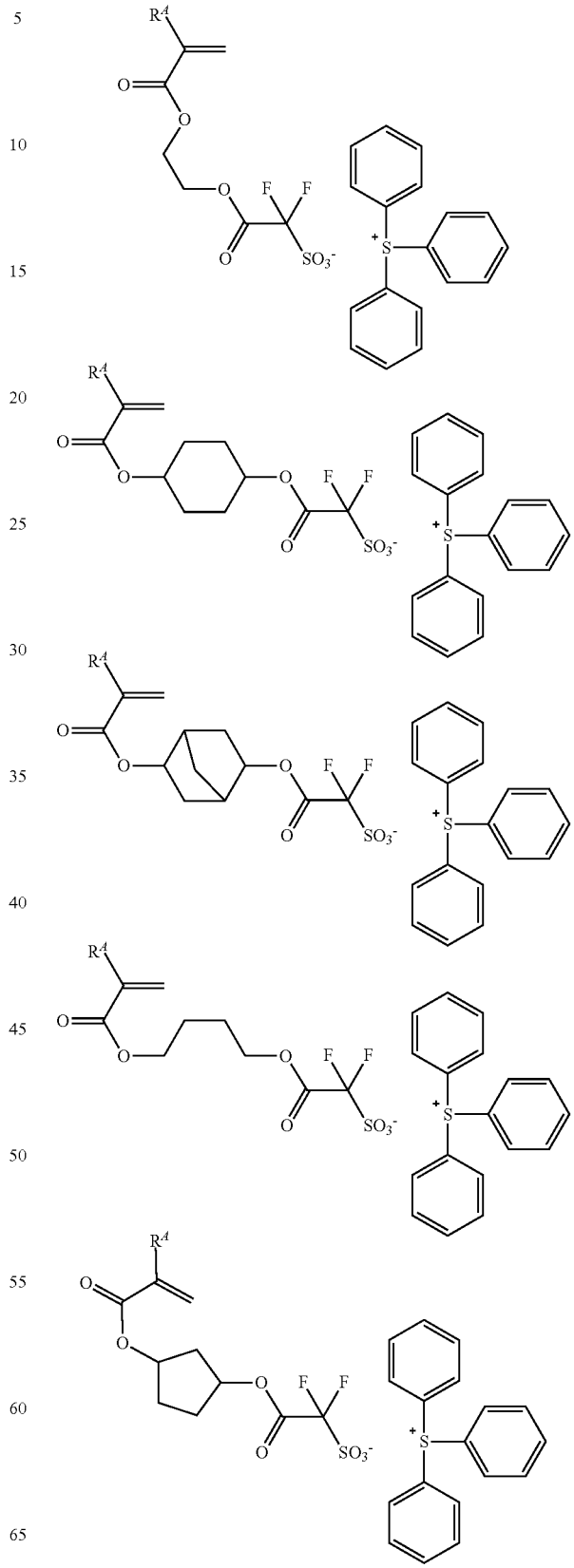

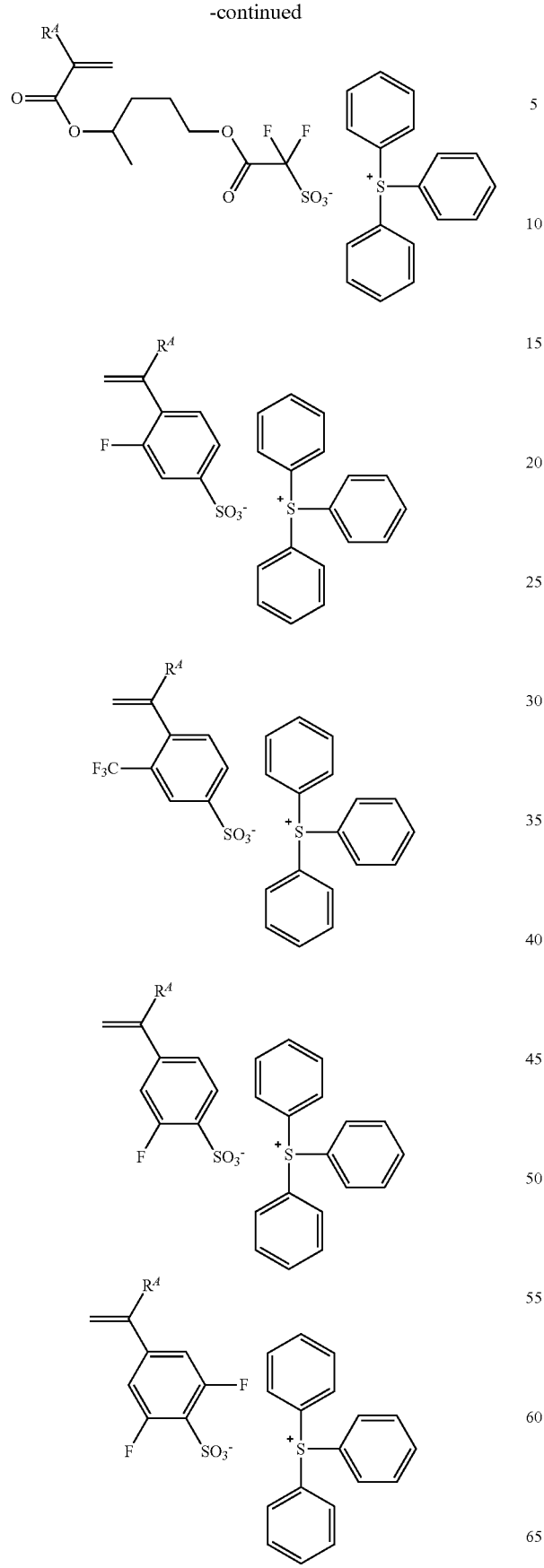
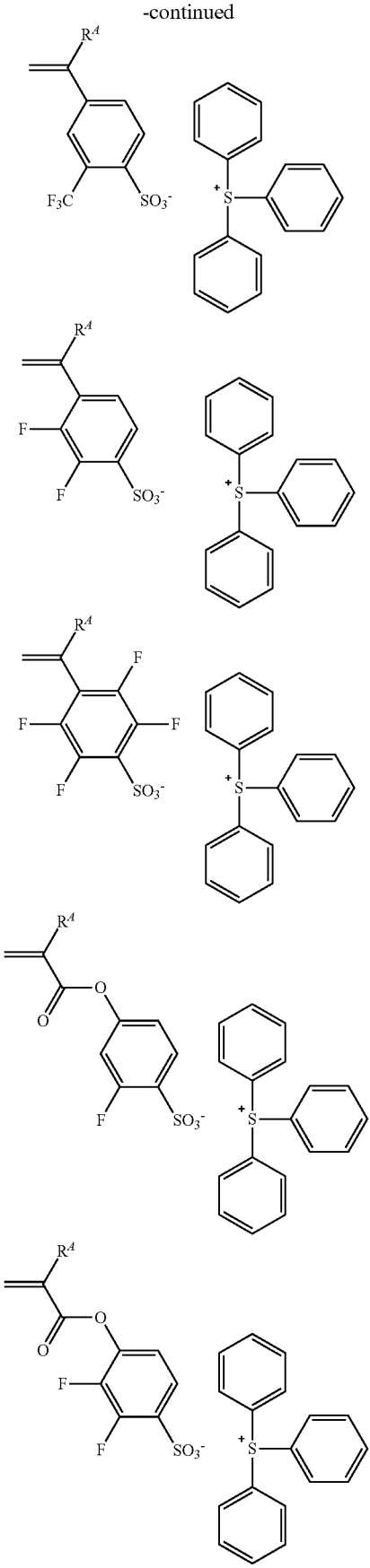

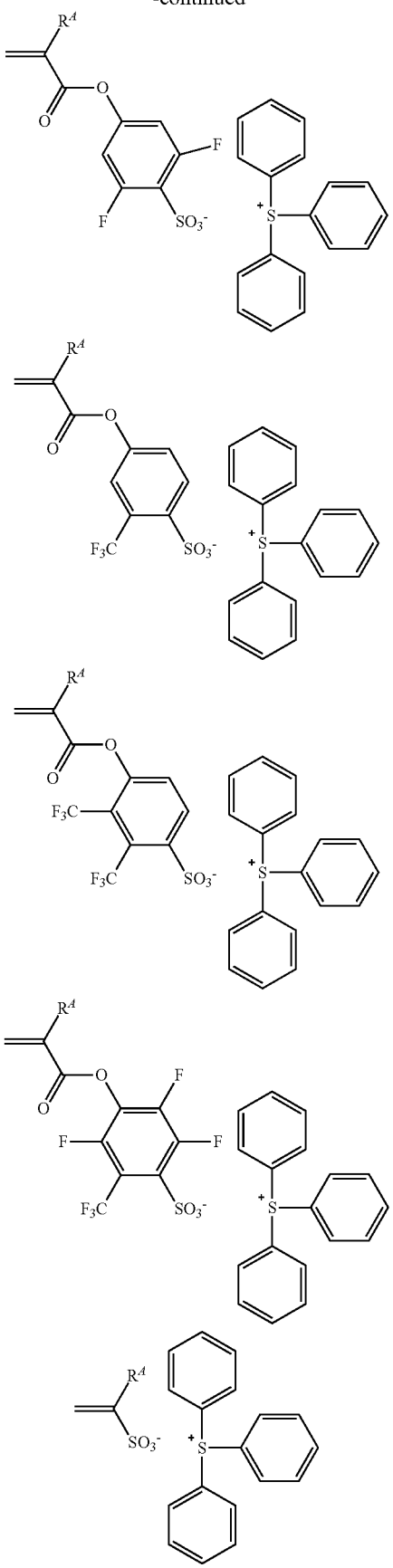

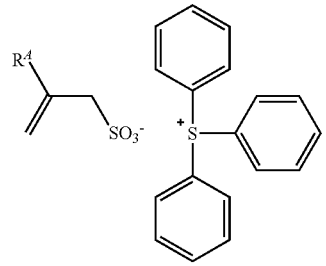

The attachment of an acid generator to the polymer main chain is effective in restraining acid diffusion, thereby preventing a reduction of resolution due to blur by acid diffusion. Also edge roughness is improved since the acid generator is uniformly distributed.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \leq a1 < 1.0$, $0 \leq a2 < 1.0$, $0 < a1+a2 < 1.0$, $0 \leq b \leq 0.9$, $0 \leq c \leq 0.9$, $0 \leq s \leq 0.8$, $0 \leq e \leq 0.8$, and $0 \leq f \leq 0.5$; more preferably $0 \leq a1 \leq 0.9$, $0 \leq a2 \leq 0.9$, $0.1 \leq a1+a2 \leq 0.9$, $0 \leq s \leq 0.8$, $0 \leq s \leq 0.8$, $0 \leq d \leq 0.7$, $0 \leq e \leq 0.7$, and $0 \leq f \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0 < b \leq 1.0$, $0 \leq c \leq 0.9$, $0 \leq d \leq 0.8$, $0 \leq e \leq 0.8$, and $0 \leq f \leq 0.5$; more preferably $0.2 \leq b \leq 1.0$, $0 \leq c \leq 0.8$, $0 \leq d \leq 0.7$, $0 \leq e \leq 0.7$, and $0 \leq f \leq 0.4$; and even more preferably $0.3 \leq b \leq 1.0$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and effecting heat polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylproplonate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

To the resist composition comprising the iodinated aromatic carboxylic salt and the base polymer, defined above, preferably an acid generator is added so that the composition may function as a chemically amplified positive or negative resist composition. The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, sulfonimide or sulfonmethide are preferred. Suitable PAGs include sulfonium salts, iodonium salts, sulfonyldiazomethane, N-sulfonyloxyimide, and oxime-O-sulfonate acid generators. Exemplary acid generators are described in JP-A 2008-111103, paragraphs [0122]-[0142] (U.S. Pat. No. 7,537,880).

As the PAG, compounds having the formula (1) or (2) are also preferably used.

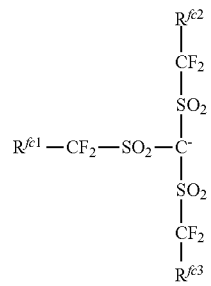
(1)

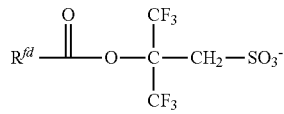
(2)

In formula (1), $R^{101}$, $R^{102}$ and $R^{103}$ are each independently a straight, branched or cyclic $C_1$-$C_{20}$ monovalent hydrocarbon group which may contain a heteroatom, any two of $R^{101}$, $R^{102}$ and $R^{103}$ may bond together to form a ring with the sulfur atom to which they are attached.

In formula (1), $X^-$ is an anion selected from the formulae (1A) to (1D).

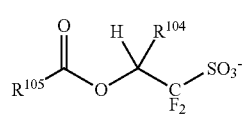
(1A)

(1B)

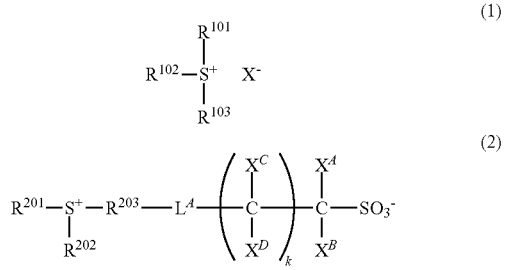
(1C)

(1D)

In formula (1A), $R^{fa}$ is fluorine or a straight, branched or cyclic $C_1$-$C_{40}$ monovalent hydrocarbon group which may contain a heteroatom.

Of the anions of formula (1A), a structure having formula (1A') is preferred.

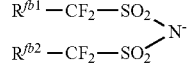
(1A')

In formula (1A'), $R^{104}$ is hydrogen or trifluoromethyl, preferably trifluoromethyl. $R^{105}$ is a straight, branched or cyclic $C_1$-$C_{38}$ monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. Suitable monovalent hydrocarbon groups include methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. Also included are the foregoing groups in which at least one hydrogen is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl, cyano, carbonyl, ether, ester, sulfonic acid ester, carbonate, lactone ring, sultone ring, carboxylic acid anhydride or haloalkyl radical.

With respect to the synthesis of the sulfonium salt having an anion of formula (1A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the sulfonium salt having an anion of formula (1A) are shown below, but not limited thereto.
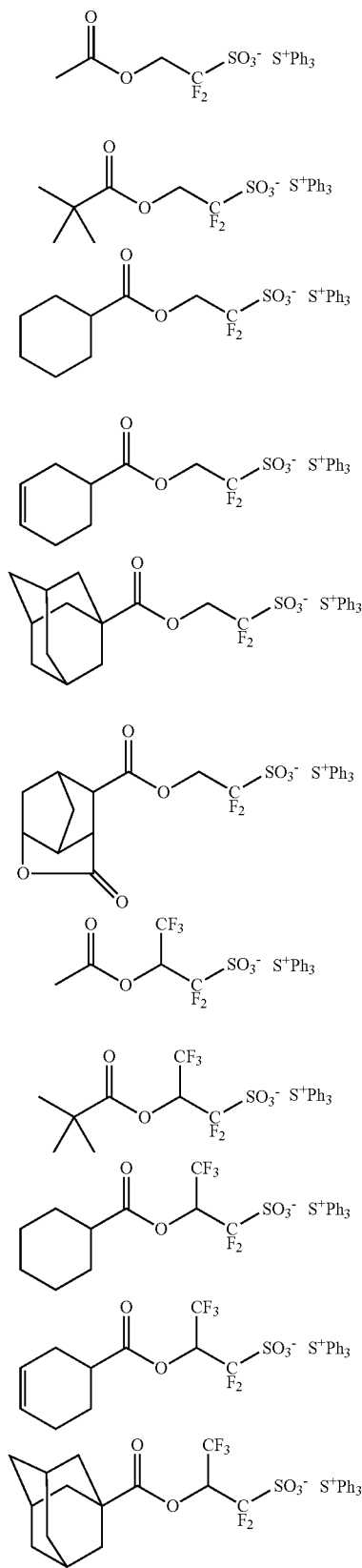
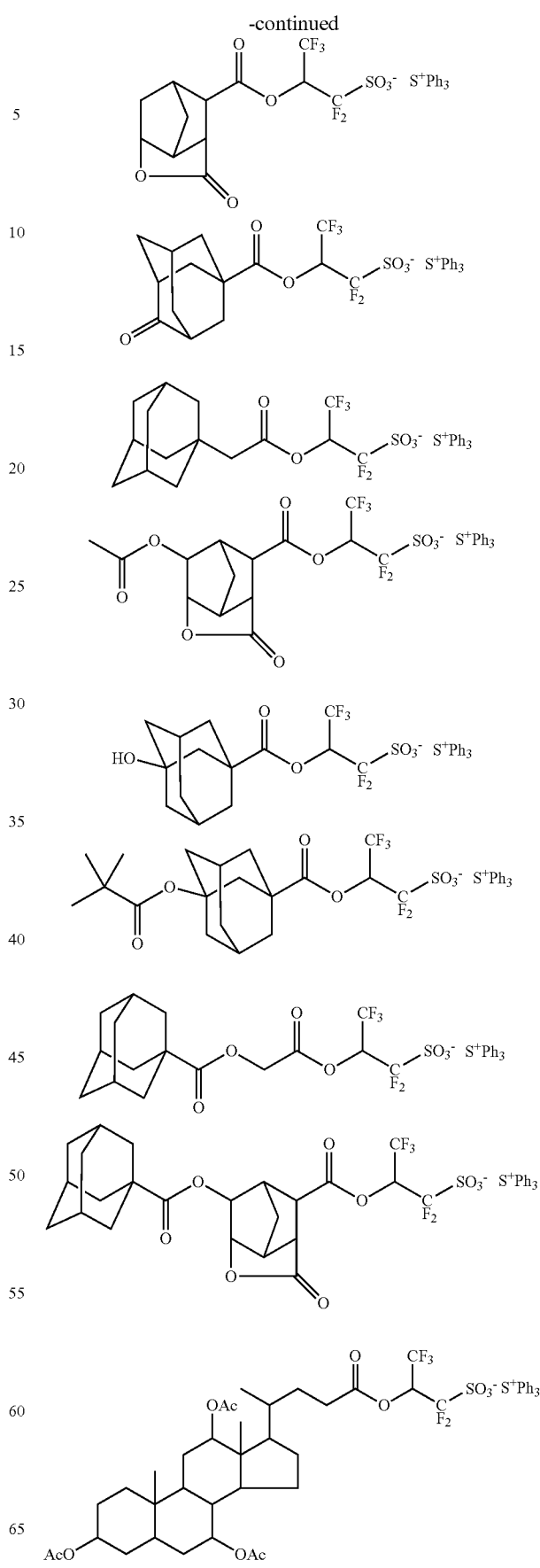

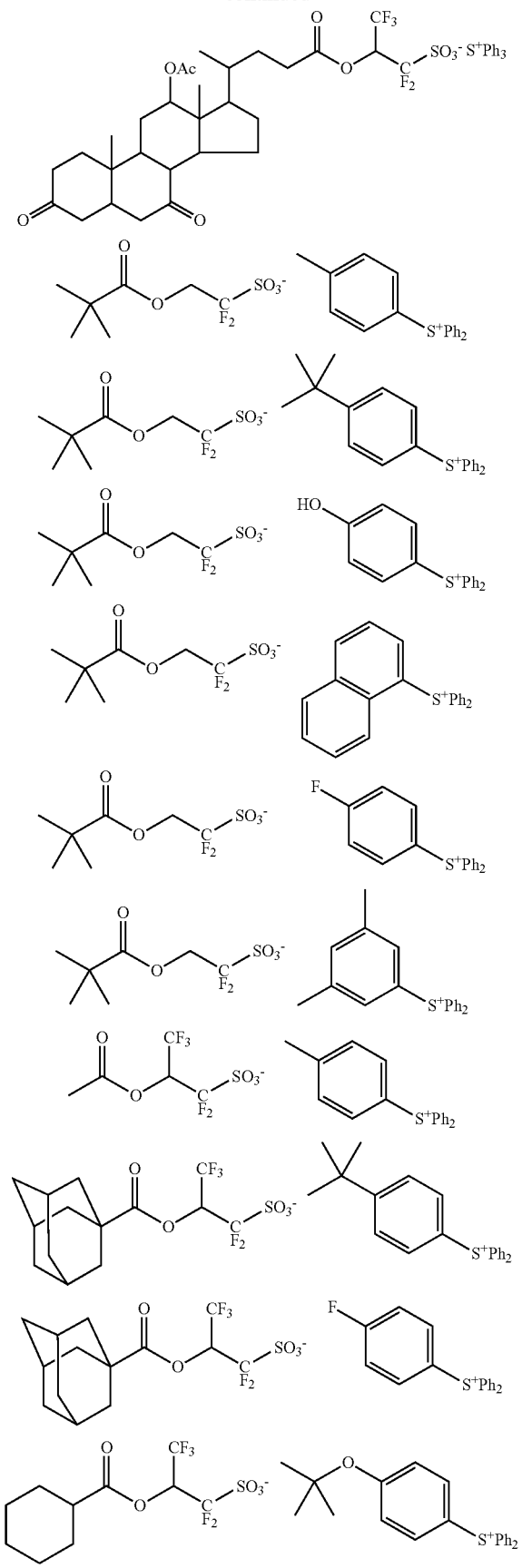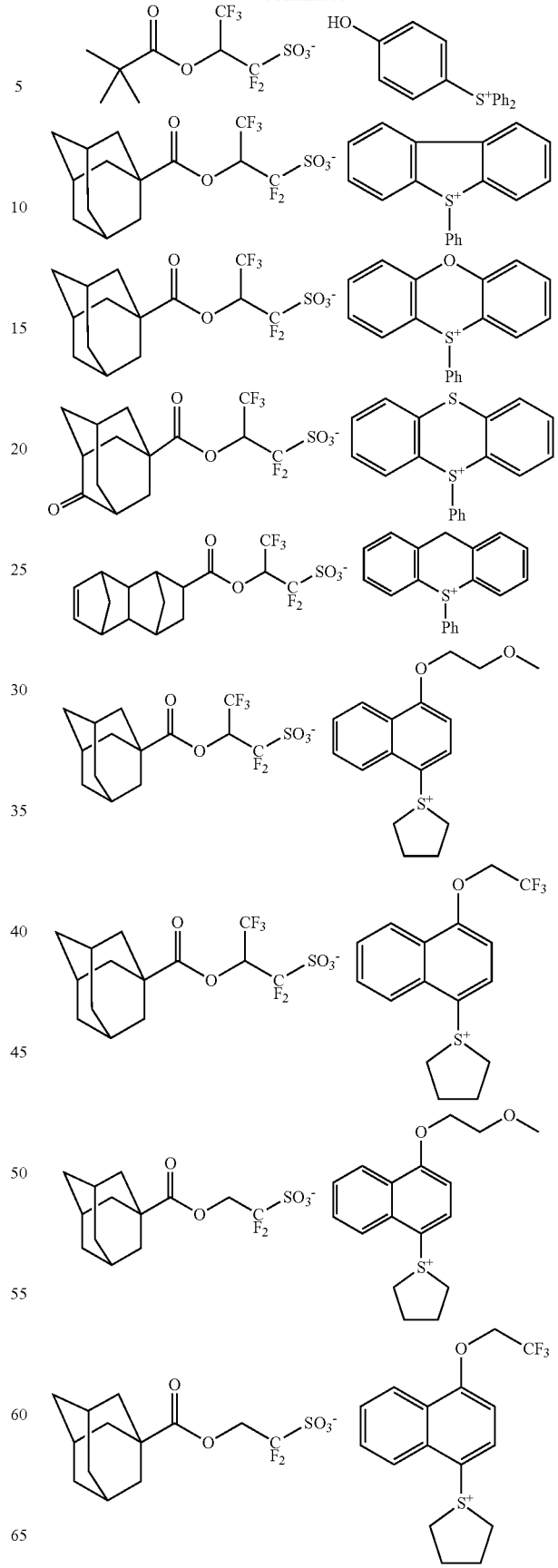

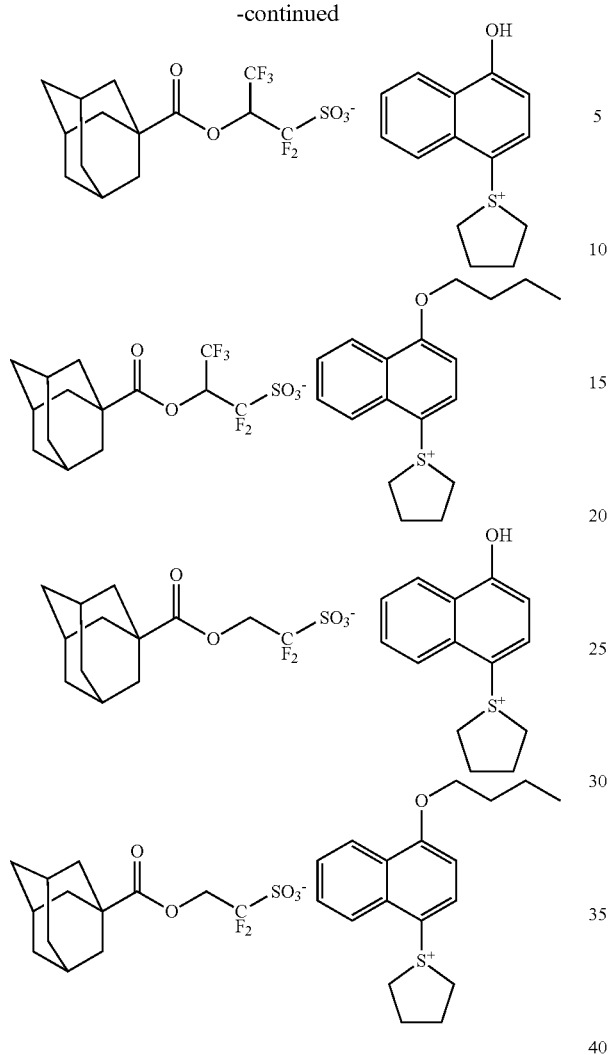

Examples of the sulfonium salt having an anion of formula (1D) are shown below, but not limited thereto.

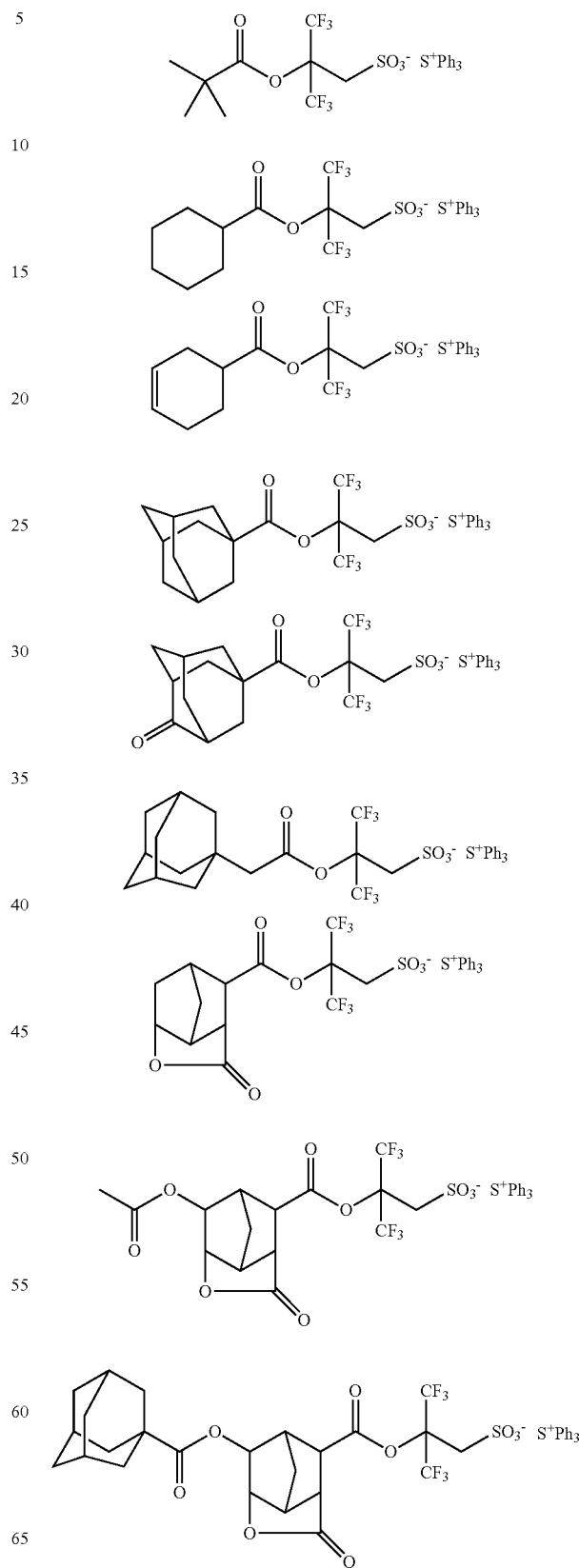

In formula (1B), $R^{fb1}$ and $R^{fb2}$ are each independently fluorine or a straight, branched or cyclic $C_1$-$C_{40}$ monovalent hydrocarbon group which may contain a heteroatom. Suitable monovalent hydrocarbon groups are as exemplified above for $R^{105}$. Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group.

In formula (1C), $R^{fc1}$, $R^{fc2}$ and $R^{fc3}$ are each independently fluorine or a straight, branched or cyclic $C_1$-$C_{40}$ monovalent hydrocarbon group which may contain a heteroatom. Suitable monovalent hydrocarbon groups are as exemplified above for $R^{105}$. Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group.

In formula (1D), $R^{fd}$ is a straight, branched or cyclic $C_1$-$C_{40}$ monovalent hydrocarbon group which may contain a heteroatom. Suitable monovalent hydrocarbon groups are as exemplified above for $R^{105}$.

With respect to the synthesis of the sulfonium salt having an anion of formula (1D), reference is made to JP-A 2010-215608 and JP-A 2014-133723.

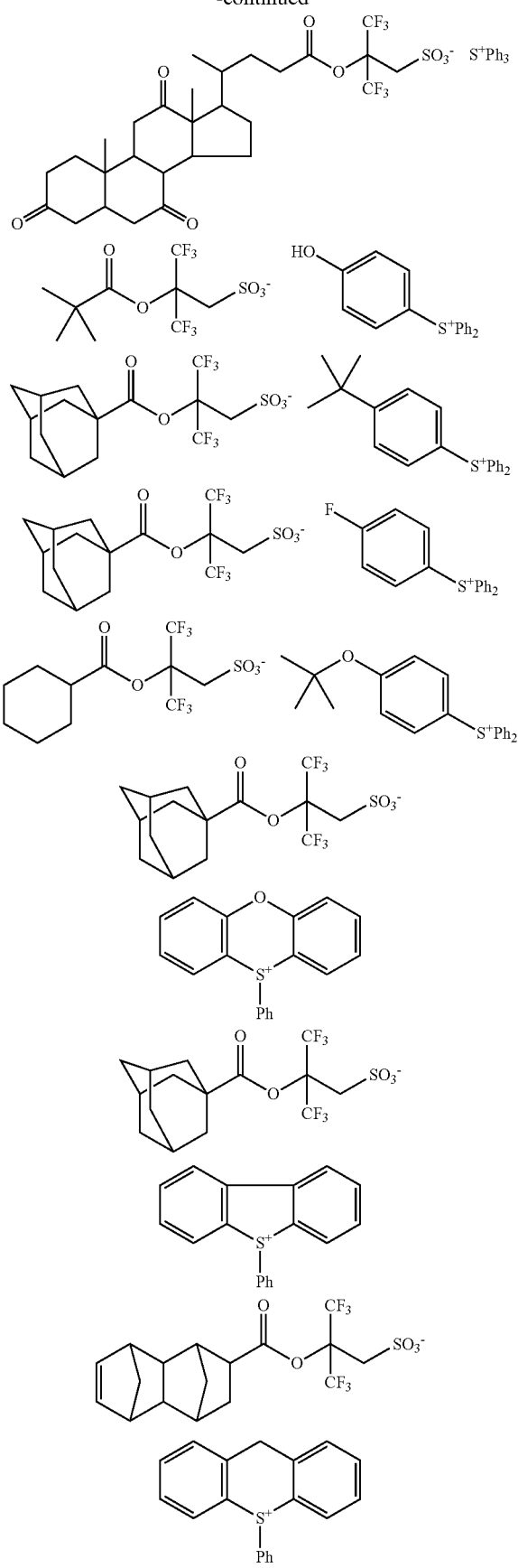

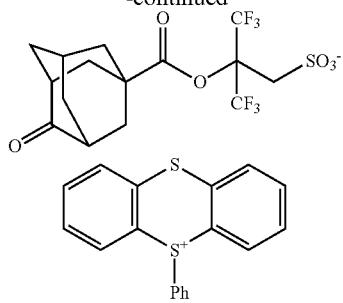

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

In formula (2), $R^{201}$ and $R^{202}$ are each independently a straight, branched or cyclic $C_1$-$C_{30}$ monovalent hydrocarbon group which may contain a heteroatom. $R^{203}$ is a straight, branched or cyclic $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^A$ is a single bond or a straight, branched or cyclic $C_1$-$C_{20}$ divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and k is an integer of 0 to 3.

Suitable monovalent hydrocarbon groups include methyl, ethyl, propyl, isopropyl, n-butyl, s-butyl, t-butyl, n-pentyl, t-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl and anthracenyl. Also included are the foregoing groups in which at least one hydrogen is replaced by a radical containing a heteroatom such as oxygen, sulfur, nitrogen or halogen, or in which at least one carbon is replaced by a radical containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic acid anhydride or haloalkyl radical.

Suitable divalent hydrocarbon groups include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl; and unsaturated cyclic divalent hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl, cyano, carbonyl, ether, ester, sulfonic acid ester, carbonate, lactone ring, sultone ring, carboxylic acid anhydride or haloalkyl radical. Suitable heteroatoms include oxygen, nitrogen, sulfur and halogen, with oxygen being preferred.

Of the PAGs having formula (2), those having formula (2') are preferred.

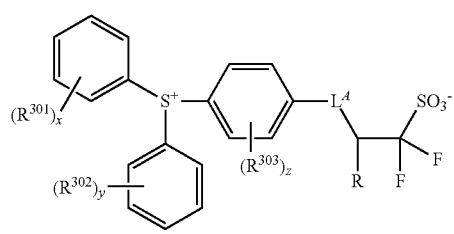

(2')

In formula (2'), $L^A$ is as defined above. R is hydrogen or trifluoromethyl, preferably trifluoromethyl. $R^{301}$, $R^{302}$ and $R^{303}$ are each independently hydrogen or a straight, branched or cyclic $C_1$-$C_{20}$ monovalent hydrocarbon group which may contain a heteroatom. Suitable monovalent hydrocarbon groups are as exemplified above for $R^{105}$. The subscripts x and y each are an integer of 0 to 5, and z is an integer of 0 to 4.

Examples of the PAG having formula (2) are shown below, but not limited thereto. Herein R is as defined above.

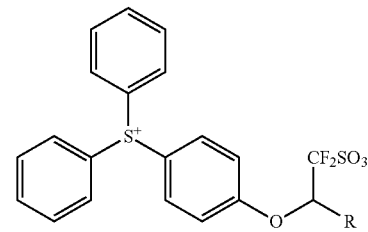

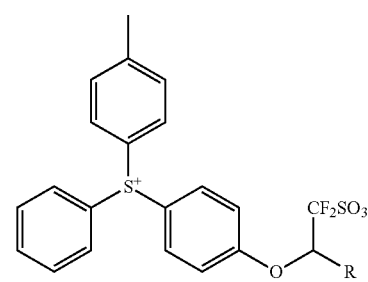

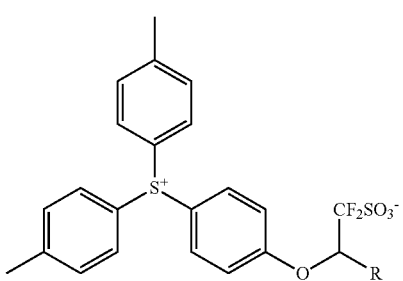

-continued

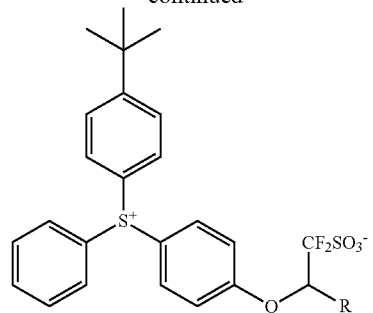

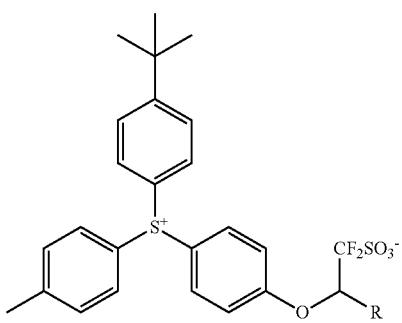

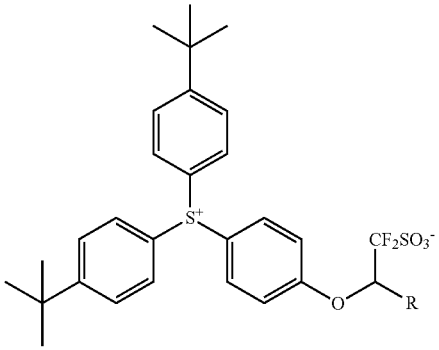

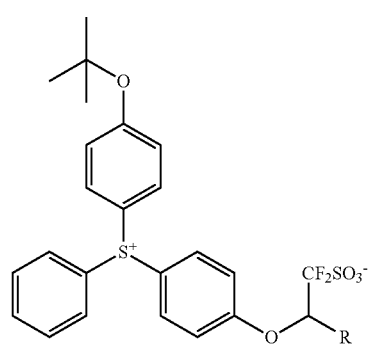

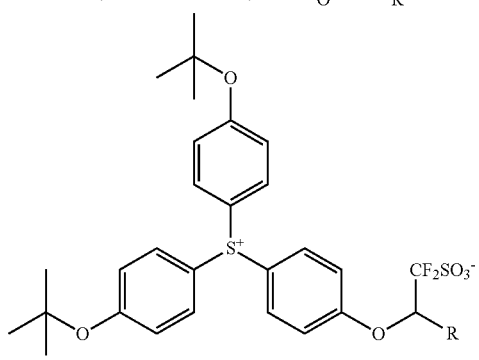

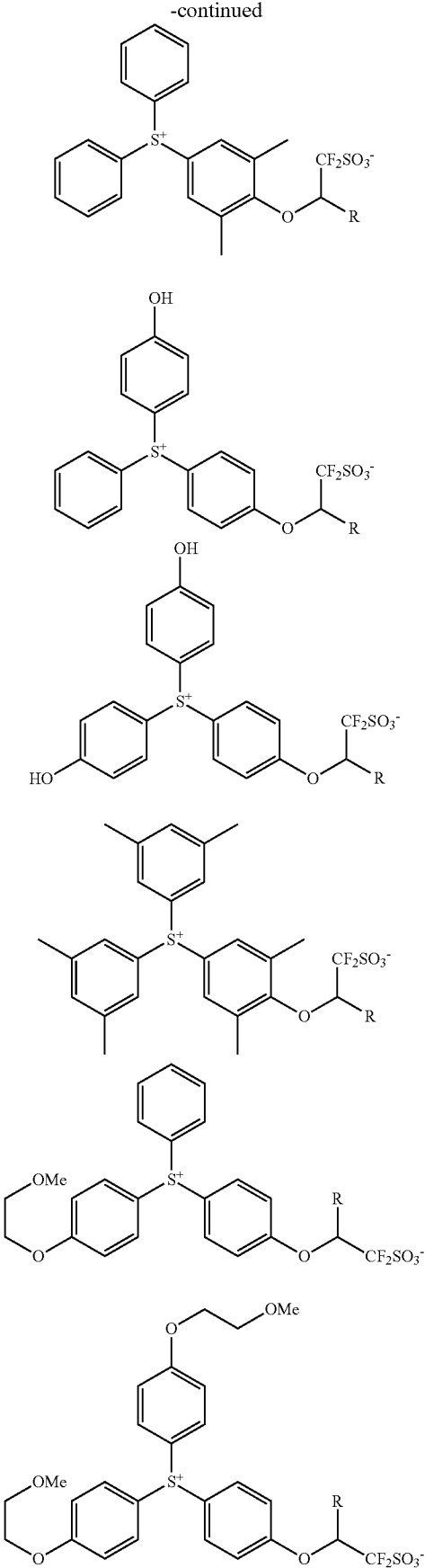
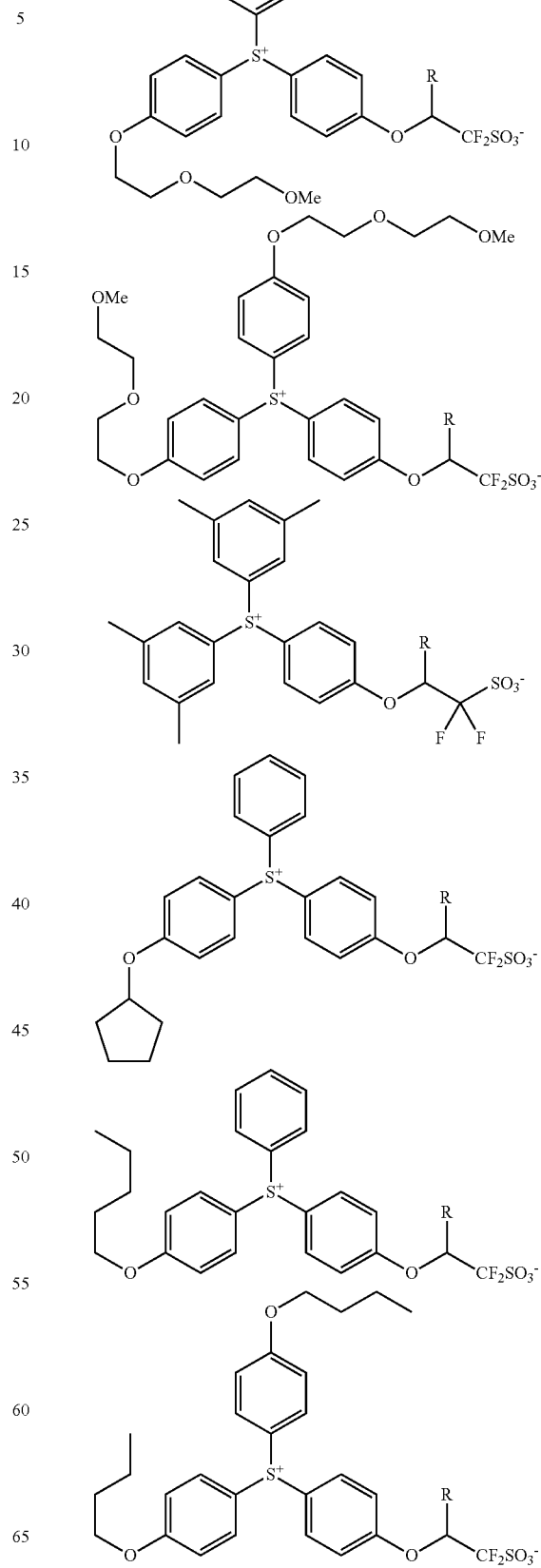

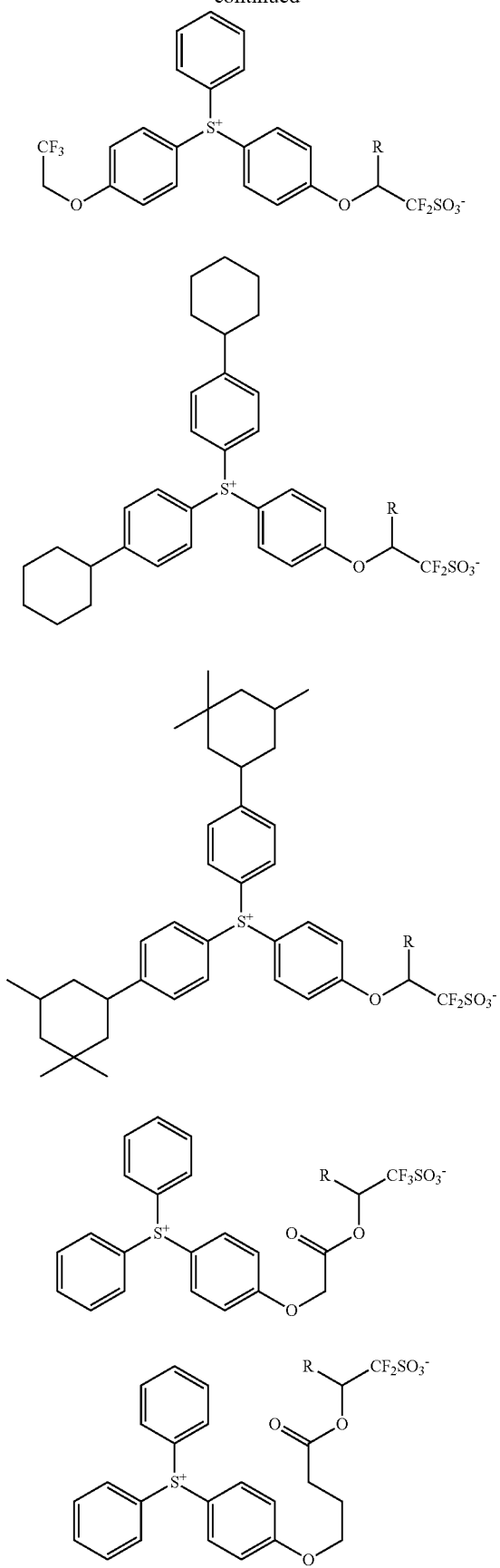
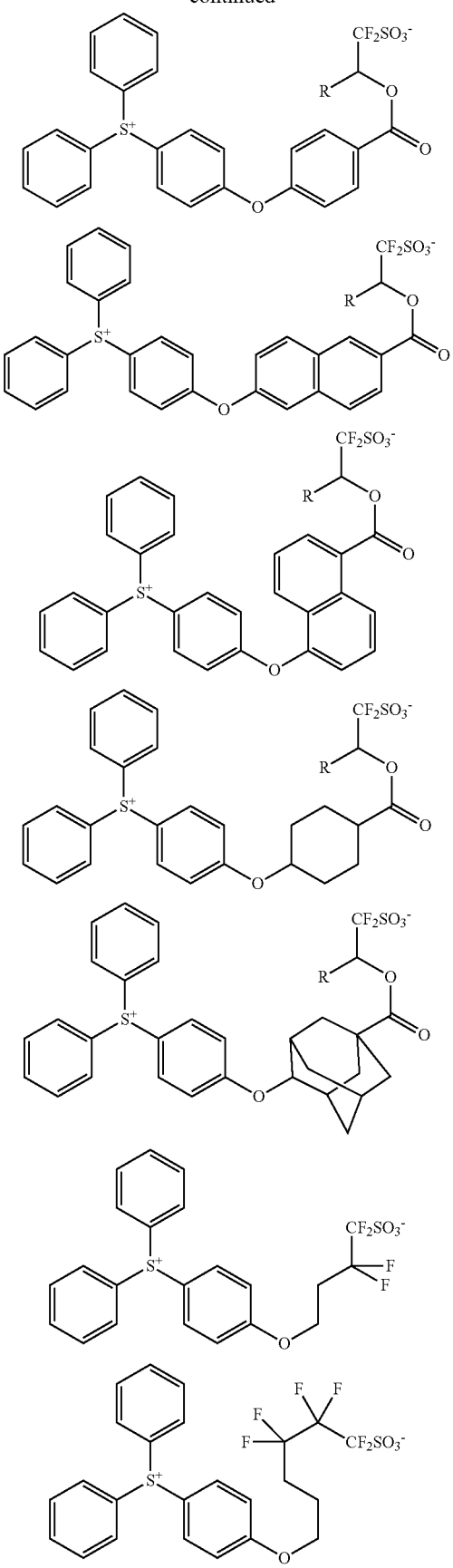

-continued

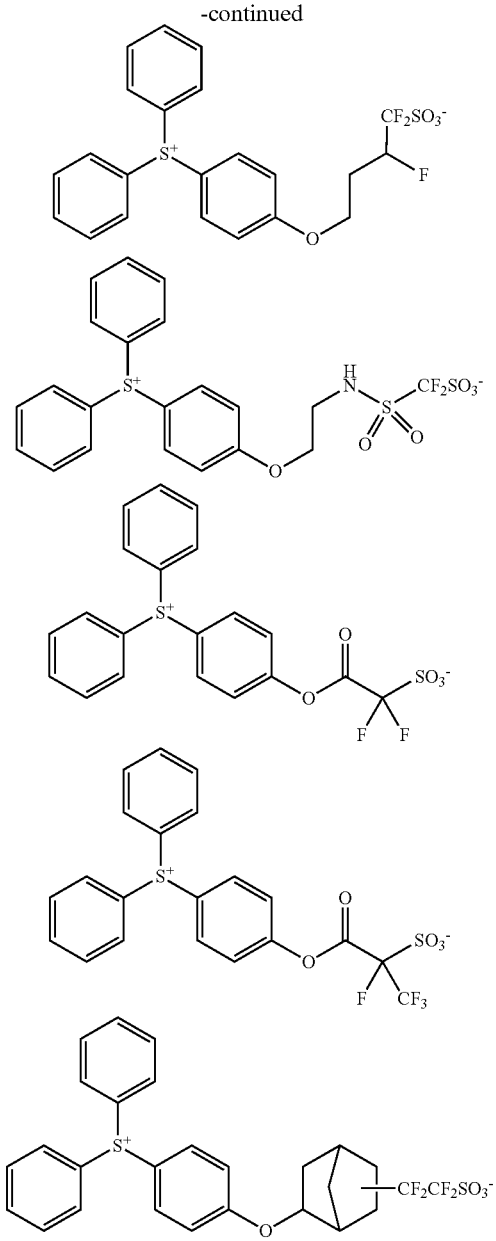

Of the foregoing PAGs, those compounds having an anion of formula (1A') or (1D) are especially preferred because of reduced acid diffusion and high solubility in resist solvent, and those compounds having an anion of formula (2') are especially preferred because of minimized acid diffusion.

An appropriate amount of the acid generator added is 0.1 to 50 parts, more preferably 1 to 40 parts by weight per 100 parts by weight of the base polymer.

Other Components

With the iodinated aromatic carboxylic salt, base polymer, and acid generator, defined above, other components such as an organic solvent, surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when a chemically amplified positive resist composition capable of utilizing acid catalyzed reaction is formulated, the composition has a higher sensitivity and is further improved in the properties described above.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of exposed area.

Examples of the organic solvent used herein are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl other acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Exemplary surfactants are described in JP-A 2008-111103, paragraphs [0165]-[0166]. Inclusion of a surfactant may improve or control the coating characteristics of the resist composition. The surfactant is preferably added in an amount of 0.0001 to 10 parts by weight per 100 parts by weight of the base polymer.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker.

Of the foregoing crosslinkers, examples of suitable epoxy compounds include tri(2,3-epoxypropyl) isocyanurate, trimethylolethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanato, hexamethylene diisocyanate and cyclohexane diisocyanate. Suitable azide compounds include 1,1'-biphenyl-4,4'-bisazide, 4,4'-methylidenobisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

In the resist composition of the invention, a quencher other than the iodinated aromatic carboxylic salt may be blended. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Quenchers of polymer type as described in U.S. Pat. No. 7,598,016 (JP-A 2008-239918) are also useful as the other quencher. The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer.

To the resist composition, a polymeric additive (or water repellency improver) may also be added for improving the water repellency on surface of a resist film as spin coated. The water repellency improver may be used in the topcoatless immersion lithography. Suitable water repellency improvers include polymers having a fluoroalkyl group and polymers having a specific structure with a 1,1,1,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. An appropriate amount of the water repellency improver is 0 to 20 parts, preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Process

The resist composition is used in the fabrication of various integrated circuits. Pattern formation using the resist composition may be performed by well-known lithography processes. The process generally involves coating, prebaking, exposure, and development. If necessary, any additional steps such as PEB may be added.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably 80 to 120° C. for 30 seconds to 20 minutes. The resulting resist film is generally 0.1 to 2 μm thick.

The resist film is then exposed to a desired pattern of high-energy radiation such as UV, deep-UV, EB, EUV, x-ray, soft x-ray, excimer laser light, γ-ray or synchrotron radiation, directly or through a mask. The exposure dose is preferably about 1 to 200 $mJ/cm^2$, more preferably about 10 to 100 $mJ/cm^2$, or about 0.1 to 100 $μC/cm^2$, more preferably about 0.5 to 50 $μC/cm^2$. The resist film is further baked (PEB) on a hotplate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer. It is appreciated that the resist composition of the invention is best suited for micro-patterning using such high-energy radiation as KrF and ArF excimer laser, EB, EUV, x-ray, soft x-ray, γ-ray and synchrotron radiation.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, -hexanol, 1-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentano, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexone, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the invention are given below by way of illustration and not by way of limitation. The abbreviation "pbw" is parts by weight.

Quenchers 1 to 13 in the form of an iodinated aromatic carboxylic salt having the following structure were used in resist compositions. Quenchers 1 to 13 were prepared by mixing an iodinated aromatic group-containing carboxylic acid providing the following anion with a 2,5,8,9-tetraaza-1-phosphabicyclo[3.3.3]undecane, biguanide or phosphazene compound providing the following cation.

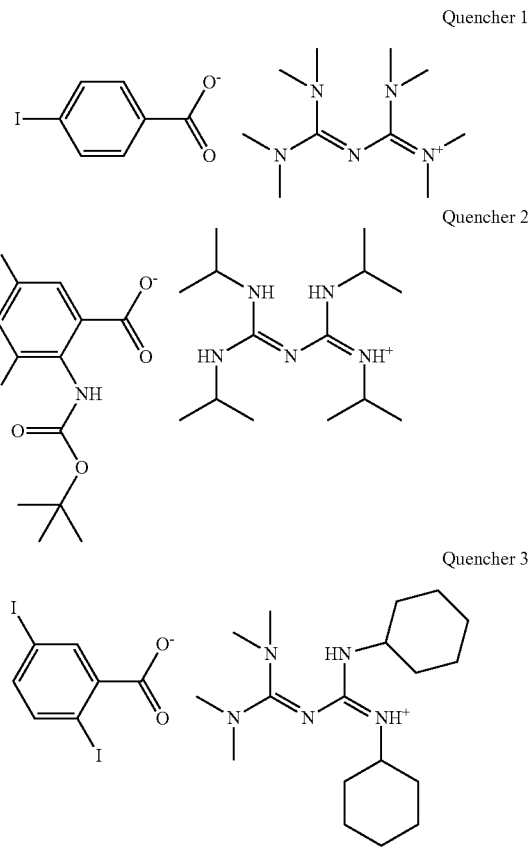

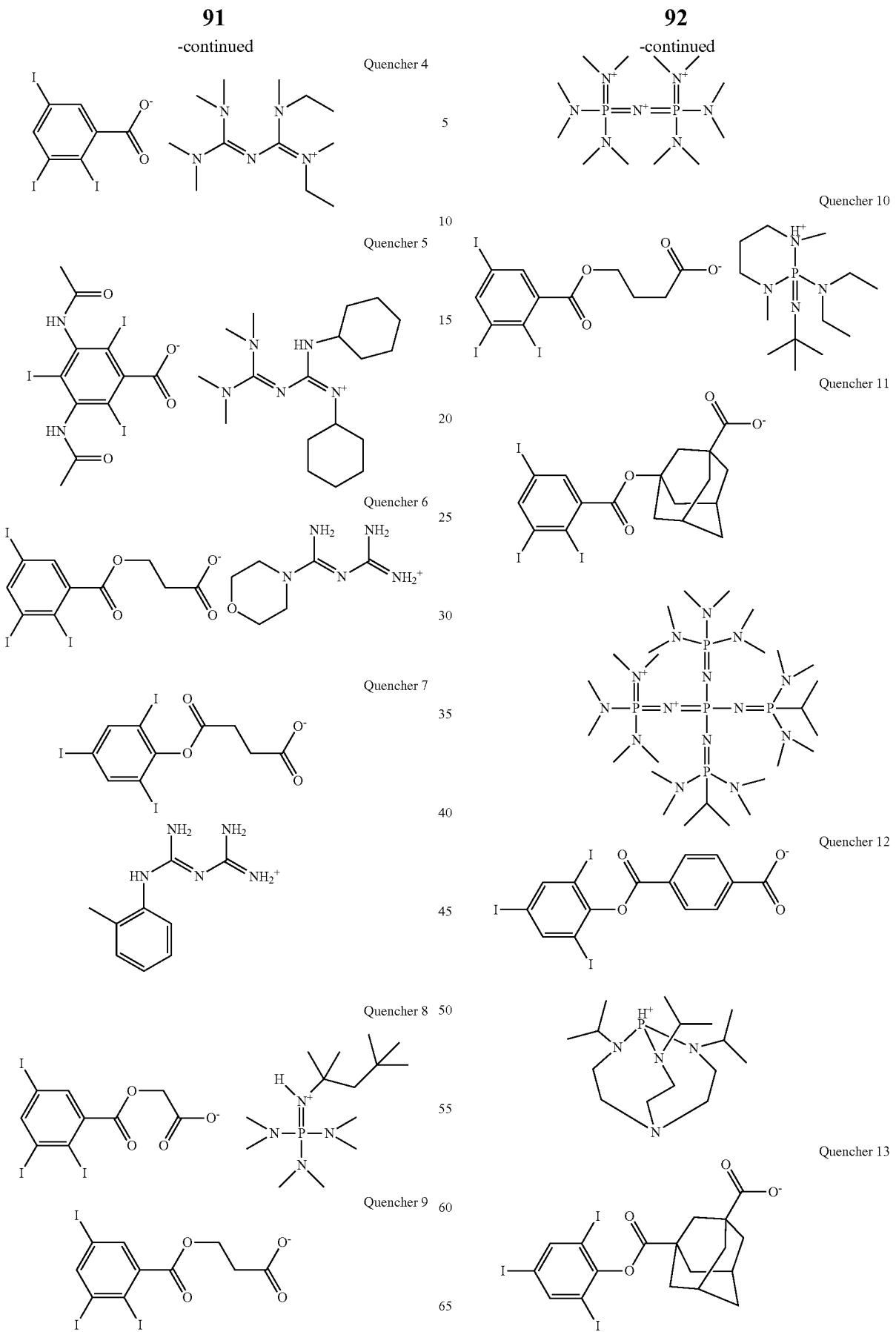

-continued

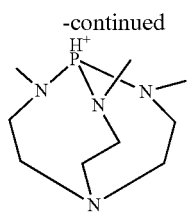

Synthesis Example: Synthesis of Base Polymers (Polymers 1 to 3)

Base polymers were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers, designated Polymers 1 to 3, were analyzed for composition by $^1$H-NMR spectroscopy, and for Mw and Mw/Mn by GPC versus polystyrene standards using THF solvent.

Polymer 1

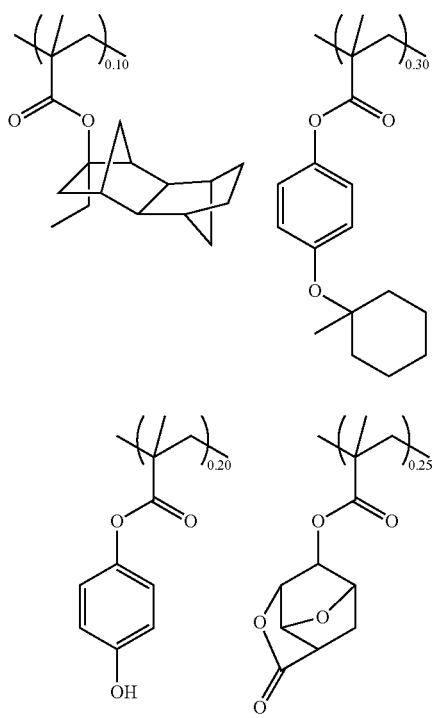

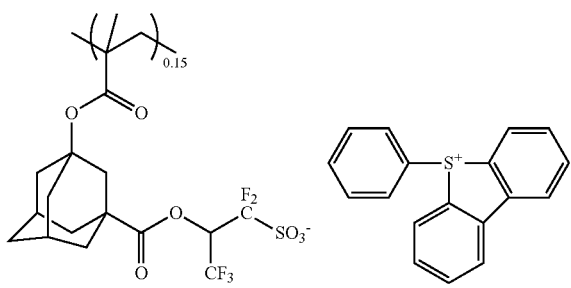

Mw = 7,500
Mw/Mn = 1.76

-continued

Polymer 2

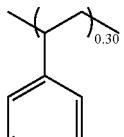 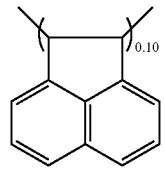

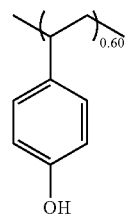

Mw = 5,100
Mw/Mn = 1.46

Polymer 3

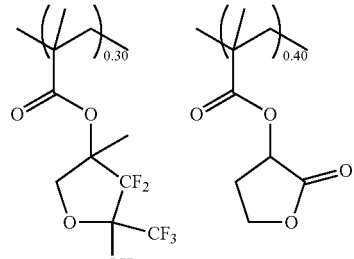

Mw = 8,100
Mw/Mn = 1.65

Examples and Comparative Examples

Resist compositions were prepared by dissolving the polymer and selected components in a solvent in accordance with the recipe shown in Tables 1 and 2, and filtering through a filter having a pore size of 0.2 μm. The solvent contained 100 ppm of surfactant FC-4430 (3M). The components in Tables 1 and 2 are as identified below.

Polymers 1 to 3: identified above

Organic solvents: PGMBA (propylene glycol monomethyl ether acetate)

CyH (cydohexanone)

PGMB (propylene glycol monomethyl ether)

Acid generators: PAG 1 and PAG 2 of the following structural formulae

PAG 1

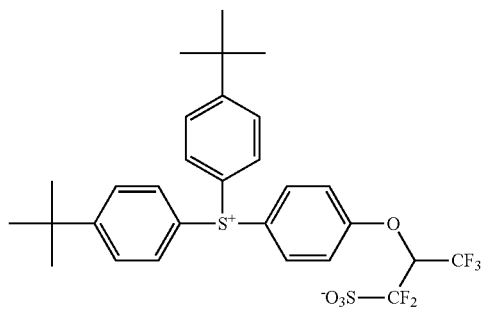

PAG 2

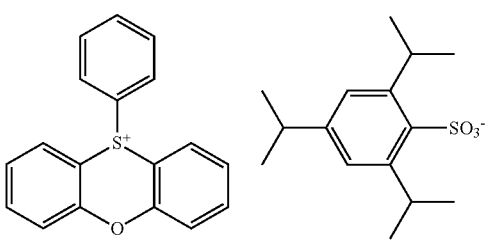

Comparative Quenchers 1 to 6:

Comparative Quencher 1

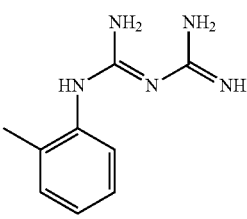

Comparative Quencher 2

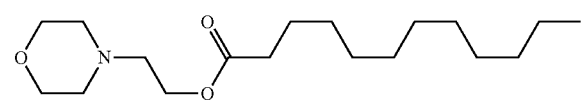

Comparative Quencher 3

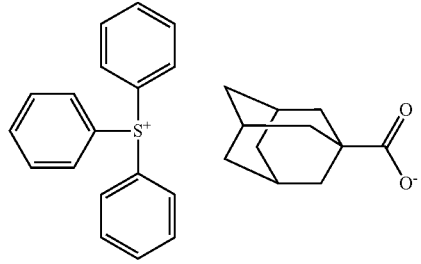

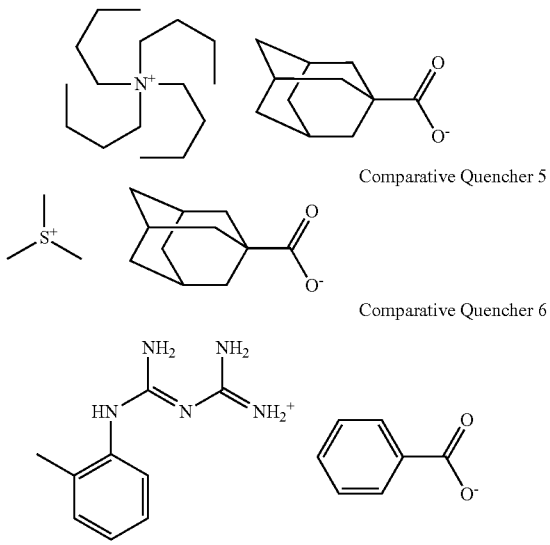

Comparative Quencher 4

Comparative Quencher 5

Comparative Quencher 6

EB Lithography Patterning Test

Each of the resist compositions (Tables 1 and 2) was spin coated onto a silicon substrate (which had been vapor primed with hexamethyldisilazane) and prebaked on a hotplate at 110° C. for 60 seconds to form a resist film of 80 nm thick. Using a system HL-800D (Hitachi Ltd.) at an accelerating voltage of 50 kV, the resist film was exposed imagewise to EB in a vacuum chamber. Immediately after the exposure, the resist film was baked (PEB) on a hotplate at the temperature shown in Tables 1 and 2 for 60 seconds and developed in a 2.38 wt % TMAH aqueous solution for 30 seconds to form a pattern.

The resist pattern was evaluated as follows. In the case of positive resist film, the resolution is a minimum trench size at the exposure dose that provides a resolution as designed of a 120-nm trench pattern. In the case of negative resist film, the resolution is a minimum isolated line size at the exposure dose that provides a resolution as designed of a 120-nm isolated line pattern. In the case of positive resist film, the sensitivity is the exposure dose that provides a resolution to the 120 nm trench pattern. In the case of negative resist film, the sensitivity is the exposure dose that provides a resolution to the 120 nm isolated line pattern. The pattern was observed under SEM to determine LWR. It is noted that Examples 1 to 14 and Comparative Examples 1 to 7 are positive resist compositions, and Example 15 and Comparative Example 8 are negative resist compositions.

The results are shown in Tables 1 and 2.

TABLE 1

|  |  | Polymer (pbw) | Acid generator (pbw) | Quencher (pbw) | Organic solvent (pbw) | PEB (° C.) | Sensitivity ($\mu C/cm^2$) | LWR (nm) | Resolution (nm) |
|---|---|---|---|---|---|---|---|---|---|
| Example | 1 | Polymer 1 (100) | — | Quencher 1 (3.30) | PGMEA (400) CyH (2,000) PGME (100) | 80 | 38 | 4.1 | 75 |
|  | 2 | Polymer 1 (100) | — | Quencher 2 (3.30) | PGMEA (400) CyH (2,000) PGME (100) | 80 | 35 | 4.2 | 75 |
|  | 3 | Polymer 1 (100) | — | Quencher 3 (3.30) | PGMEA (400) CyH (2,000) PGME (100) | 80 | 35 | 4.0 | 75 |

TABLE 1-continued

| | | Polymer (pbw) | Acid generator (pbw) | Quencher (pbw) | Organic solvent (pbw) | PEB (° C.) | Sensitivity (µC/cm²) | LWR (mm) | Resolution (nm) |
|---|---|---|---|---|---|---|---|---|---|
| | 4 | Polymer 1 (100) | — | Quencher 4 (3.80) | PGMEA (400) CyH (2,000) PGME (100) | 80 | 31 | 3.8 | 75 |
| | 5 | Polymer 1 (100) | — | Quencher 5 (3.80) | PGMEA (400) CyH (2,000) PGME (100) | 80 | 34 | 4.0 | 75 |
| | 6 | Polymer 1 (100) | — | Quencher 6 (3.90) | PGMEA (400) CyH (2,000) PGME (100) | 80 | 30 | 4.4 | 75 |
| | 7 | Polymer 1 (100) | — | Quencher 7 (3.90) | PGMEA (400) CyH (2,000) PGME (100) | 80 | 30 | 4.3 | 75 |
| | 8 | Polymer 1 (100) | — | Quencher 8 (3.90) | PGMEA (400) CyH (2,000) PGME (100) | 80 | 30 | 4.4 | 75 |
| | 9 | Polymer 1 (100) | — | Quencher 9 (3.90) | PGMEA (400) CyH (2,000) PGME (100) | 80 | 28 | 4.4 | 75 |
| | 10 | Polymer 1 (100) | — | Quencher 10 (3.90) | PGMEA (400) CyH (2,000) PGME (100) | 80 | 26 | 4.0 | 75 |
| | 11 | Polymer 1 (100) | — | Quencher 11 (3.90) | PGMEA (400) CyH (2,000) PGME (100) | 80 | 27 | 4.1 | 75 |
| | 12 | Polymer 1 (100) | — | Quencher 12 (3.90) | PGMEA (400) CyH (2,000) PGME (100) | 80 | 28 | 4.2 | 75 |
| | 13 | Polymer 1 (100) | — | Quencher 13 (3.90) | PGMEA (400) CyH (2,000) PGME (100) | 80 | 28 | 4.2 | 75 |
| | 14 | Polymer 2 (100) | PAG 2 (10) | Quencher 6 (3.80) | PGMEA (2,000) CyH (500) | 90 | 34 | 5.2 | 80 |
| | 15 | Polymer 3 (100) | PAG 1 (10) | Quencher 6 (3.80) | PGMEA (2,000) CyH (500) | 100 | 40 | 5.9 | 80 |

TABLE 2

| | | Polymer (pbw) | Acid generator (pbw) | Quencher (pbw) | Organic solvent (pbw) | PEB (° C.) | Sensitivity (µC/cm²) | LWR (mm) | Resolution (nm) |
|---|---|---|---|---|---|---|---|---|---|
| Comparative Example | 1 | Polymer 1 (100) | — | Comparative Quencher 1 (2.50) | PGMEA (400) CyH (2,000) PGME (100) | 80 | 59 | 5.8 | 85 |
| | 2 | Polymer 1 (100) | — | Comparative Quencher 2 (2.50) | PGMEA (400) CyH (2,000) PGME (100) | 80 | 56 | 5.8 | 85 |
| | 3 | Polymer 1 (100) | — | Comparative Quencher 3 (3.50) | PGMEA (400) CyH (2,000) PGME (100) | 80 | 50 | 4.6 | 80 |
| | 4 | Polymer 1 (100) | — | Comparative Quencher 4 (3.50) | PGMEA (400) CyH (2,000) PGME (100) | 80 | 52 | 4.9 | 80 |
| | 5 | Polymer 1 (100) | — | Comparative Quencher 5 (2.50) | PGMEA (400) CyH (2,000) PGME (100) | 80 | 64 | 4.6 | 80 |
| | 6 | Polymer 1 (100) | — | Comparative Quencher 6 (3.50) | PGMEA (400) CyH (2,000) PGME (100) | 80 | 54 | 4.8 | 80 |
| | 7 | Polymer 2 (100) | PAG 2 (10) | Comparative Quencher 1 (3.50) | PGMEA (2,000) CyH (500) | 90 | 48 | 7.5 | 85 |
| | 8 | Polymer 3 (100) | PAG 1 (10) | Comparative Quencher 1 (3.50) | PGMEA (2,000) CyH (500) | 100 | 65 | 8.0 | 90 |

It is demonstrated in Tables 1 and 2 that resist compositions comprising 2,5,8,9-tetraaza-1-phosphabicyclo[3.3.3]undecane, biguanide or phosphazene salts of iodinated aromatic group-containing carboxylic acids form patterns having a high sensitivity, satisfactory resolution, and minimal LWR.

Japanese Patent Application No. 2016-183025 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a 2,5,8,9-tetraaza-1-phosphabicyclo[3.3.3]undecane, biguanide or phosphazene salt of an iodinated aromatic group-containing carboxylic acid.

2. The resist composition of claim 1 wherein the salt has the formula (A):

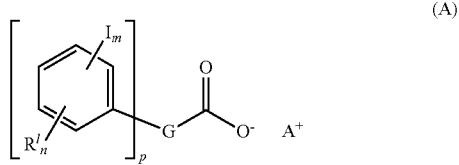

wherein $R^1$ is hydrogen, hydroxyl, a $C_1$-$C_6$ straight, branched or cyclic alkyl group, $C_1$-$C_6$ straight, branched or cyclic alkoxy group, $C_2$-$C_6$ straight, branched or cyclic acyloxy group, fluorine, chlorine, bromine, amino, —$NR^2$—$C(=O)$—$R^3$, or —$NR^2$—$C(=O)$—$O$—$R^3$, $R^2$ is hydrogen or a $C_1$-$C_6$ straight, branched or cyclic alkyl group, $R^3$ is a $C_1$-$C_6$ straight, branched or cyclic alkyl group or $C_2$-$C_8$ straight, branched or cyclic alkenyl group, G is a single bond or a $C_1$-$C_{20}$ (p+1)-valent linking group which may contain an ether, carbonyl, ester, amide, sultone, lactam, carbonate, halogen, hydroxyl or carboxyl moiety, p is an integer of 1 to 3, m is an integer of 1 to 5, n is an integer of 0 to 3, $A^+$ is a cation having the formula (A)-1, (A)-2 or (A)-3:

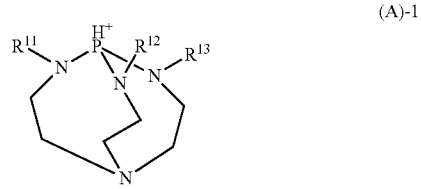

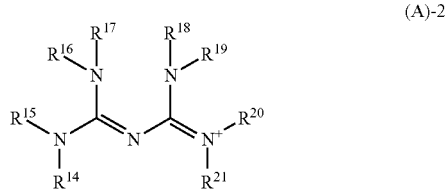

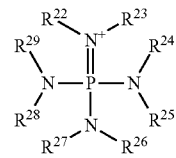

wherein $R^{11}$ to $R^{13}$ are each independently hydrogen, a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, $R^{14}$ to $R^{21}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxyl, thiol, or nitro moiety, or a pair of $R^{14}$ and $R^{15}$, $R^{15}$ and $R^{16}$, $R^{16}$ and $R^{17}$, $R^{17}$ and $R^{18}$, $R^{19}$ and $R^{19}$, $R^{19}$ and $R^{20}$, or $R^{20}$ and $R^{21}$ may bond together to form a ring which may contain an ether moiety, $R^{22}$ to $R^{29}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxyl, thiol, or nitro moiety, or a pair of $R^{22}$ and $R^{23}$, $R^{23}$ and $R^{24}$, $R^{24}$ and $R^{25}$, $R^{25}$ and $R^{26}$, $R^{26}$ and $R^{27}$, or $R^{27}$ and $R^{28}$ may bond together to form a ring or $R^{23}$ and $R^{24}$, $R^{25}$ and $R^{26}$, $R^{27}$ and $R^{28}$, or $R^{28}$ and $R^{29}$, taken together, may form a group having the formula (A)-3-1, or when $R^{22}$ is hydrogen, $R^{23}$ may be a group having the formula (A)-3-2:

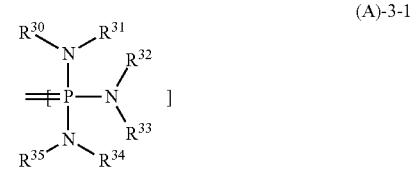

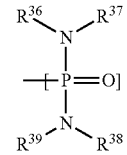

wherein $R^{30}$ to $R^{39}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, or a pair of $R^{30}$ and $R^{31}$, $R^{31}$ and $R^{32}$, $R^{32}$ and $R^{33}$, $R^{33}$ and $R^{34}$, $R^{34}$ and $R^{35}$, $R^{36}$ and $R^{37}$, or $R^{38}$ and $R^{39}$ may bond together to form a ring, or $R^{30}$ and $R^{31}$, $R^{32}$ and $R^{33}$, or $R^{34}$ and $R^{35}$, taken together, may form a group having the formula (A)-3-1.

3. The resist composition of claim 1, further comprising an acid generator capable of generating sulfonic acid, sulfonimide or sulfonmethide.

4. The resist composition of claim 1, further comprising an organic solvent.

5. The resist composition of claim 1 wherein the base polymer comprises recurring units having the formula (a1) or recurring units having the formula (a2):

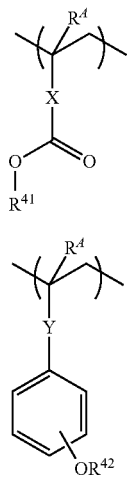

(a1)

(a2)

wherein $R^A$ is each independently hydrogen or methyl, $R^{41}$ and $R^{42}$ are each independently an acid labile group, X is a single bond, phenylene, naphthylene, or a $C_1$-$C_{12}$ linking group containing ester moiety or lactone ring, and Y is a single bond or ester group.

6. The resist composition of claim 5, further comprising a dissolution inhibitor.

7. The resist composition of claim 5 which is a chemically amplified positive resist composition.

8. The resist composition of claim 1 wherein the base polymer is an acid labile group-free polymer.

9. The resist composition of claim 8, further comprising a crosslinker.

10. The resist composition of claim 8 which is a chemically amplified negative resist composition.

11. The resist composition of claim 1 wherein the base polymer further comprises recurring units of at least one type selected from recurring units having the formulae (f1) to (f3):

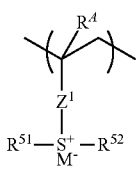

(f1)

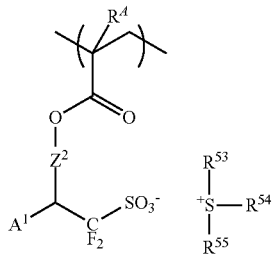

(f2)

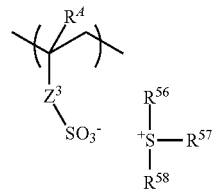

(f3)

wherein $R^A$ is each independently hydrogen or methyl, $Z^1$ is a single bond, phenylene, —O—$Z^{11}$—, or —C(=O)—$Z^{12}$—$Z^{11}$—, $Z^{11}$ is a straight, branched or cyclic $C_1$-$C_6$ alkylene group or straight, branched or cyclic $C_2$-$C_6$ alkenylene group which may contain a carbonyl, ester, ether or hydroxyl moiety, or phenylene group, $Z^{12}$ is —O— or —NH—, $R^{51}$, $R^{52}$, $R^{53}$, $R^{54}$, $R^{55}$, $R^{56}$, $R^{57}$, and $R^{58}$ are each independently a straight, branched or cyclic $C_1$-$C_{12}$ alkyl group which may contain a carbonyl, ester or ether moiety, or a $C_6$-$C_{12}$ aryl, $C_7$-$C_{20}$ aralkyl, or mercaptophenyl group, $Z^2$ is a single bond, —$Z^{21}$—C(=O)—O—, —$Z^{21}$—O—, or —$Z^{21}$—O—C(=O)—, $Z^{21}$ is a straight, branched or cyclic $C_1$-$C_{12}$ alkylene group which may contain a carbonyl, ester or ether moiety, $Z^3$ is a single bond, methylene, ethylene, phenylene, fluorinated phenylene, —O—$Z^{31}$—, or —C(=O)—$Z^{32}$—$Z^{31}$—, $Z^{31}$ is a straight, branched or cyclic $C_1$-$C_6$ alkylene group or straight, branched or cyclic $C_2$-$C_6$ alkenylene group which may contain a carbonyl, ester, ether or hydroxyl moiety, or a phenylene, fluorinated phenylene or trifluoromethyl-substituted phenylene group, $Z^{32}$ is —O— or —NH—, $A^1$ is hydrogen or trifluoromethyl, and $M^-$ is a non-nucleophilic counter ion.

12. The resist composition of claim 1, further comprising a surfactant.

13. A pattern forming process comprising the steps of coating the resist composition of claim 1 onto a substrate, baking, exposing the resulting resist film to high-energy radiation, and developing with a developer.

14. The process of claim 13 wherein the high-energy radiation is ArF excimer laser of wavelength 193 nm or KrF excimer laser of wavelength 248 nm.

15. The process of claim 13 wherein the high-energy radiation is EB or EUV of wavelength 3 to 15 nm.

\* \* \* \* \*